United States Patent
Lim et al.

(10) Patent No.: US 10,548,500 B2
(45) Date of Patent: Feb. 4, 2020

(54) APPARATUS FOR MEASURING BIOELECTRICAL SIGNALS

(71) Applicant: SAMSUNG ELECTRONICS CO., LTD., Suwon-si (KR)

(72) Inventors: Se-hoon Lim, Suwon-si (KR); Jun-hyung Park, Seoul (KR); Hee-jae Jo, Suwon-si (KR); Jang-beom Yang, Gwangju (KR); Jae-min Jung, Suwon-si (KR); Eun-mi Oh, Seoul (KR); Jong-ho Choi, Suwon-si (KR); Jun-ho Koh, Suwon-si (KR); Chang-Hyun Lee, Suwon-si (KR); Yong-hyun Lim, Suwon-si (KR); Hae-in Chun, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1073 days.

(21) Appl. No.: 14/947,640

(22) Filed: Nov. 20, 2015

(65) Prior Publication Data

US 2016/0143554 A1    May 26, 2016

Related U.S. Application Data

(60) Provisional application No. 62/082,298, filed on Nov. 20, 2014.

(30) Foreign Application Priority Data

Jan. 5, 2015   (KR) .......................... 10-2015-0000927
May 15, 2015   (KR) .......................... 10-2015-0068188

(51) Int. Cl.
*A61B 5/0478* (2006.01)
*A61B 5/00* (2006.01)
*A61B 5/04* (2006.01)

(52) U.S. Cl.
CPC .......... *A61B 5/0478* (2013.01); *A61B 5/6803* (2013.01); *A61B 5/6814* (2013.01);
(Continued)

(58) Field of Classification Search
CPC ... A61B 5/6803; A61B 5/6804; A61B 5/6814; A61B 5/6843; A61B 5/0006;
(Continued)

(56) References Cited

U.S. PATENT DOCUMENTS 4,033,334 A  *  7/1977  Fletcher ............... A61B 5/0408
                                                           600/383
4,706,679 A  *  11/1987  Schmidt ............... A61B 5/0478
                                                           600/383

(Continued)

FOREIGN PATENT DOCUMENTS

KR    10-2004-0095336 A    11/2004
KR       10-0670810 B1      1/2007
(Continued)

OTHER PUBLICATIONS

Yun-Hsuan Chen et al., "Polymer-based dry electrodes for high user comfort ECG/EEG measurements", 8th International Conference Exhibition on Integration Issues of Miniaturized Systems—MEMS NEMS, ICs and Electronic Components, 2014, 8 pages total, retrieved from URL <https://limo.libis.be/primo-explore/fulldisplay?docid=LIRIAS1732981&context=L&vid=Lirias&search_scope=Lirias&tab=default_tab&lang=en_US>.

(Continued)

*Primary Examiner* — Lee S Cohen
*Assistant Examiner* — Erin M Cardinal
(74) *Attorney, Agent, or Firm* — Sughrue Mion, PLLC

(57) ABSTRACT

An apparatus for measuring bioelectrical signals is provided. The apparatus includes a sensor electrode, a sensor support, and a main body. The sensor electrode has a tapering portion (Continued)

that narrows toward one end and a protruding portion that extends from the one end of the tapering portion, contacts a body part, and senses bioelectrical signals. The sensor support maintains the contact between the sensor electrode and the body part. The main body is connected to the sensor support and is wearable on a living body.

19 Claims, 65 Drawing Sheets

(52) U.S. Cl.
CPC .......... *A61B 5/6843* (2013.01); *A61B 5/0006* (2013.01); *A61B 5/04012* (2013.01); *A61B 5/6804* (2013.01); *A61B 5/746* (2013.01); *A61B 2560/0475* (2013.01)

(58) Field of Classification Search
CPC . A61B 5/04001; A61B 5/04012; A61B 5/746; A61B 2560/0475; A61B 5/0478
USPC .......................................................... 600/383
See application file for complete search history.

(56) References Cited

U.S. PATENT DOCUMENTS

| | | | | |
|---|---|---|---|---|
| 4,967,038 | A * | 10/1990 | Gevins | A61B 5/0017 600/383 |
| 5,038,782 | A | 8/1991 | Gevins et al. | |
| 6,201,982 | B1 * | 3/2001 | Menkes | A61B 5/0478 600/383 |
| 6,510,333 | B1 * | 1/2003 | Licata | A61B 5/04026 600/383 |
| 8,996,100 | B2 | 3/2015 | Van Herk et al. | |
| 2002/0029005 | A1 * | 3/2002 | Levendowski | A61B 5/0478 600/545 |
| 2007/0225585 | A1 | 9/2007 | Washbon et al. | |
| 2009/0088619 | A1 | 4/2009 | Turner et al. | |
| 2009/0105576 | A1 | 4/2009 | Do et al. | |
| 2010/0198042 | A1 * | 8/2010 | Popescu | A61B 5/0478 600/383 |
| 2010/0280573 | A1 | 11/2010 | Schouenborg | |
| 2011/0054288 | A1 | 3/2011 | Besio | |
| 2011/0315548 | A1 * | 12/2011 | Yamashita | A61B 5/0478 204/403.01 |
| 2012/0049998 | A1 * | 3/2012 | Lim | H04M 1/72569 340/1.1 |
| 2012/0136233 | A1 * | 5/2012 | Yamashita | A61B 5/0478 600/393 |
| 2012/0179019 | A1 * | 7/2012 | Fadem | A61B 5/0484 600/383 |
| 2012/0226127 | A1 | 9/2012 | Asjes et al. | |
| 2012/0245451 | A1 * | 9/2012 | Wada | A61B 5/0478 600/386 |
| 2013/0274583 | A1 | 10/2013 | Heck | |
| 2014/0051960 | A1 * | 2/2014 | Badower | A61B 5/00 600/383 |
| 2015/0133762 | A1 * | 5/2015 | Hayakawa | A61B 5/0478 600/383 |
| 2015/0238100 | A1 * | 8/2015 | Lin | A61B 5/0478 600/393 |
| 2016/0022165 | A1 * | 1/2016 | Sackellares | A61B 5/0478 600/383 |

FOREIGN PATENT DOCUMENTS

| | | |
|---|---|---|
| KR | 10-1308540 B1 | 9/2013 |
| WO | 00/045701 A1 | 8/2000 |
| WO | 2008/109699 A2 | 9/2008 |

OTHER PUBLICATIONS

"Tagungsband Smart Systems Integration", 6 pages, retrieved from URL <https://www.mesago.de/de/SSI2019/Formulare/Tagungsband/index.htm>, retrieved on Jul. 2, 2018.
"Table of contents", 2014, Smart Systems Integration, Mesago Messe Frankfurt Group, retrieved from URL <https://www.mesago.de/v3/download.php?name=SSI2014_Inhaltsverzeichnisweb.pdf&c_id=8000&file=ssi2014_inhaltsverzeichnis_web.pdf>.
Evelyn Hettich et al., "Proceedings Smart Systems Integration 2014", letter Jul. 3, 2018, 9 pages indicating sale date of Polymer-based dry electrodes . . . available since Mar. 26, 2014.
Y. H. Chen et al., "Comb-shaped Polymer-based Dry Electrodes for EEG/ECG Measurements with High User Comfort", 35th Annual International Conference of the IEEE EMBS, Osaka, Japan, Jul. 3-7, 2013, pp. 551-554.
Presentation from Yun-Hsuan Chen, "Soft, Comfortable Polymer Dry Electrodes for High Quality ECG and EEG Recording", International Electronic Conference on Sensors and Application, May 15, 2014, 26 pages.
Yun-Hsuan Chen et al., "Soft, Comfortable Polymer Dry Electrodes for High Quality ECG and EEG Recording", Sensors 2014, vol. 14, Dec. 10, 2014, pp. 23758-23780.
Communication dated Jul. 23, 2018, issued by the European Patent Office in counterpart European Application No. 15860505.5.
Communication dated Mar. 7, 2016, issued by the International Searching Authority in counterpart International Application No. PCT/KR2015/012544 (PCT/ISA/210 & PCT/ISA/237).
Communication dated Oct. 18, 2017 by the European Patent Office in counterpart European Patent Application No. 15860505.5.

* cited by examiner

APPARATUS FOR MEASURING BIOELECTRICAL SIGNALS

CROSS-REFERENCE TO RELATED APPLICATION

This application claims the benefit of U.S. Provisional Patent Application No. 62/082,298, filed on Nov. 20, 2014, in the U.S. Patent and Trademark Office, and priority from Korean Patent Application Nos. 10-2015-0000927 and 10-2015-0068188, respectively filed on Jan. 5, 2015 and May 15, 2015, in the Korean Intellectual Property Office, the disclosures of which are incorporated by reference herein in their entirety.

BACKGROUND

1. Field

The present disclosure relates to apparatuses for measuring bioelectrical signals, sensor electrodes for measuring bioelectrical signals, sensor support structures, and systems, and more particularly, to an apparatus for measuring bioelectrical signals to minimize the effect of a movement of a living body, a sensor electrode for measuring bioelectrical signals, a sensor support structure, and a system for processing bioelectrical signals.

2. Description of the Related Art

Bioelectrical signals that are changes in potential or current produced across muscle cells or nerve cells of a subject are obtained by collecting and analyzing changes in electrical signals detected through electrodes attached to the subject's body.

For example, brain waves are bioelectrical signals obtained by extracting information about changes in potential, which occur according to the activity of the brain, from the scalp and recording the changes. Brain waves are complex waves having various changes in potential and the frequency and amplitude of the brain waves are analyzed. Examples of a method of obtaining brain waves include an invasive method in which an electrode is directly inserted into the scalp or the skull and a non-invasive method in which an electrode is attached to the scalp. Although the invasive method may accurately measure brain waves, it is not easy to use the invasive method because the invasive method has a risk of infection when an electrode is inserted to measure brain waves and there is pain during an insertion procedure. Accordingly, the non-invasive method is often used to measure brain waves. A wet method using an electrolyte such as gel or saline is commonly used as the non-invasive method. However, the wet method is inconvenient because a process of attaching a sensor is complex and the hair gets wet due to the gel or saline. Also, the wet method suffers signal distortion when the gel hardens or the saline evaporates.

In order to address these disadvantages, a dry method that does not use gel or saline has been studied. The dry method uses a conductor such as gold or silver as an electrode in order to obtain bioelectrical signals without an electrolyte. In the dry method, a conductor electrode and a surface of a living body contact each other. However, when the living body moves, the conductor electrode may slip out of the scalp, thereby leading to signal distortion. Also, contact impedance is affected by the amount of pressure applied during the contact, and it is advantageous to maintain a low impedance in order to obtain high-quality data without signal distortion. However, most existing dry sensors have no structure for maintaining a contact pressure or have a very complex structure.

SUMMARY

It is an aspect to provide an apparatus for stably measuring bioelectrical signals which may enable a sensor to be kept in contact with a living body at a constant pressure and may stably measure bioelectrical signals even when the living body moves, sensor electrodes for measuring bioelectrical signals, sensor support structures, and systems for processing bioelectrical signals.

Additional aspects will be set forth in part in the description which follows and, in part, will be apparent from the description, or may be learned by practice of the presented exemplary embodiments.

According to an aspect of an exemplary embodiment, an apparatus for measuring bioelectrical signals includes a sensor electrode comprising a tapering portion that narrows toward one end and a protruding portion that extends from the one end of the tapering portion and contacts a body part, and senses bioelectrical signals; a sensor support configured to support the sensor electrode to maintain the contact between the sensor electrode and the body part; and a main body connected to the sensor support and being wearable on a living body.

The tapering portion may have a cross-sectional area that decreases toward one end. For example, the tapering portion may have a truncated cone shape, a truncated elliptic cone shape, or a truncated pyramid shape and the protruding portion may protrude from a top surface of the truncated cone shape, the truncated elliptic cone shape, or the truncated pyramid shape.

A gradient of a longitudinal section of an outer surface of the protruding portion may be greater than a gradient of a longitudinal section of an outer surface of the tapering portion with respect to a bottom surface of the other end of the tapering portion. The tapering portion may have a cone shape having a streamlined cross-section. The tapering portion may have any one of a cylindrical shape, an elliptic cylindrical shape, and a polyprism shape. The protruding portion may also have a tapering shape. One end of the protruding portion may have a blunt shape such as a hemispheric shape and may minimize pain in the living body when contacting the living body. An outer surface of the tapering portion and an outer surface of the protruding portion may be connected to have a gently curved surface. For example, the outer surface of the tapering portion and the outer surface of the protruding portion may be connected to have a curved surface that is concave inward. In other words, the tapering portion and the protruding portion may be shaped so that the gradient of the outer surface of the tapering portion and the outer surface of the protruding portion increases upward with respect to the mount surface. One end of the protruding portion may have a blunt shape such as a hemispheric shape.

The protruding portion may comprise a flexible material, may have a flexibility greater than a flexibility of the tapering portion, and may be bent when contacting the body part so that a side portion of the protruding portion contacts the body part, and the tapering portion supports the protruding portion.

The flexible material may be conductive silicone or conductive rubber.

The sensor electrode may be a dry electrode. For example, the sensor electrode may include a conductive polymer such as conductive silicone or conductive rubber. The tapering portion and the protruding portion of the sensor electrode may be integrally formed with each other. The tapering portion and the protruding portion of the sensor electrode may include different materials and may be adhered to each other. For example, the protruding portion may include conductive silicone or conductive rubber having a high flexibility and the tapering portion may include a synthetic resin having a flexibility that is less than the flexibility of the protruding portion. The tapering portion may include a conductive material or a non-conductive material. When the tapering portion includes a non-conductive material, an additional conductor that is electrically connected to the protruding portion may be inserted into the tapering portion.

The apparatus may further comprise an electrode supporter to which the other end of the tapering portion is attached and which is configured to support the sensor electrode, wherein an electrode pattern for electrically connecting to the sensor electrode is provided on one of a mount surface of the electrode supporter on which the sensor electrode is mounted and a rear surface of the electrode supporter.

The electrode supporter may have a circular plate shape, a quadrangular plate shape, or a long bar shape. When the sensor electrode measures brain waves, the electrode supporter may be bent to conform to the head of the living body. An element including the sensor electrode and the electrode supporter may be understood as one sensor module. The sensor module used herein refers to an individual electrode that directly contacts the living body and the sensor module used herein refers to an element including one or more sensor electrodes and the electrode supporter that supports the one or more sensor electrodes. Since any structure that supports the sensor electrode may be understood as the electrode supporter, when the sensor module includes one sensor electrode, the sensor module may be understood as the sensor electrode unless being confused.

A plurality of the sensor electrodes may be provided on the electrode supporter. For example, when the electrode supporter has a long bar shape, the sensor electrodes may be arranged in one or more columns in a longitudinal direction. When the tapering portions of the sensor electrodes have elliptic cone shapes, the sensor electrodes may be arranged so that long axes of cross-sections of the tapering portions are parallel or perpendicular to directions of the one or more columns. Alternatively, when the cross-sections of the tapering portions of the sensor electrodes have streamlined shapes, measuring electrodes may be arranged so that longitudinal directions of the cross-sections of the tapering portions are parallel or perpendicular to the directions of the one or more columns. Alternatively, only one sensor electrode may be provided on the electrode supporter.

The electrode supporter may include a hard or soft non-conductive material. In this case, an electrode pattern for electrically connecting the sensor electrode may be provided on a rear surface or a surface of the electrode supporter that supports the sensor electrode.

The apparatus may further comprise a sensor circuit disposed on the rear surface of the electrode supporter or disposed inside the electrode supporter and configured to process bioelectrical signals detected by the sensor electrode into analog signals or digital signals.

The sensor circuit may include an analog amplification circuit that amplifies bioelectrical signals detected by the sensor electrode. Furthermore, the sensor circuit may further include an analog-digital conversion circuit configured to convert analog signals amplified by the analog amplification circuit into digital signals. Also, the sensor circuit may further include a wired communication module or a wireless communication module configured to transmit bioelectrical signals detected by the sensor electrode to the outside. The sensor circuit may further include at least one of a battery, a wireless power module, and an energy harvest module. A cable configured to electrically connect the sensor circuit to an external electronic device may be further provided. The cable may include at least one of a power line that supplies power to the sensor circuit, a bioelectrical signal line that transmits bioelectrical signals detected by the sensor electrode, a reference signal line, and a ground signal line.

The electrode supporter may include a conductive material. In this case, the electrode supporter may be electrically connected to the sensor electrode. The sensor electrode and the electrode supporter may be integrally formed by using the same material. Alternatively, the sensor electrode and the electrode supporter may include different materials and the sensor electrode may be attached to the electrode supporter.

Examples of bioelectrical signals measured by the sensor electrode may include brain waves, electrocardiogram (ECG) signals, electromyogram (EMG) signals, electroneurogram (ENG) signals, and electrooculogram (EOG) signals.

The sensor support may elastically support the sensor electrode so that the sensor electrode moves in 3-axis directions.

The sensor support may comprise a spiral spring, and the sensor electrode is coupled to one of two ends of the spiral spring, wherein a surface on which one end of the spiral spring is placed protrudes beyond a surface on which the other end of the spiral spring is placed.

An elasticity of the spiral spring along a central axis of the spiral spring may be greater than an elasticity of the spiral spring in a direction perpendicular to the central axis of the spiral spring.

When the sensor support elastically supports the sensor electrode, the term elasticity refers to the tendency of a solid object to return to its original shape after it has been deformed due to an external force and the term support refers to the activity of holding up the solid object. The sensor support may have an elasticity due to a spiral spring shape and may hold up and support the sensor electrode when the sensor electrode contacts the body part.

The apparatus may further comprise a connection frame configured to connect the sensor support and the main body and to allow the sensor electrode to contact a head of the living body.

The main body may comprise a slot, and one end of the connection frame may be detachably inserted into the slot.

At least a part of an outer surface of the connection portion between a connection frame and the spiral spring of the sensor support may have a linear or gently curved shape. For example, the outer surface of the connection portion between the connection frame and the spiral spring may have a predetermined curvature.

The sensor support may include an edge support having a ring shape that surrounds an outer surface of the spiral spring and an outer end of the spiral spring may be attached to the edge support. A connection portion between the connection frame and the edge support may have an outer surface having a gently curved shape.

The spiral spring may have a circular, elliptic, or atypical spiral shape.

The sensor support may include a first edge support that is spaced apart by a predetermined interval from the sensor electrode (or the sensor module) and surrounds an outer surface of the sensor electrode (or the sensor module) and at least two first springs that connect the sensor electrode (or the sensor module) and the first edge support.

The sensor support may include a second edge support that is spaced apart by a predetermined interval from the first edge support and surrounds the first edge support and at least two second springs that connect the first and second edge supports.

The sensor support may include plastic or a metal.

A cable that transmits bioelectrical signals measured by the sensor electrode or supplies power to the sensor electrode may be located outside the sensor support. If necessary, the cable may be buried in the sensor support.

The main body may be worn on an ear of the living body. For example, the main body may include a housing having an earset shape that is worn on the ear of the living body. Furthermore, the apparatus may further include a connection frame configured to connect the sensor support and the main body and to allow the sensor electrode (or the sensor module) to contact the ear of the living body. The apparatus may be an apparatus for measuring brain waves by using the sensor electrode.

The main body may include a slot, and one end of the connection frame may be detachably inserted into the slot. A cable including at least one of a power line that supplies power to the sensor electrode and a signal line that receives bioelectrical signals measured by the sensor electrode may be buried in the connection frame, and at least one of a power connector terminal and a signal connector terminal that are electrically connected to the cable may be provided in the slot. A plurality of the slots may be formed so that a plurality of the connection frames extend from the head of the living body in different directions to different positions on the head of the living body.

The connection frame may include an elastic material to elastically press the sensor module to the scalp of the living body. The sensor module may include a plurality of the sensor electrodes. The plurality of sensor electrodes of the sensor module may be arranged in one or more columns in a longitudinal direction on the connection frame. In this case, the connection frame may be understood as an electrode supporter that supports the plurality of sensor electrodes. When the plurality of sensor electrodes include the tapering portions having elliptic cone shapes, the tapering portions may be arranged so that long axes of cross-sections of the tapering portions are parallel or perpendicular to directions of the one or more columns.

When the main body has an earset shape that is worn on an ear of the living body, an ear connection ring for fixing the main body to the auricle of the ear of the living body may be provided. The ear connection ring may be connected to the main body by using an elastic bar. An ear insertion ring inserted into an external part of the ear of the living body and configured to fix the main body to the ear of the living body may be further provided. A reference electrode or a ground electrode may be provided on the ear insertion ring. The ear insertion ring may be formed by extending from the ear connection ring. Alternatively, a sensor support configured to connect the ear connection ring and the ear insertion ring and to elastically support the ear insertion ring so that the ear insertion ring moves in 3-axis directions may be further provided. The sensor support may include a spiral spring, one inner end of the spiral spring may be supported by the ear connection ring, and the ear insertion ring may be coupled to an outer end portion of the spiral spring. A sound output device for outputting a sound may be provided on the ear insertion ring or a hollow portion for inputting an external sound into the ear may be formed in the ear insertion ring.

The apparatus may further comprise an auxiliary frame having a hair band shape, a cap shape, or a headband shape, and configured to fix the main body to a head of the living body. The auxiliary frame may be detachably coupled to the main body. For example, when the auxiliary frame has a hair band shape, the auxiliary frame may be detachably inserted into at least one of a plurality of slots formed in the main body. One pair of the main bodies may be coupled to both ends of the auxiliary frame and respectively worn on the left ear and the right ear of the living body. A main circuit may be embedded in the main body as described below. The one pair of main bodies coupled to the both ends of the auxiliary frame may include a main body in which the main circuit is embedded and a dummy main body in which the main circuit is not embedded.

The main body of the apparatus may be coupled to an inner surface of a cap. The main body may have a circular band shape or a semicircular band shape to be located along an inner circumferential surface of a cap. The main body may include a housing having a circular band shape or a semicircular band shape. The sensor electrode may be provided on at least one portion of an inner surface of the housing that contacts the scalp of the user when the main body is worn on the user and may contact the head of the living body when the cap is worn on the head of the living body. Also, the apparatus may further include a connection frame configured to support the sensor support, extending from the main body, and configured to allow the sensor electrode to contact the head of the living body when the cap is worn on the head of the living body. Furthermore, the apparatus may further include an attachment/detachment coupler configured to detachably couple the main body to an inner circumferential surface of the cap. The apparatus may be an apparatus for measuring brain waves.

The main body of the apparatus may be coupled to a glasses leg. For example, the main body may include a housing having a long bar shape and having a width and a size similar to those of the glasses leg, and may be coupled to a top surface or a side surface of the glasses leg. The apparatus may further include an attachment/detachment coupler configured to detachably couple the main body to the glasses leg. The attachment/detachment coupler may be any one of a clip-type attachment/detachment device including a clip for detachably fixing the main body to the glasses leg, an insertion-type attachment/detachment device having a groove and including an elastic material and into which a part of the glasses leg is fixedly inserted, and a Velcro-type attachment/detachment device including a Velcro tape for surrounding and fixing a part of the glasses leg. The apparatus may further include a connection frame configured to support the sensor support, connected to the main body, and configured to allow the sensor electrode (or the sensor module) to contact the head of the living body. The connection frame may include an elastic material so that the sensor electrode (or the sensor module) is elastically pressed to the scalp of the living body. The sensor electrode (or the sensor module) may be provided on an inner surface of the main body that contacts the head of the living body when the main body is worn on the glasses leg, without the connection frame. The apparatus may be an apparatus for measuring brain waves.

The apparatus may further comprise two main frames corresponding to respective ears of a head of the living body when being worn on the head of the living body; a plurality of connection frames configured to support the sensor electrode, extend from the two main frames, and configured to allow the sensor electrode to contact the head of the living body when being worn on the head of the living body; and an auxiliary frame configured to elastically connect the two main frames and to fix the two main frames to the head of the living body when being worn on the head of the living body, wherein the main body is provided on at least one of the two main frames.

The plurality of connection frames and the auxiliary frame may be fixedly coupled to the main frames. The main body may be provided on at least one of the one pair of main frames. The connection frames may include an elastic material to be elastically pressed to the scalp of the living body. The apparatus may further include at least one of a reference electrode and a ground electrode. The reference electrode and/or the ground electrode may be provided under the one pair of main frames to be located behind the ears of the living body when the apparatus is worn on the living body. A sensor support configured to connect the reference electrode and/or the ground electrode to the main frames may be provided. The sensor support may elastically support the reference electrode or the ground electrode so that the reference electrode or the ground electrode moves in 3-axis directions. For example, the sensor support may include a spiral spring, the reference electrode or the ground electrode may be coupled to one inner end of the spiral spring, and an outer surface of the spiral spring may be supported by the main frames. The apparatus may be an apparatus for measuring brain waves.

The apparatus may further comprise an attachment/detachment coupler configured to detachably couple the main body to a headphone. For example, the main body may include a housing having a flat shape, and the attachment/detachment coupler may be attached/detached to/from a lower end of a headband of the headphone. The main body may be fixedly coupled to the headphone. Alternatively, the apparatus may further include a connection frame configured to support the sensor support, extending from the main body, and configured to allow the sensor electrode to contact the head of the living body when the headphone is worn on the head of the living body. One end of the connection frame may be connected by using a string to the headphone. The apparatus may be an apparatus for measuring brain waves.

The main body of the apparatus may be integrally formed with a headband of a headphone and/or a housing in which a driver for outputting a sound is received. For example, when the main body is integrally formed with the headband, the sensor support may include a spiral spring configured to connect a surface of the headband that contacts the head and the sensor module and to elastically support the sensor electrode (or the sensor module) so that the sensor electrode (or the sensor module) moves in 3-axis directions. Alternatively, the apparatus may further include a connection frame configured to support the sensor support, extending from the main body, and configured to allow the sensor electrode (or the sensor module) to contact the head of the living body when the headphone is worn on the head of the living body. For example, the connection frame may extend from the housing in which the driver for outputting a sound is received and may allow the sensor electrode (or the sensor module) to contact the forehead of the living body.

The apparatus may be worn on a wrist. For example, the apparatus may include a band worn on the wrist. The apparatus may have a wristwatch shape. The main body of the apparatus may be provided on a watch portion of the wristwatch shape. The sensor electrode (or the sensor module) may be provided on an inner surface of the main body. Also, a concave space may be formed in the inner surface of the main body and a sensor support configured to elastically support the sensor electrode (or the sensor module) may be located.

A main circuit for processing bioelectrical signals obtained by the sensor module may be embedded in the main body. The main circuit may include a controller configured to determine a state of a user based on the bioelectrical signals obtained by the sensor module and to control the sensor module and a signal processor. Also, the main circuit may include a memory configured to store at least one of the bioelectrical signals obtained by the sensor module and information about the state of the user determined by the controller. The main circuit may further include an output device configured to express information about the living body generated by the controller. The output device may be a speaker, a lamp, or a display. The main circuit may include a battery or an energy harvest module. The main circuit may include an input/output port configured to output information about bioelectrical signals or to receive a control signal. The main circuit may include at least one communication module of a wired communication module and a wireless communication module that communicate with an external electronic device, may transmit at least one of the bioelectrical signals obtained by the sensor module and the information about the state of the user determined by the controller to the external electronic device, and may receive a control signal from the external electronic device.

For example, the state of the user determined by the controller may include an emergency. In other words, the controller may predict or determine an emergency from the bioelectrical signals obtained by the sensor module. When the user is in an emergency, the controller may transmit information about the emergency of the user to an external device or may output an alarm.

The main body may have any one of an earset shape, an earphone shape, a cap shape, a hair band shape, a glasses shape, a wristwatch shape, a bracelet shape, a forearm band shape, and an eye bandage shape.

According to an aspect of another exemplary embodiment, an apparatus for measuring bioelectrical signals includes: a sensor module including a sensor electrode including a tapering portion that narrows toward one end and a protruding portion that extends from the one end of the tapering portion, contacts a body part, and senses bioelectrical signals; and a main body connected to the sensor module and being wearable on a living body. The protruding portion may include a flexible material.

According to an aspect of another exemplary embodiment, an apparatus for measuring bioelectrical signals includes: a sensor electrode contacting a living body and configured to detect bioelectrical signals; a sensor support configured to elastically support the sensor electrode so that the sensor electrode moves in 3-axis directions; and a main body connected to the sensor support and being wearable on the living body. The sensor support may include a spiral spring, and the sensor electrode may be coupled to one of two ends of the spiral spring. A surface on which the one end of the spiral spring is placed may protrude beyond a surface on which the other end of the spiral spring is placed. The sensor support may include an edge support spaced apart by a predetermined interval from the sensor module and surrounding an outer surface of the sensor module, and at least two springs configured to connect the sensor module and the edge support. A cable configured to transmit bioelectrical signals measured by the sensor module or to supply power to the sensor module may be located outside the sensor support. If necessary, the cable may be buried in the sensor support.

According to an aspect of another exemplary embodiment, an apparatus for measuring bioelectrical signals includes: a sensor module including a sensor electrode for measuring bioelectrical signals; a main body on which the sensor module is provided and having an earset shape worn on an ear of a living body; and a connection frame configured to support the sensor module, connected to a main body, and configured to allow the sensor electrode for measuring bioelectrical signals to contact the head of the living body. The main body may include a slot, and one end of the connection frame may be detachably inserted into the slot. A plurality of the slots may be formed so that a plurality of the connection frames extend from the head of the living body in different directions to different positions on the head of the living body. The apparatus may further include an ear connection ring configured to fix the main body to the auricle of the ear of the living body. The ear connection ring may be elastically connected to the main body. The apparatus may further include an ear insertion ring inserted into an external part of the ear of the living body. A reference electrode or a ground electrode may be provided on the ear insertion ring. The ear insertion ring may be formed by extending from the ear connection ring. Alternatively, a sensor support configured to connect the ear connection ring and the ear insertion ring and to elastically support the ear insertion ring so that the ear insertion ring moves in 3-axis directions may be provided. In this case, the sensor support may include a spiral spring, one inner end of the spiral spring may be supported by the ear connection ring, and the ear insertion ring may be coupled to an outer end portion of the spiral spring. The apparatus may further include an auxiliary frame configured to fix the main body to the head of the living body. The auxiliary frame may have a hair band shape, a cap shape, or a headband shape. The auxiliary frame may be detachably coupled to the main body. One pair of main bodies may be worn on the left ear and the right ear of the living body.

According to an aspect of another exemplary embodiment, an apparatus for measuring bioelectrical signals includes: a sensor module including a sensor electrode for measuring bioelectrical signals; and a main body on which the sensor module is provided and coupled to a glasses leg. An attachment/detachment coupler configured to detachably couple the main body to the glasses leg may be further provided. The attachment/detachment coupler may be any one of a clip-type attachment/detachment device including a clip for detachably fixing the main body to the glasses leg, an insertion-type attachment/detachment device having a groove and including an elastic material and into which a part of the glasses leg is fixedly inserted, and a Velcro-type attachment/detachment device including a Velcro tape for surrounding and fixing a part of the glasses leg. The apparatus may further include a connection frame configured to support the sensor support, connected to the main body, and configured to allow the sensor electrode to contact the head of a living body. The connection frame may include an elastic material so that the sensor electrode is elastically pressed to the scalp of the living body. The sensor electrode may be provided on an inner surface of the main body that contacts the head of the living body when the main body is worn on the glasses leg, without the connection frame.

According to an aspect of another exemplary embodiment, an apparatus for measuring bioelectrical signals includes: a sensor module including a sensor electrode for measuring bioelectrical signals; and a frame on which the sensor module is provided and worn on a living body, wherein the frame includes one pair of main frames located over both ears of the head of the living body when the frame is worn on the head of the living body, a plurality of connection frames configured to support the sensor module for measuring bioelectrical signals, extending from the one pair of main frames, and configured to allow the sensor electrode for measuring bioelectrical signals to contact the head of the living body, and an auxiliary frame having a hair band shape and configured to fix the one pair of main frames to the head of the living body. The apparatus may further include a reference electrode or a ground electrode provided on the main frames to be located behind the ear of the living body when the sensor module and the frame are worn on the living body. A main body may be provided on at least one of the one pair of main frames. In other words, a main circuit may be provided in at least one of the one pair of the main frames. The apparatus may further include a sensor support configured to connect the reference electrode or the ground electrode to the main frames and to elastically support the reference electrode or the ground electrode so that the reference electrode or the ground electrode moves in 3-axis directions. The sensor support may include a spiral spring that is rolled into a spiral shape, the reference electrode or the ground electrode may be coupled to one inner end of the spiral spring, and an outer surface of the spiral spring may be supported by the main frames.

According to an aspect of another exemplary embodiment, an apparatus for measuring bioelectrical signals includes: a sensor holder inserted into an external part of an ear of a living body and having an earphone shape; and a sensor electrode provided on the sensor holder to contact the external part of the ear of the living body and configured to detect bioelectrical signals. The apparatus may further include a body extending from the sensor holder and exposed to the auricle of the ear of the living body. The sensor holder and the body may be integrally formed with each other or the sensor holder may be fixed to the body. Alternatively, a sensor support configured to elastically support the sensor module so that the sensor module moves in 3-axis directions may be provided between the sensor holder and the body. The sensor support may include a spiral spring that is rolled into a spiral shape, one inner end of the spiral spring may be supported by the body, and the sensor holder may be coupled to an outer end portion of the spiral spring. A sensor circuit configured to process bioelectrical signals detected by the sensor electrode may be provided. The sensor circuit may be embedded in the sensor holder or the body that supports the sensor holder.

According to an aspect of another exemplary embodiment, an apparatus for measuring bioelectrical signals includes: a sensor module including a sensor electrode for measuring bioelectrical signals; and a main body on which the sensor module is provided and worn on a living body, wherein the main body has a circular band shape or a semicircular band shape coupled to an inner surface of a cap. The sensor electrode may be provided on at least one portion of an inner surface of the main body that contacts the living body when the cap is worn on the head of the living body and may contact the head of the living body when the cap is worn on the head of the living body. Also, the apparatus may further include a connection frame configured to support the sensor electrode, extending from the main body, and configured to allow the sensor electrode to contact the head of the living body when the cap is worn on the head of the living body. Furthermore, the apparatus may further include an attachment/detachment coupler configured to detachably couple the main body to an inner circumferential surface of the cap. The apparatus may be an apparatus for measuring brain waves.

According to an aspect of another exemplary embodiment, an apparatus for measuring bioelectrical signals includes: a sensor module including a sensor electrode for measuring bioelectrical signals; a main body on which the sensor module is provided and coupled to a lower end of a headband of a headphone; and a connection frame configured to support the sensor module, extending from the main body, and configured to allow the sensor electrode to contact the head of a living body when the headphone is worn on the head of the living body. Furthermore, the apparatus may further include an attachment/detachment coupler configured to detachably couple the main body to the lower end of the headband. The main body may be fixedly coupled to the lower end of the headband of the headphone. One end of the connection frame may be connected by using a string to the headphone. The apparatus may be an apparatus for measuring brain waves.

According to an aspect of another exemplary embodiment, an apparatus for measuring bioelectrical signals includes: a sensor module including a sensor electrode for measuring bioelectrical signals; and a band on which the sensor module is provided and worn on a wrist of a living body. The sensor module may include the sensor electrode for measuring bioelectrical signals, and a reference electrode and a ground electrode. The apparatus may have a wristwatch shape. In this case, the sensor module may be provided on at least one of a surface of a watch portion (that is, a main body) of the wristwatch shape that contacts the wrist of the living body, a surface of the band that contacts the wrist of the living body, and a surface of a coupling portion of the band that contacts the wrist of the living body. Also, a main circuit may be provided in the watch portion (that is, the main body) of the wristwatch shape. In this case, the sensor module may measure electromyogram (EMG) signals.

According an aspect of another exemplary embodiment, a sensor electrode for measuring bioelectrical signals includes: a tapering portion narrowing toward one end; and a protruding portion extending from the one end of the tapering portion to contact a body part and configured to sense bioelectrical signals. Regarding longitudinal sections of the tapering portion and the protruding portion along a bottom surface of the other end of the tapering portion, a gradient of an outer circumferential surface of the protruding portion may be greater than a gradient of an outer circumferential surface of the tapering portion. The protruding portion may include a flexible material.

According to an aspect of another exemplary embodiment, a sensor module for measuring bioelectrical signals includes: an electrode supporter; and a sensor electrode provided on the electrode supporter and including a tapering portion that narrows toward one end and a protruding portion that extends from the one end of the tapering portion, contacts a body part, and senses bioelectrical signals. Regarding longitudinal sections of the tapering portion and the protruding portion along a mount surface of the electrode supporter on which the sensor electrode is mounted, that is, a bottom surface of the other end of the tapering portion, a gradient of an outer circumferential surface of the protruding portion may be greater than a gradient of an outer circumferential surface of the tapering portion. The protruding portion may include a flexible material. The sensor electrode may be a dry electrode. For example, the sensor electrode may include a conductive polymer. The conductive polymer may be conductive silicone or conductive rubber. The tapering portion and the protruding portion of the sensor electrode may be integrally formed with each other. The tapering portion may have a cone shape having a streamlined cross-section. The protruding portion may have any one of a cylindrical shape, an elliptic cylindrical shape, and a prism shape. One end of the protruding portion may have a blunt shape such as a hemispheric shape and may minimize pain in a living body when the protruding portion contacts the living body. An outer surface of the tapering portion and an outer surface of the protruding portion may be connected to have a gently curved surface. For example, the outer surface of the tapering portion and the outer surface of the protruding portion may be connected to have a curved surface that is concave inward. In other words, regarding the longitudinal sections of the tapering portion and the protruding portion along the bottom surface of the tapering portion of the sensor electrode, the tapering portion and the protruding portion may be shaped so that the gradients of the outer circumferential surface of the tapering portion and the outer circumferential surface of the protruding portion increase upward. One end of the protruding portion may have a blunt shape such as a hemispheric shape. The electrode supporter may have a circular plate shape, a quadrangular plate shape, or a long bar shape. When the sensor module measures brain waves, the electrode supporter may be bent to conform to the head of the living body. A plurality of the sensor electrodes may be provided on the electrode supporter. When the electrode supporter has a long bar shape, the sensor electrodes may be arranged in one or more columns in a longitudinal direction. When the tapering portions of the sensor electrodes have elliptic cone shapes, the sensor electrodes may be arranged so that long axes of cross-sections of the tapering portions are parallel or perpendicular to directions of the one or more columns. Alternatively, when the cross-sections of the tapering portions of the sensor electrodes have streamlined shapes, measuring electrodes may be arranged so that longitudinal directions of the cross-sections of the tapering portions are parallel or perpendicular to the directions of the one or more columns. Alternatively, only one sensor electrode may be provided on the electrode supporter. The electrode supporter may include a hard or soft non-conductive material. In this case, an electrode for electrically connecting the sensor electrode may be provided on a rear surface or a surface of the electrode supporter that supports the sensor electrode. Furthermore, a sensor circuit may be located on the rear surface of the electrode supporter or inside the electrode supporter. The sensor circuit may include an analog amplification circuit that amplifies bioelectrical signals detected by the sensor electrode. Furthermore, the sensor circuit may further include an analog-digital conversion circuit configured to convert analog signals amplified by the analog amplification circuit into digital signals. Also, the sensor circuit may further include a wired communication module or a wireless communication module configured to transmit bioelectrical signals detected by the sensor electrode to the outside. The sensor circuit may further include at least one of a battery, a wireless power module, and an energy harvest module. A cable configured to electrically connect the sensor circuit to an external electronic device may be further provided. The cable may include at least one of a power line that supplies power to the sensor circuit, a bioelectrical signal line that transmits bioelectrical signals detected by the sensor electrode, a reference signal line, and a ground signal line. The electrode supporter may include a conductive material. In this case, the electrode supporter may be electrically connected to the sensor electrode. Examples of bioelectrical signals measured by the sensor electrode may include brain waves, ECG signals, EMG signals, ENG signals, and EOG signals.

According to an aspect of another exemplary embodiment, a sensor module for measuring bioelectrical signals includes: an electrode supporter; and a sensor electrode provided on the electrode supporter, wherein the sensor electrode has an elliptic cone shape having an elliptic cross-section or a streamlined pyramid shape having a streamlined cross-section. The sensor electrode may include a flexible material. A plurality of the sensor electrode may be arranged in one or more columns on the electrode supporter. The sensor electrodes are located so that long axes or longitudinal directions of cross-sections are parallel or perpendicular to directions of the one or more columns.

According to an aspect of another exemplary embodiment, a sensor support structure includes: a sensor mount portion configured to support a sensor electrode (or a sensor module) that contacts a living body and detects bioelectrical signals to maintain the contact between the sensor electrode (or the sensor module) and a body part and to which the sensor electrode (or the sensor module) is attached; and a sensor support having one end on which the sensor mount portion is provided and configured to elastically support the sensor module so that the sensor module moves in 3-axis directions. An elastic support may include a spiral spring, and the sensor mount portion may be provided on one of two ends of the spiral spring. The sensor mount portion may protrude with respect to the spiral spring along a central axis of a spiral shape of the spiral spring. The sensor support may include the spiral spring, and the sensor module may be coupled to one of two ends of the spiral spring. A surface on which the one end of the spiral spring is placed may protrude beyond a surface on which the other end of the spiral spring is placed. An elasticity of the spiral spring along the central axis of the spiral spring may be greater than an elasticity of the spiral spring in a direction perpendicular to the central axis of the spiral spring. At least a part of an outer surface of a connection portion between a connection frame and the spiral spring of the sensor support may have a linear or gently curved shape. For example, the outer surface of the connection portion between the connection frame and the spiral spring may have a predetermined curvature. The sensor support may include an edge support having a ring shape that surrounds an outer surface of the spiral spring and an outer end of the spiral spring may be attached to the edge support. A connection portion between the connection frame and the edge support may have an outer surface having a gently curved shape. The spiral spring may have a circular, elliptic, or atypical spiral shape. The sensor support may include a first edge support that is spaced apart by a predetermined interval from the sensor electrode (or the sensor module) and surrounds an outer surface of the sensor electrode (or the sensor module) and at least two first springs that connect the sensor electrode (or the sensor module) and the first edge support. The sensor support may include a second edge support that is spaced apart by a predetermined interval from the first edge support and surrounds the first edge support and at least two second springs that connect the first and second edge supports. The sensor support may include plastic or a metal. A cable that transmits bioelectrical signals measured by the sensor electrode or supplies power to the sensor electrode may be located outside the sensor support. If necessary, the cable may be buried in the sensor support. The sensor mount portion and the electrode supporter of the sensor module may be integrally formed with each other and may not be mechanically separated from each other. For example, the sensor mount portion (or the electrode supporter) may have a cylindrical shape inserted into an external part of an ear of the living body, and the sensor electrode may be provided on an outer circumferential surface of the sensor mount portion to contact the skin of the living body when the sensor mount portion (or the electrode supporter) is inserted into the external part of the ear of the living body.

According to another aspect of an exemplary embodiment, there is provided an apparatus for measuring bioelectrical signals, the apparatus comprising a sensor module comprising a sensor electrode that senses bioelectrical signals, wherein the sensor electrode comprises a tapering portion that narrows toward one end and a protruding portion that extends from the one end of the tapering portion and contacts a body part, and senses bioelectrical signals; a communication circuit that communicates with an external device; an output circuit that outputs an alarm; and a controller that determines an emergency level of a user based on bioelectrical signals sensed by the sensor module, and controls the output circuit to output an alarm corresponding to the determined emergency level through the output circuit or controls the communication circuit to transmit information about the determined emergency level to the external device through the communication circuit.

According to an aspect of another exemplary embodiment, an apparatus for measuring bioelectrical signals includes: a sensor module including a sensor electrode for sensing bioelectrical signals, the sensor electrode including a tapering portion that narrows toward one end and a protruding portion that extends from the one end of the tapering portion, contacts a body part, and senses bioelectrical signals; and a circuit including a communication circuit that communicates with an external device, an output device that outputs an alarm, and a controller that determines an emergency level of a user based on bioelectrical signals sensed by the sensor module and controls the output device to output an alarm through the output device or controls the communication circuit to transmit information about the determined emergency level to the external device through the communication circuit according to the determined emergency level.

The apparatus may further comprise a memory that stores a risk evaluation model for evaluating a first risk level and a second risk level from bioelectrical signals, the second risk level being higher than the first risk level, wherein the controller controls the output circuit to output an alarm through the output circuit when the emergency level of the user corresponds to the first risk level and controls the communication circuit to transmit information about the emergency level of the user to the external device through the communication circuit when the emergency level of the user corresponds to the second risk level. If necessary, the controller may control the output device to output an alarm when the emergency level of the user is included in the second risk level and may control the communication circuit to transmit information about the emergency of the user to the external device when the emergency level of the user is included in the first risk level.

The emergency level of the user may include a first risk level that is relatively low and a second risk level that is relatively high, and the controller may control the communication circuit to transmit bioelectrical signals received from the apparatus to a computer device and to receive information about the emergency level of the user that is generated by processing the bioelectrical signals from the computer device through the communication circuit, and may control the output device to output an alarm through the output device when the emergency level of the user received from the computer device is included in the first risk level and may control the communication circuit to transmit the information about the emergency level of the user to the external device through the communication circuit when the emergency level of the user received from the computer device is included in the second risk level. If necessary, the controller may control the output device to output an alarm when the emergency level of the user received from the computer device is included in the second risk level and may control the communication circuit to transmit information about the emergency of the user to the external device when the emergency level of the user received from the computer device is included in the first risk level.

According to an aspect of another exemplary embodiment, a system for processing bioelectrical signals includes: the apparatus for measuring bioelectrical signals; and an apparatus for processing bioelectrical signals that receives bioelectrical signals from the apparatus for measuring bioelectrical signals and processes the bioelectrical signals.

According to another aspect of an exemplary embodiment, there is provided a mobile device for receiving bioelectrical signals from an apparatus for measuring bioelectrical signals, the apparatus comprising: a sensor electrode comprising a tapering portion that narrows toward one end and a protruding portion that extends from the one end of the tapering portion and contacts a body part, and senses bioelectrical signals; a sensor support configured to support the sensor electrode to maintain the contact between the sensor electrode and the body part; and a main body connected to the sensor support and being wearable on a living body, the mobile device comprising a communication circuit configured to communicate with the apparatus and an external device; an output circuit configured to output an alarm; and a controller configured to determine an emergency level of a user based on bioelectrical signals received from the apparatus and to control the output circuit to output an alarm corresponding to the determined emergency level through the output circuit or to control the communication circuit to transmit information about the determined emergency level to the external device through the communication circuit. The mobile device may further comprise a memory configured to store a risk evaluation model for evaluating a first risk level and a second risk level from bioelectrical signals, the second risk level being higher than the first risk level, wherein the controller controls the output circuit to output an alarm through the output circuit when the emergency level of the user corresponds to the first risk level and controls the communication circuit to transmit information about the emergency level of the user to the external device through the communication circuit when the emergency level of the user corresponds to the second risk level. If necessary, the controller may control the output device to output an alarm through the output device when the emergency level of the user is included in the second risk level and may control the communication circuit to transmit information about the emergency level of the user to the external device through the communication circuit when the emergency level of the user is included in the first risk level.

The emergency level of the user may comprise a first risk level, and a second risk level that is higher than the first risk level, wherein the controller controls the communication circuit to transmit bioelectrical signals received from the apparatus to a computer device and to receive information about the emergency level of the user that is generated by processing the bioelectrical signals from the computer device through the communication circuit, controls the output circuit to output an alarm through the output circuit when the emergency level of the user received from the computer device is equal to or greater than the first risk level and less than the second risk level, and controls the communication circuit to transmit information about the emergency level of the user to the external device through the communication circuit when the emergency level of the user received from the computer device is greater than or equal to the second risk level.

The mobile device may include: a communication circuit configured to communicate with the apparatus for measuring bioelectrical signals and a computer device; an output device configured to output an alarm; and a controller configured to transmit bioelectrical signals received from the apparatus for measuring bioelectrical signals to the computer device, to receive information about a state of a user generated by processing the bioelectrical signals from the computer device, and to control the output device and the communication circuit based on the received information about the state of the user For example, the computer device may process the bioelectrical signals and may generate information about an emergency level of the user. For example, the emergency level of the user may include a first risk level that is relatively low and a second risk level that is relatively high. The controller of the mobile device may transmit bioelectrical signals received from the apparatus for measuring bioelectrical signals to the computer device through the communication circuit, may receive the information about the emergency level of the user generated by processing the bioelectrical signals from the computer device, and may control the output device to output an alarm through the output device when the emergency level of the user received from the computer device is included in the first risk level and may control the communication circuit to transmit information about the emergency of the user to an external device through the communication circuit when the emergency level of the user received from the computer device is included in the second risk level. The computer device and the external device may be the same or different from each other. For example, the computer device may be a server of a remote medical service provider and the external device may be a server of an emergency center, a server of a hospital to which the user usually goes, a phone of a doctor in charge of the user, or a phone of a guardian for the user. The information about the emergency of the user may be transmitted to the external device directly by the communication circuit of the mobile device, may be controlled by the computer device to be transmitted to the external device, or may be automatically transmitted by the computer device to the external device according to a scenario that is stored in the memory.

Examples of the mobile device may include a mobile phone, a smart phone, a tablet computer, a personal digital assistant (PDA), and a laptop computer. The mobile device may transmit information of processed bioelectrical signals to a computer device that is connected through a network. Also, the mobile device may include at least one of a location tracking sensor that tracks a position of a living body, an acceleration sensor that measures an acceleration of the living body, and a motion sensor that measures a movement of the living body, and may transmit information of at least one of the position and the movement of the living body to the computer device.

An apparatus for processing bioelectrical signals may include a computer device configured to communicate with an apparatus for measuring bioelectrical signals. The computer device may include: a communication circuit configured to directly communicate with the apparatus for measuring bioelectrical signals and to receive bioelectrical signals from the apparatus for measuring bioelectrical signals; a memory configured to store a risk evaluation module for evaluating a first risk level and a second risk level that is higher than the first risk level from brain wave signals; and a controller configured to control the output device to transmit an alarm message to the apparatus for measuring bioelectrical signals when an emergency level of a user is included in the first risk level and to control the communication information to transmit information about the emergency of the user to an external device when the emergency level of the user is included in the second risk level. The computer device may be a server of a remote medical service provider, a server of a hospital to which the user usually goes, or a personal computer in a house of the user. The external device may be a server of an emergency center, the server of the hospital to which the user usually goes, or a phone of a guardian for the user.

The output device configured to express information of bioelectrical signals processed by the apparatus for processing bioelectrical signals may be provided inside or outside the apparatus for measuring bioelectrical signals or the apparatus for processing bioelectrical signals. Examples of the output device may include a speaker, a vibration module, a lamp, and a display. For example, the apparatus for measuring bioelectrical signals may include a vibration module and may output an alarm by using a vibration method. Alternatively, the mobile device may include a speaker, a vibration module, and a display, and may output an alarm by using an alarm sound, a vibration, or a warning message.

The controller of the apparatus for processing bioelectrical signals may include at least one of an emergency prediction module configured to predict or determine an emergency from information of bioelectrical signals and a living body intention inference module configured to infer an intention of the living body from the bioelectrical signals.

For example, the apparatus for processing bioelectrical signals may predict or determine an emergency from information of bioelectrical signals and may transmit an alarm to an output device when the emergency is predicted or determined, and the output device may output an alarm. The bioelectrical signals may be at least one of brain waves, ECG signals, EMG signals, ENG signals, and EOG signals, and the apparatus for processing bioelectrical signal may infer the intention or state of the living body from the bioelectrical signals.

Alternatively, the controller of the apparatus for processing bioelectrical signals may transmit information about the inferred intension or state to the output device, and the output device may output the information about the inferred intention or state. The apparatus for processing bioelectrical signals may generate control information according to the information about the inferred intention or state and may transmit the control information to an electronic device.

The apparatus for measuring bioelectrical signals may further include a measuring sensor configured to measure at least one of a body temperature, a heart rate, a nodding event, an eye-blinking event, and a tossing event. At least one of a location tracking sensor for tracking a position of the living body, an acceleration sensor for measuring an acceleration of the living body, and a motion sensor for measuring a movement of the living body may be further provided. Such an additional sensor may be provided in the apparatus for measuring bioelectrical signals or an additional electronic device.

According to an aspect of another exemplary embodiment, a method of processing bioelectrical signals includes: measuring bioelectrical signals of a living body from the apparatus for measuring bioelectrical signals; and generating information about the living body by processing the measured bioelectrical signals.

The method may further include predicting or determining an emergency from the information about the living body and outputting an alarm to a user when the emergency is predicted or determined.

The measuring of the bioelectrical signals of the living body may include measuring at least one of brain waves, ECG signals, EMG signals, ENG signals, and EOG signals of the living body. The generating of the information about the living body may include inferring an intention or a state of the living body from the bioelectrical signals. The measuring of the bioelectrical signals of the living body may further include measuring at least one of a body temperature, a heart rate, a nodding event, an eye-blinking event, and a tossing event of the living body. The method may further include transmitting information about the inferred intention or state of the living body to the user.

The method may further include tracking a position of the living body, and information transmitted to the user may include position information of the living body.

The user may be at least one of the living body, a guardian for the living body, and a health care provider.

The apparatus for measuring bioelectrical signals, the sensor electrode for an apparatus for measuring bioelectrical signals, the sensor support structure, and the system for measuring bioelectrical signals according to the one or more exemplary embodiments may prevent noise from occurring when a living body moves.

The sensor electrode for measuring bioelectrical signals according to the one or more exemplary embodiments may easily reach a surface of the living body by easily passing through obstructions such as hairs.

The sensor electrode for measuring bioelectrical signals according to the one or more exemplary embodiment may improve the quality of signals by increasing a contact area of the sensor electrode.

The apparatus for measuring bioelectrical signals according to the one or more exemplary embodiments may be customized by being modified in various ways.

According to another aspect of an exemplary embodiment, there is provided an apparatus for measuring bioelectrical signals, the apparatus comprising a sensor electrode comprising a first portion that tapers to a second portion that protrudes from the first portion, the sensor electrode sensing bioelectrical signals; a main body that is wearable on a living body; and an elastic support that is connected to the main body and to the sensor electrode and that elastically maintains contact between the second portion of the sensor electrode and the living body.

The second portion of the sensor electrode may be flexible, and the elastic support may elastically press the second portion of the sensor electrode against the living body.

As a pressure exerted by the elastic support increases, the second portion may be deformed such that a surface area of the second portion that contacts the living body increases.

The elastic support may elastically support the sensor electrode so that the sensor electrode moves in 3-axis directions.

The elastic support may comprise a spiral spring, and the sensor electrode may be coupled to one of two ends of the spiral spring.

The two ends of the spiral spring may be located on different planes, which are separated from one another.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
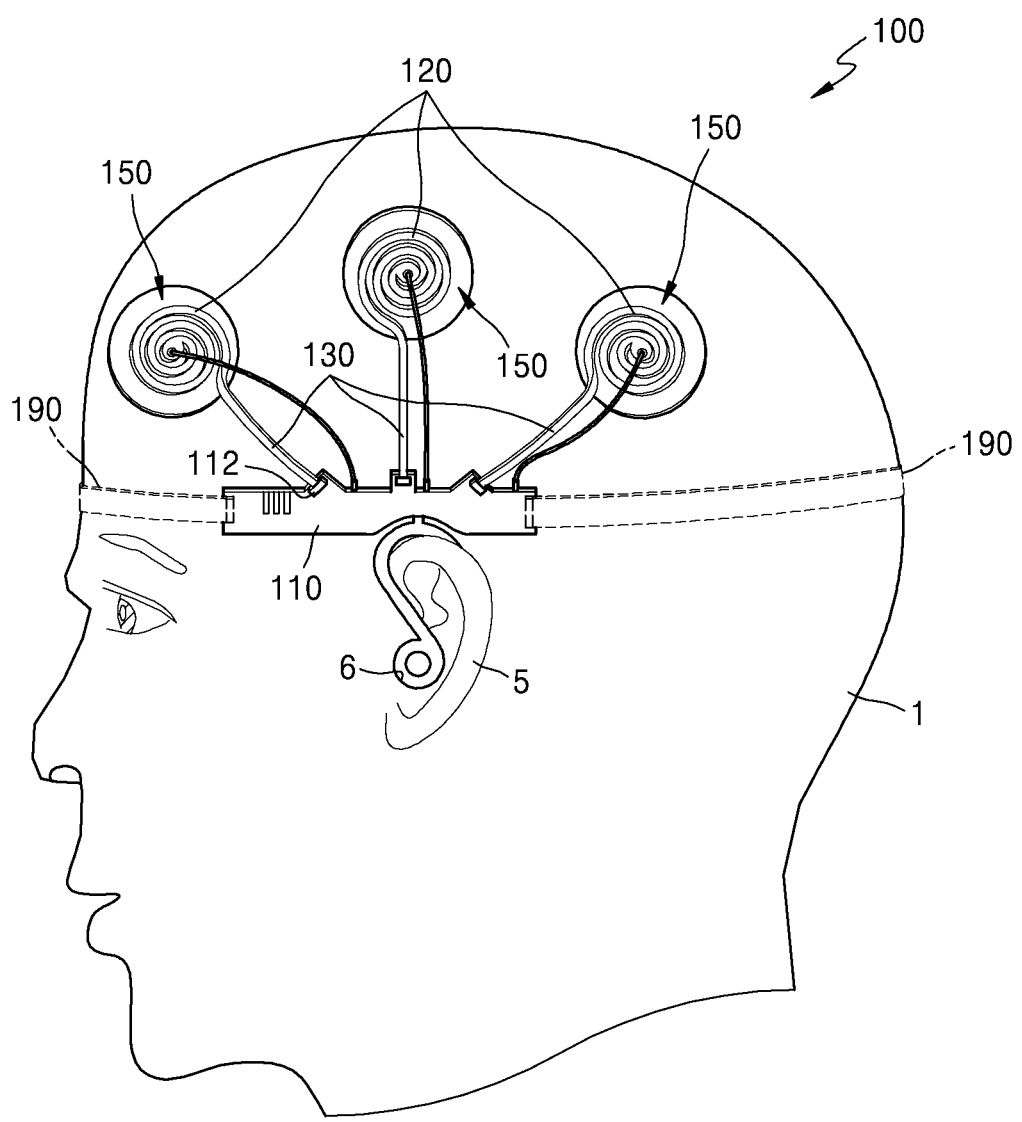
FIG. 1 is a view of an apparatus for measuring bioelectrical signals, according to an exemplary embodiment.

The advantages and features of the inventive concept and methods of achieving the advantages and features will be described more fully with reference to the accompanying drawings, in which exemplary embodiments of the inventive concept are shown. The inventive concept may, however, be embodied in many different forms and should not be construed as being limited to the exemplary embodiments set forth herein; rather these exemplary embodiments are provided so that this disclosure will be thorough and complete, and will fully convey the concept of the inventive concept to one of ordinary skill in the art. In the drawings, the same reference numerals denote the same elements, and sizes or thicknesses of elements may be exaggerated for clarity.

Terms used herein will be explained in brief and the inventive concept will be explained in detail.

Most of the terms used herein are general terms that have been widely used in the technical art to which the inventive concept pertains. However, some of the terms used herein may be created reflecting intentions of technicians in this art, precedents, or new technologies. Also, some of the terms used herein may be specifically chosen by the present applicant. In this case, these terms are defined in detail below. Accordingly, the specific terms used herein should be understood based on the unique meanings thereof and the whole context of the inventive concept.

Throughout the present application, when a part "includes" or "comprises" an element, it is to be understood that the part additionally includes other elements rather than excluding other elements as long as there is no particular opposing recitation. Also, the terms such as " . . . unit", "module", or the like used in the present application indicate a unit, which processes at least one function or motion, and the "unit", "module", or the like may be implemented by hardware or software, or by a combination of hardware and software. The exemplary embodiments will now be described more fully with reference to the accompanying drawings for one of ordinary skill in the art to be able to make and use the inventive concept without any difficulty. Also, parts in the drawings unrelated to the detailed description are omitted to ensure clarity of the inventive concept.

As used herein, the term "and/or" includes any and all combinations of one or more of the associated listed items. Expressions such as "at least one of," when preceding a list of elements, modify the entire list of elements and do not modify the individual elements of the list.

Figure 2:
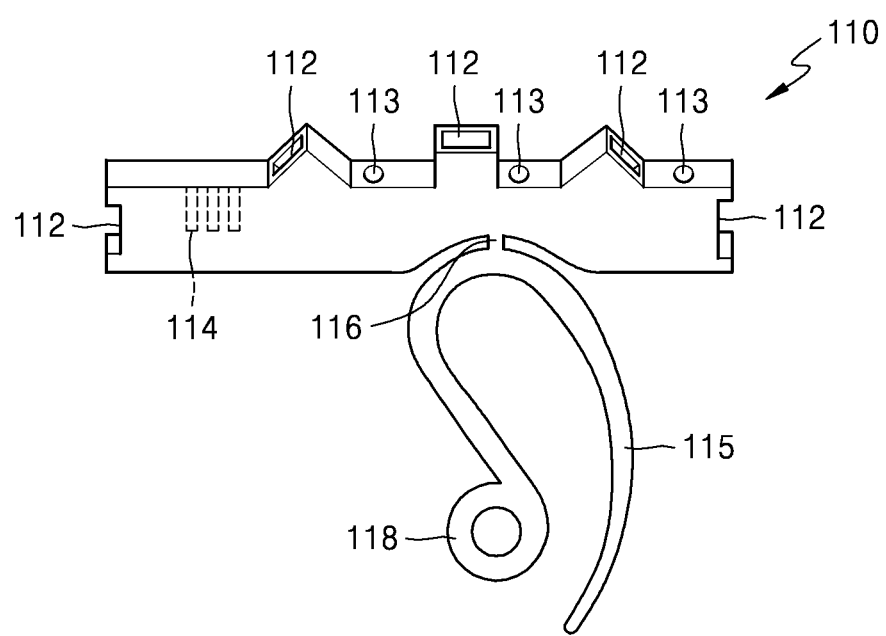
FIG. 2 is a view of a main body of the apparatus of FIG. 1.

FIG. 1 is a view of an apparatus 100 for measuring bioelectrical signals, according to an exemplary embodiment. FIG. 2 is a view of a main body 110 of the apparatus 100.

Referring to FIG. 1, the apparatus 100 of the present exemplary embodiment, which is worn on the head 1 of a living body to measure brain waves, may include the main body 110, a sensor module 150 that measures brain waves, a sensor support 120 that supports the sensor module 150, and a connection frame 130 that connects the sensor support 120 and the main body 110.

A main circuit 140 (see FIG. 16) for processing bioelectrical signals obtained by the sensor module 150 may be embedded in the main body 110. The main body 110 may include a housing in the form of an earset as shown in FIG. 2 and may be worn on an ear 5.

A slot 112 may be formed in the main body 110, and one end 131 (shown in FIG. 3) of the connection frame 130 may be detachably inserted into the slot 112. When the apparatus 100 is to measure brain waves, the brain waves may be measured at a specific position or a plurality of positions of the head 1. For example, a 10-20 system is well known as a standard method of describing positions of sensor electrodes to non-invasively measure brain waves. In order to implement a 10-20 system in the present exemplary embodiment, a plurality of the slots 112 may be formed so that a plurality of the connection frames 130 extend from the ear 5 in different directions to different positions on the head 1 as shown in FIG. 1. Also, a connector terminal 113 is provided on the main body 110. The connector terminal 113 may include a power connector terminal for supplying power to the sensor module 150 and a signal connector terminal for inputting/outputting electrical signals to/from the sensor module 150. The housing of the main body 110 may be formed of a plastic or a metal material.

An ear connection ring 115 fixed to the ear 5 may be provided on the main body 110. The ear connection ring 115 has a shape that surrounds an outer surface of the auricle and fits around the outer surface of the auricle to fix the main body 110 to the head 1. Furthermore, an ear insertion ring 118 that extends from the ear connection ring 115 may be further provided. The ear insertion ring 118 is inserted into an external part of the ear 5 of the head 1 to more stably fix the main body 110 to the head 1. A reference electrode 170

(shown in FIG. 14) or a ground electrode may be provided on the ear insertion ring 118 as described below. In other words, the ear insertion ring 118 may function as an electrode supporter for the reference electrode 170 or the ground electrode. The ear insertion ring 118 may be connected by an elastic bar 116 to the ear connection ring 115. Accordingly, the wearability of the apparatus 100 may be improved and the main body 110 may be more stably fixed to the head 1.

Referring back to FIG. 1, the connection frame 130 that supports the sensor module 150 has one end 131 (see FIG. 3) that is inserted into the slot 112 of the main body 110. The connection frame 130 may be formed of an elastic material such as plastic or metal, and may elastically press the sensor module 150 so that the sensor module 150 contacts the scalp when the apparatus 100 is worn on the head 1. For example, the connection frame 130 may be customized by using a three-dimensional (3D) printer. In this case, the connection frame 130 may be manufactured to have a length and a curvature suitable for a shape of the head of a user, and thus when the apparatus 100 is worn on the head 1, the sensor module 150 may be located at an accurate position on the head 1.

Brain waves may be measured at one or more positions on the head 1. Accordingly, one or more sensor modules 150 may be connected to the main body 110.

Figure 3:
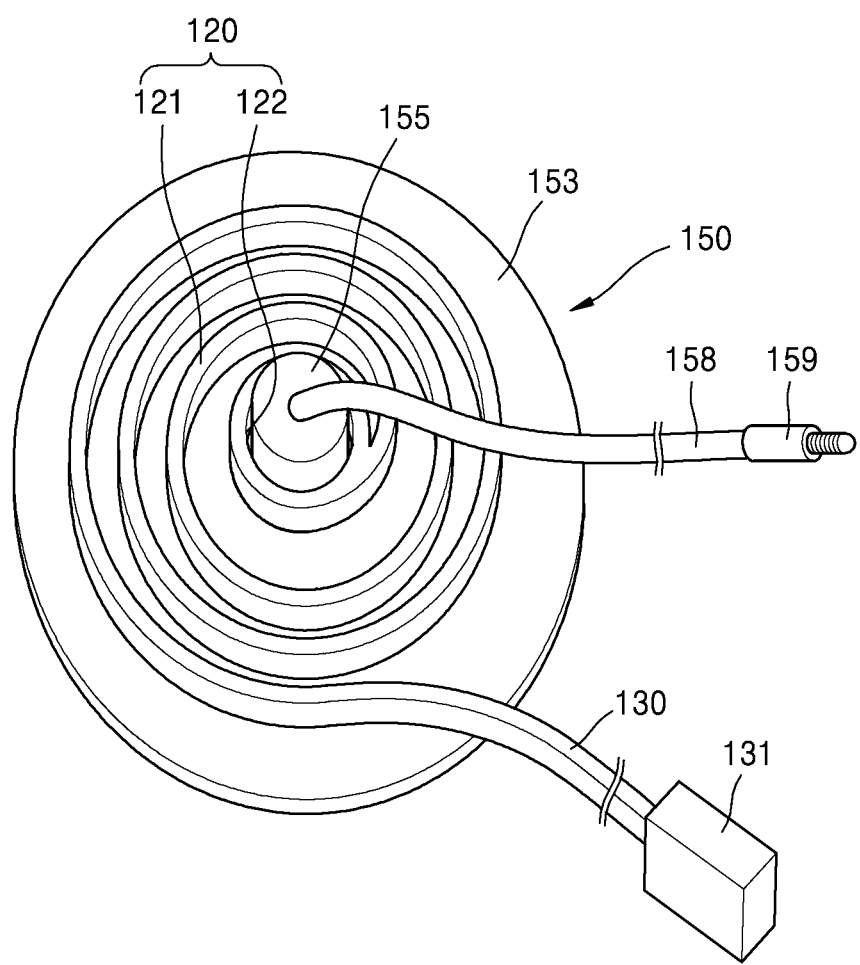
FIGS. 3 and 4 are views of a sensor support and a sensor module in the apparatus of FIG. 1.
Figure 4:
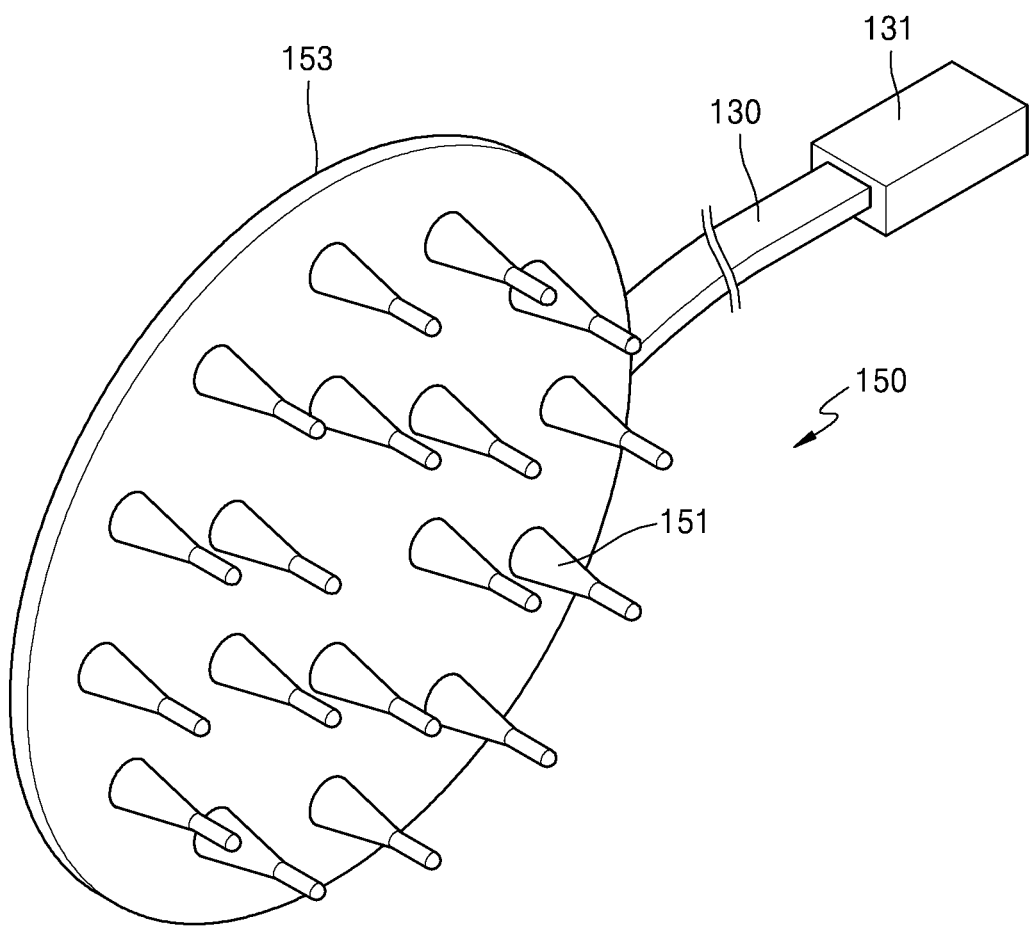

FIGS. 3 and 4 are views of the sensor support 120 and the sensor module 150, respectively. Referring to FIGS. 3 and 4, the sensor module 150 includes sensor electrodes 151, an electrode supporter 153 that supports the sensor electrodes 151, a coupling portion 155 that protrudes from a rear surface of the electrode supporter 153 and is coupled to the sensor support 120, and a cable 158 that transmits bioelectrical signals detected by the sensor electrodes 151. The rear surface of the electrode supporter 153 refers to a surface of the electrode supporter 153 that is opposite to a surface of the electrode supporter 153 on which the sensor electrodes 151 are provided. A terminal 159 of the cable 158 is inserted into the connector terminal 113 of the main body 110. The sensor module 150 is elastically supported by the sensor support 120. The sensor support 120 includes a spiral spring 121 and a sensor mount portion 122 into which the coupling portion 155 of the sensor module 150 is inserted.

The sensor electrodes 151 directly contact the scalp and detect bioelectrical signals. Bioelectrical signals detected by the sensor electrodes 151 may be brain wave signals generated in the head 1.

Figure 5:
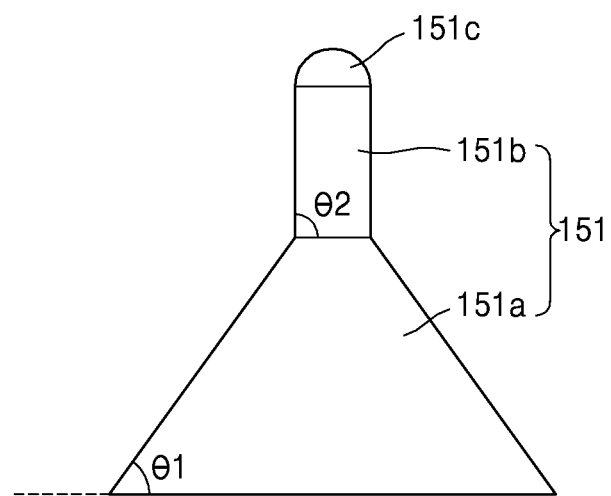
FIG. 5 is a side view of a sensor electrode of FIG. 4.
Figure 6A:
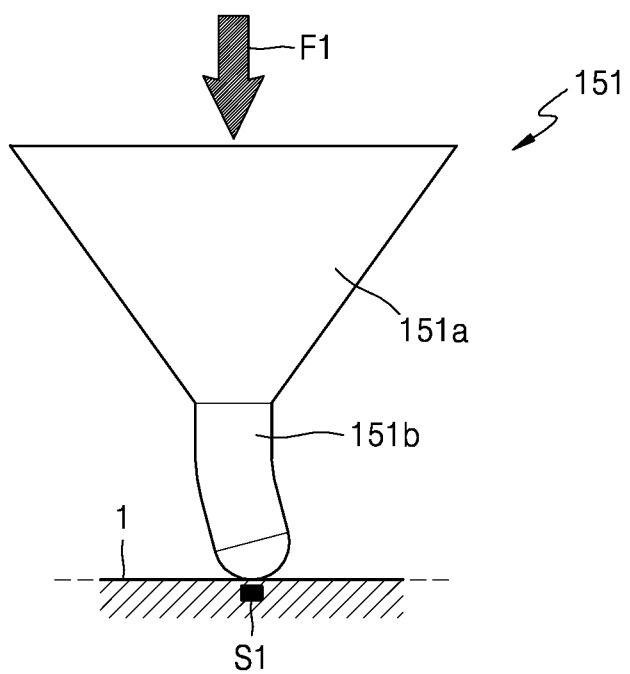
FIGS. 6A through 6C are side views for explaining characteristics of the sensor electrode according to the present exemplary embodiment.
Figure 6B:
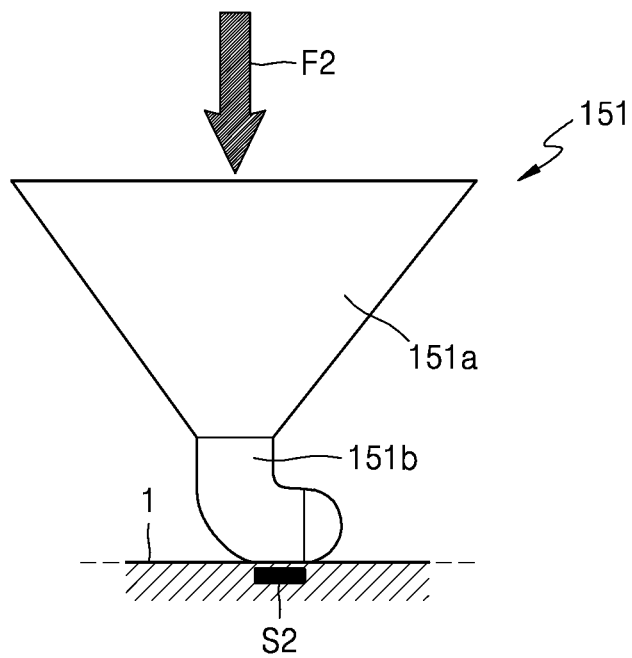
Figure 6C:
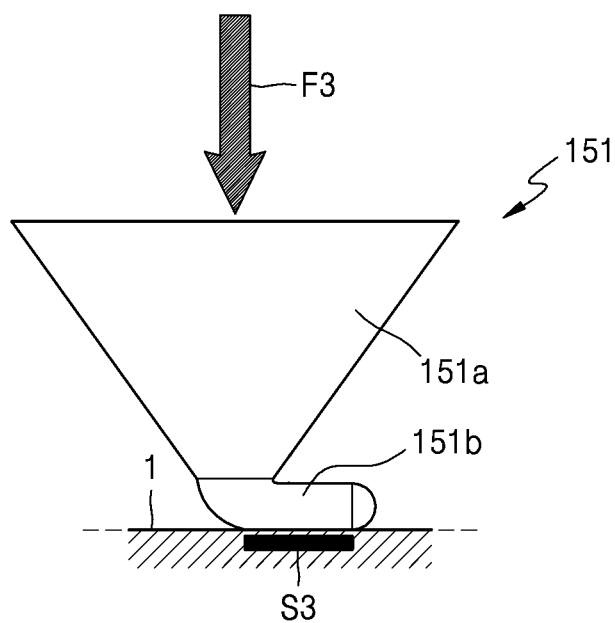

FIG. 5 is a side view of the sensor electrode 151. FIGS. 6A through 6C are side views of the sensor electrode 151. The sensor electrode 151 will now be explained in detail with reference to FIGS. 5 and 6A through 6C. The sensor electrode 151 has a funnel shape and includes a tapering portion 151a and a protruding portion 151b that extends from one end of the tapering portion 151a. That is, the protruding portion 151b extends from the tapered end of the tapering portion 151a a shown in FIG. 5. The sensor electrode 151 may be understood as a non-invasive dry electrode.

The tapering portion 151a has a tapering shape that narrows toward one end. In detail, the tapering portion 151a may have a circular cone shape. The other end (that is, an end having a large cross-sectional area) of the tapering portion 151a is attached to the electrode supporter 153. The one end of the tapering portion 151a refers to an end that is opposite to the end attached to the electrode supporter 153. The protruding portion 151b extends from the one end of the tapering portion 151a to protrude outward, contacts a body part of the living body, and senses bioelectrical signals.

Although it is described that the tapering portion 151a has a circular cone shape, the tapering portion 151a may have a truncated circular cone shape, and the protruding portion 151b may protrude from a top surface of the truncated circular cone shape.

Regarding a longitudinal section of the sensor electrode 151 along a mount surface of the electrode supporter 153 on which the sensor electrode 151 is mounted, that is, a bottom surface of the other end of the tapering portion 151a, a gradient of an outer circumferential surface of the protruding portion 151b may be greater than a gradient of an outer circumferential surface of the tapering portion 151a. That is, on the bottom surface of the tapering portion 151a, an angle θ2 of the outer circumferential surface of the protruding portion 151b may be greater than an angle θ1 of the outer circumferential surface of the tapering portion 151a. In other words, the protruding portion 151b may have a prism shape or a tapering shape having a gradient that is slightly greater than a gradient of the tapering portion 151a. The protruding portion 151b may have, for example, a cylindrical shape.

One end of the protruding portion 151b may have a blunt shape such as a hemispheric shape to minimize pain in the scalp when the protruding portion 151b contacts the scalp. A shape of the one end of the protruding portion 151b is not limited, and may be, for example, sharp or flat shape. A height of the protruding portion 151b may be greater than a diameter of the protruding portion 151b.

The tapering portion 151a and the protruding portion 151b of the sensor electrode 151 may be integrally formed with each other. In this case, the sensor electrode 151 may be formed of a flexible material. When a material is flexible, it means that the material is easily bent by an external force, and a flexible material refers to a material having a high flexibility. The sensor electrode 151 may be formed of a conductive polymer such as conductive silicone or conductive rubber. Alternatively, the sensor electrode 151 may be formed of a flexible and conductive synthetic resin. The protruding portion 151b may have a flexibility that is greater than that of the tapering portion 151a. As described below, when the sensor electrode 151 contacts the scalp, the tapering portion 151a supports the protruding portion 151b and the protruding portion 151b is bent to contact the scalp. In order to satisfy this flexibility relationship, the sensor electrode 151 may have a hardness ranging, for example, from about 40° to about 60°.

The tapering portion 151a and the protruding portion 151b of the sensor electrode 151 may be separately manufactured and then may be adhered to each other. For example, the protruding portion 151b may be formed of conductive silicone or conductive rubber having a high flexibility and the tapering portion 151a may be formed of a synthetic resin having a flexibility that is less than that of the protruding portion 151b. Furthermore, the tapering portion 151a may be formed of a rigid material having no flexibility. The tapering portion 151a may be formed of a conductive or non-conductive material. When the tapering portion 151a is formed of a non-conductive material, an additional conductor (not shown) that is electrically connected to the protruding portion 151b may be inserted into the tapering portion 151a.

FIGS. 6A through 6C are views for explaining characteristics of the sensor electrode 151 according to the present exemplary embodiment. In FIGS. 6A through 6C, strengths of forces F1, F2, and F3 sequentially increase in the order listed. That is, F3>F2>F1. As shown in FIGS. 6A through 6C, the sensor electrode 151 is provided so that the protruding portion 151b of the sensor electrode 151 contacts the skin of the head 1, that is, the scalp. Referring to FIG. 6A, when the force F1 is applied to the sensor electrode 151 in a direction marked with an arrow, the protruding portion 151b of the sensor electrode 151 is bent and a part of one end of the protruding portion 151b contacts the scalp to form a contact area S1. As shown in FIG. 6B, when the force F2 that is stronger than the force F1 is applied, the protruding portion 151b of the sensor electrode 151 is bent so that a side portion, that is, an outer circumferential surface, of the protruding portion 151b contacts the scalp, to form a contact area S2 that is larger than the contact area S1. As shown in FIG. 6C, when the force F3 that is stronger than the force F2 is applied, the protruding portion 151b of the sensor electrode 151 is further bent to form a contact area S3, which is larger than the contact area S2, between the outer circumferential surface of the protruding portion 151 and the scalp. As the contact area increases, impendence between the sensor electrode 151 and the scalp decreases, thereby minimizing signal distortion.

Figure 7:
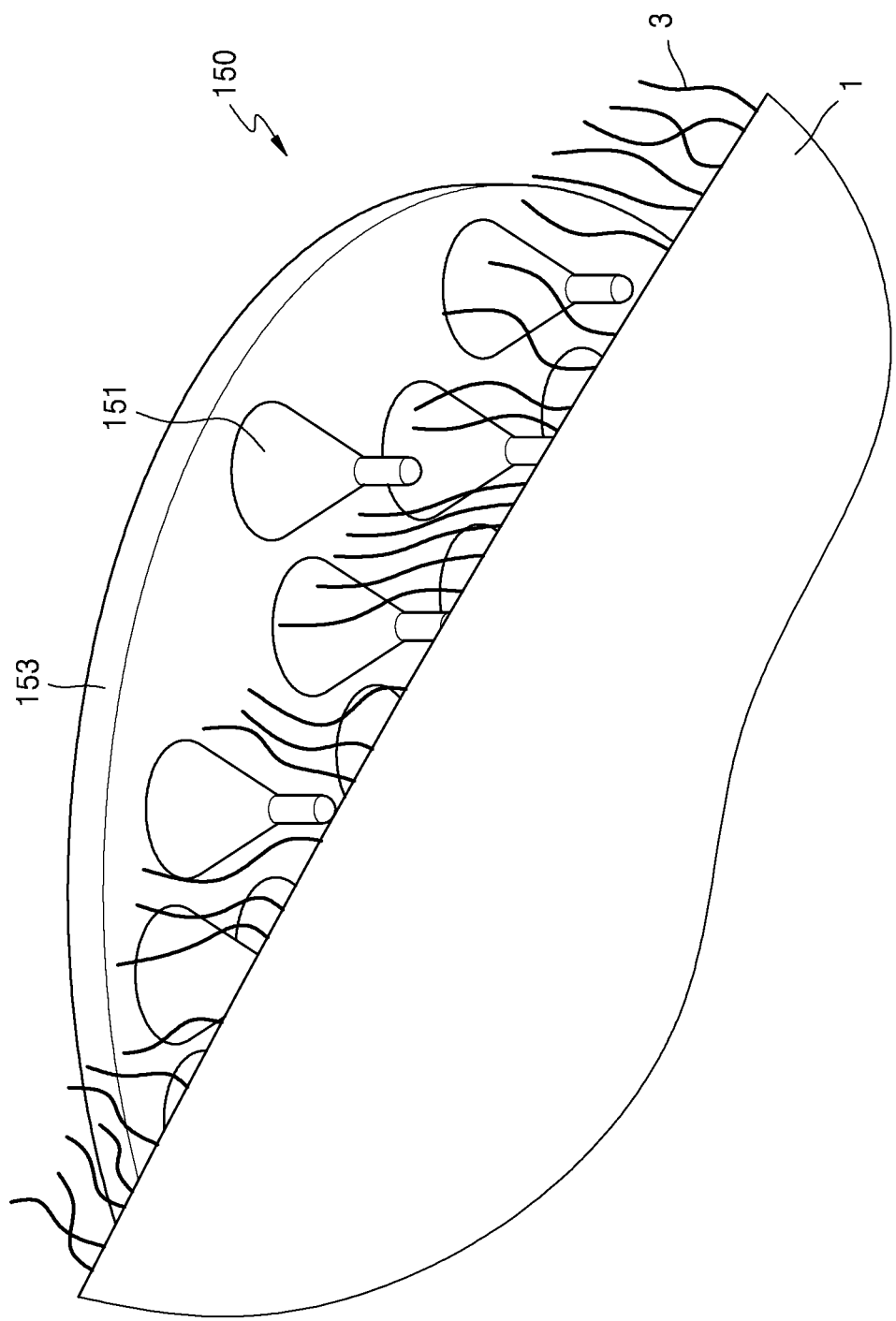
FIGS. 7 and 8 are views illustrating a case where the sensor module is attached to the scalp.
Figure 8:
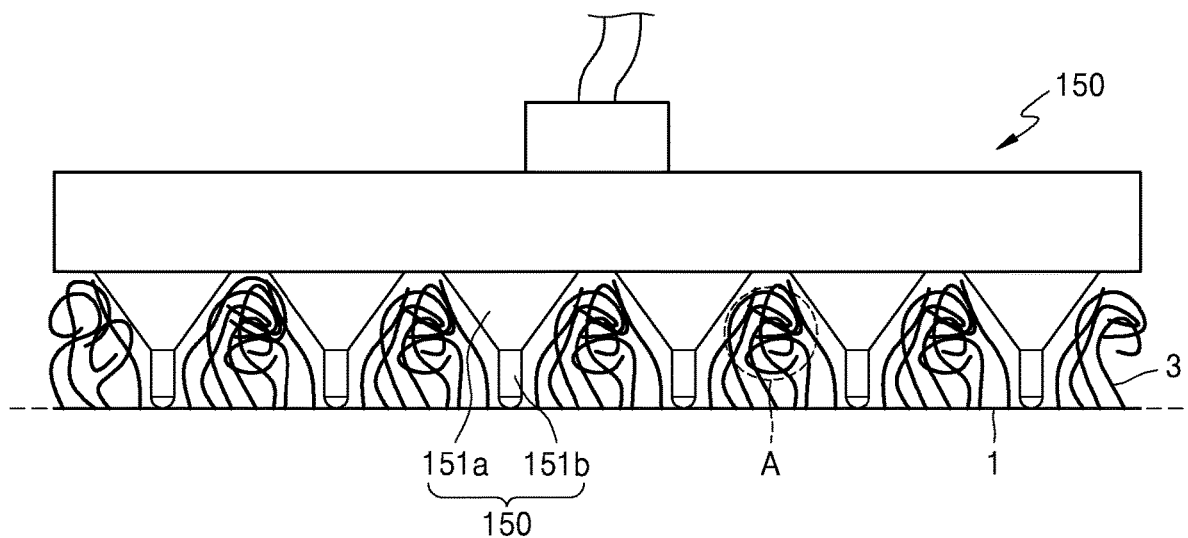

FIGS. 7 and 8 are views illustrating a case where the sensor module 150 is attached to the head 1. As shown in FIGS. 7 and 8, when bioelectrical signals (that is, brain waves) in the head are to be measured, hairs 3 densely distributed on the head 1 (see "A" in FIG. 8) may function as obstructions when the sensor electrode 151 contacts the scalp. The tapering portion 151a of the sensor electrode 151 may support the protruding portion 151b so that the protruding portion 151b passes through the hairs 3, and the protruding portion 151b of the sensor electrode 151 may have a diameter that is less than a diameter of the tapering portion 151a so that the protruding portion 151b may easily pass through the hairs 3 to reach the scalp. Also, since the protruding portion 151b is easily bent, a contact area between the protruding portion 151b and the scalp may be increased.

Figure 9:
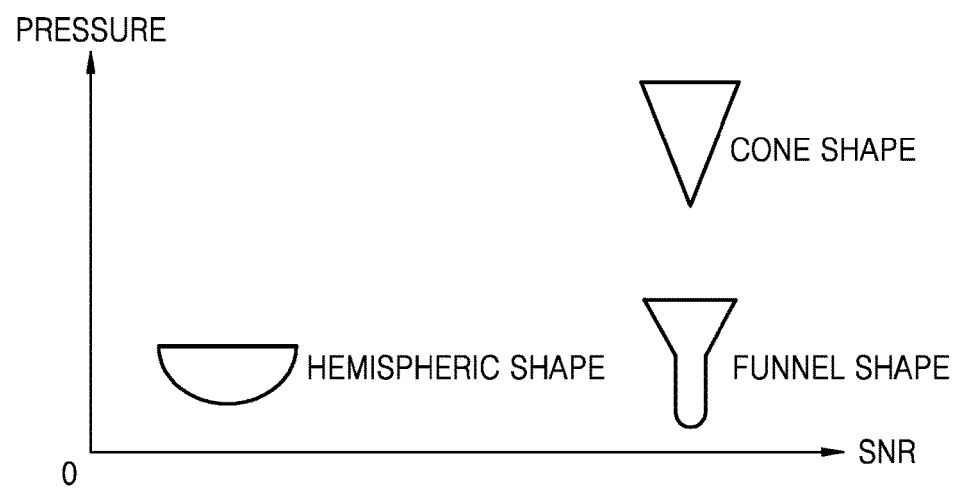
FIG. 9 is a graph showing a relationship between pressure and signal-to-noise ratio (SNR) of the sensor electrode of the present exemplary embodiment and sensor electrodes of comparative examples.

FIG. 9 is a graph showing a relationship between pressure and signal-to-noise ratio (SNR) of the sensor electrode 151 of the present exemplary embodiment and sensor electrodes of comparative examples. Referring to FIG. 9, when brain waves of the head of a person are to be measured, an SNR and a pressure applied to the person vary according to a shape of a sensor electrode. If a hemispheric shape sensor electrode is used, since it is not easy for the hemispheric shape sensor electrode to completely contact the scalp due to hairs of the scalp, there are lots of noise components and thus SNR characteristics are deteriorated. In contrast, since the sensor electrode 151 of the present exemplary embodiment has a funnel shape, the sensor electrode 151 passes through hairs of the scalp and easily completely contacts the scalp, and SNR characteristics are improved. Also, since a circular cone shape sensor electrode has a sharp end, a pressure applied to the scalp is relatively high. In contrast, in the sensor electrode 151 of the present exemplary embodiment, since the protruding portion 151b is bent and an outer circumferential surface of the protruding portion 151b contacts the scalp, a pressure applied to the scalp is reduced.

Referring back to FIGS. 3 and 4, the electrode supporter 153 supports the plurality of sensor electrodes 151. The electrode supporter 153 may be formed of a non-conductive material. For example, the electrode supporter 153 may be formed of, for example, a plastic resin. The plastic resin may be hard or soft. A sensor circuit 160 (see FIG. 10) of the sensor electrode 151 may be buried in the electrode supporter 153, or may be formed as a printed circuit on the rear surface of the electrode supporter 153 that is opposite to the surface of the electrode supporter 153 on which the sensor electrodes 151 are provided. The sensor circuit 160 is electrically connected to a main circuit 140 through the cable 158 of the sensor electrodes 151.

Figure 10:
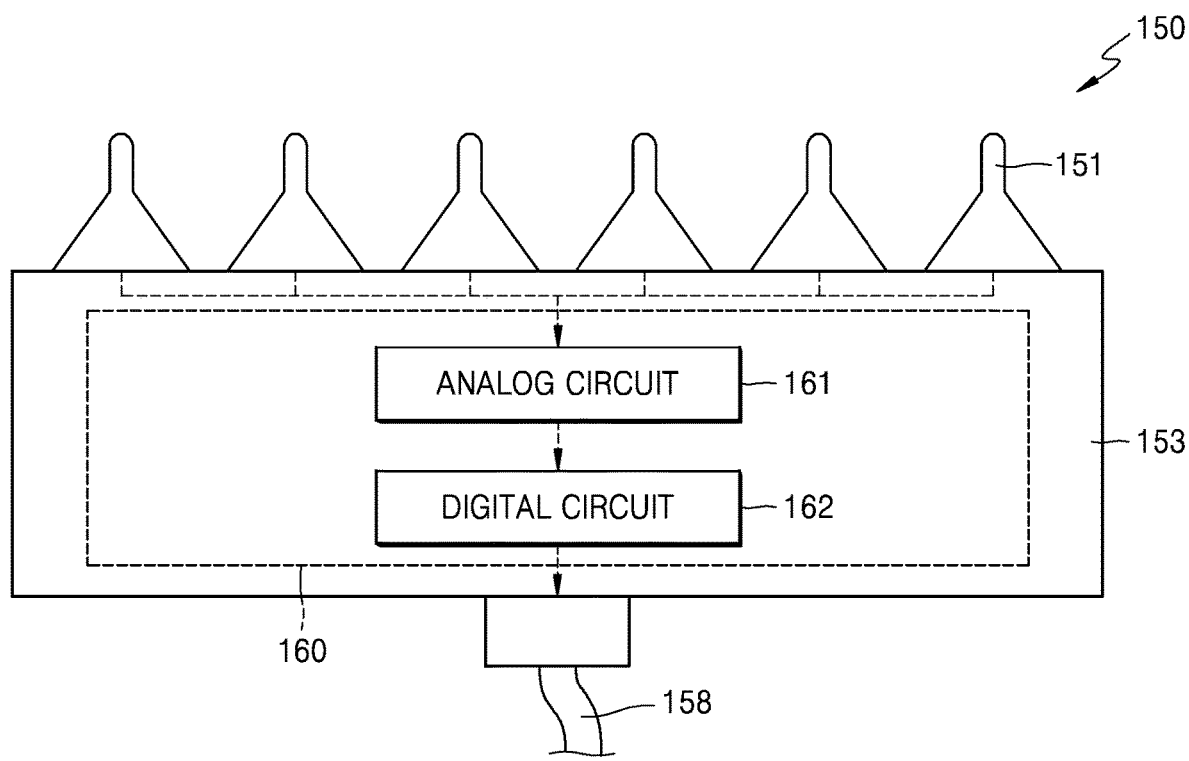
FIG. 10 is a block diagram of a sensor circuit in an electrode supporter for the sensor module.

Referring to FIG. 10, the sensor module 150 may include the sensor circuit 160 that is buried in the electrode supporter 153. The sensor circuit 160 may include an analog circuit 161 and a digital circuit 162.

The analog circuit 161 receives and amplifies weak bioelectrical signals detected by the sensor electrodes 151. For example, the weak bioelectrical signals detected by the sensor electrodes 151 may be summed and then amplified. Alternatively, the weak bioelectrical signals detected by the sensor electrodes 151 may be individually amplified, or may be grouped, summed, and then amplified.

The digital circuit 162 may include an analog-digital converter (ADC) that converts analog signals amplified by the analog circuit 161 into digital signals, and a wired communication module that may output the digital signals through the cable 158. The analog circuit 161 may also include a wireless transmission circuit to transmit the analog or digital signals to the outside, in which case the cable 158 may be omitted.

The cable 158 may include a wiring for bioelectrical signals and a wiring for driving the sensor circuit 160. For example, the wiring for driving the sensor circuit 160 may include, for example, a source (Vcc) line and a ground (GND) line for supplying power, a reference signal line for setting a reference signal for detecting bioelectrical signals, and a line for synchronizing timings of samples. Some of the lines of the wiring for driving the sensor circuit 160 may be omitted.

Since the sensor circuit 160 is included in the sensor module 150 as described above, noise may be minimized, thereby improving signal quality. For example, since analog signals are converted into digital signals, noise input when bioelectrical signals are transmitted from the sensor electrodes 151 to the main circuit 140 (see FIG. 16) of the main body 110 may be reduced or removed.

Figure 11:
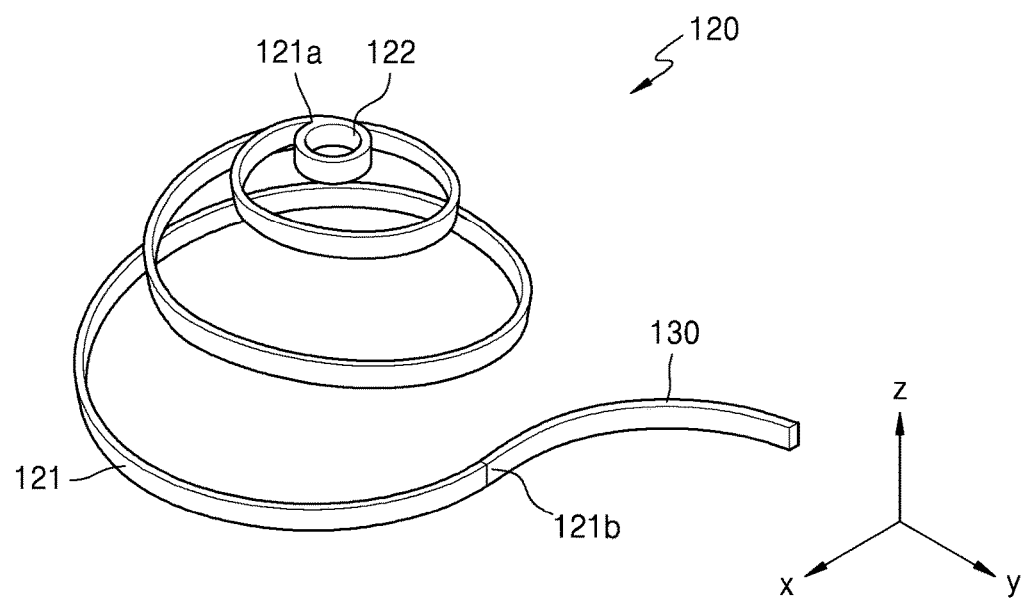
FIG. 11 is a perspective view of a sensor support of the present exemplary embodiment.
Figure 12:
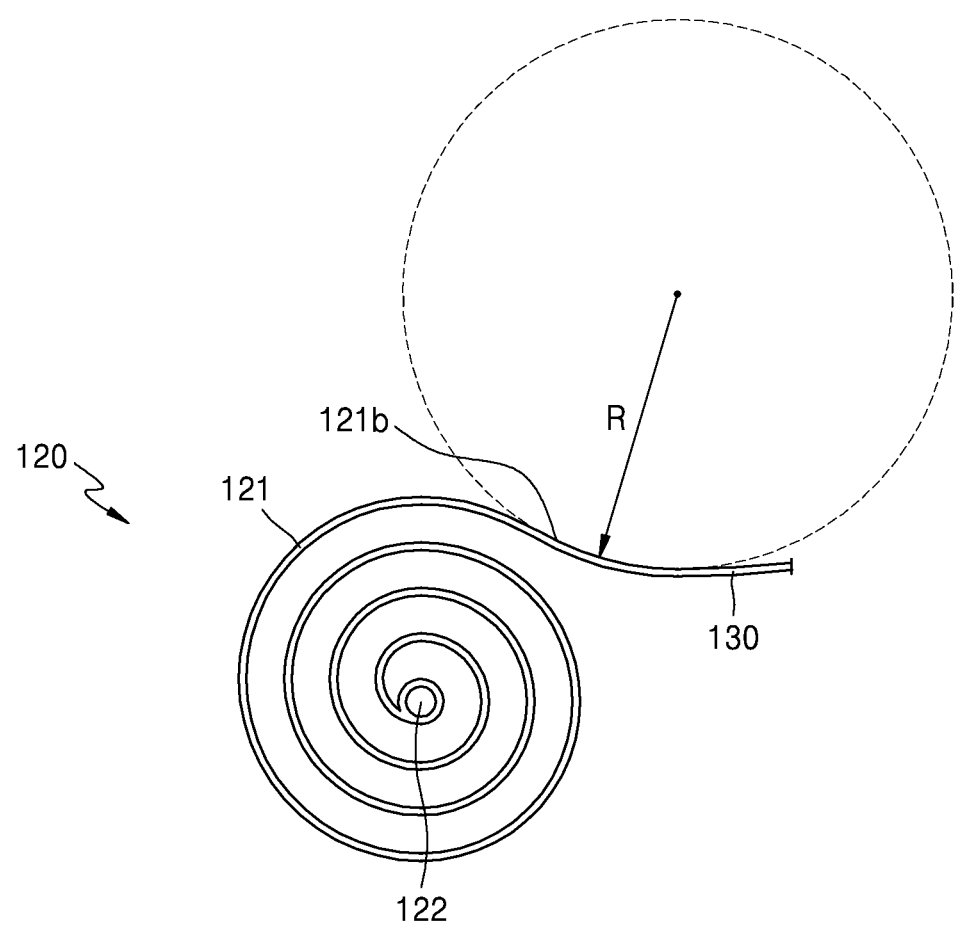
FIG. 12 is a plan view of the sensor support of FIG. 11.
Figure 13A:
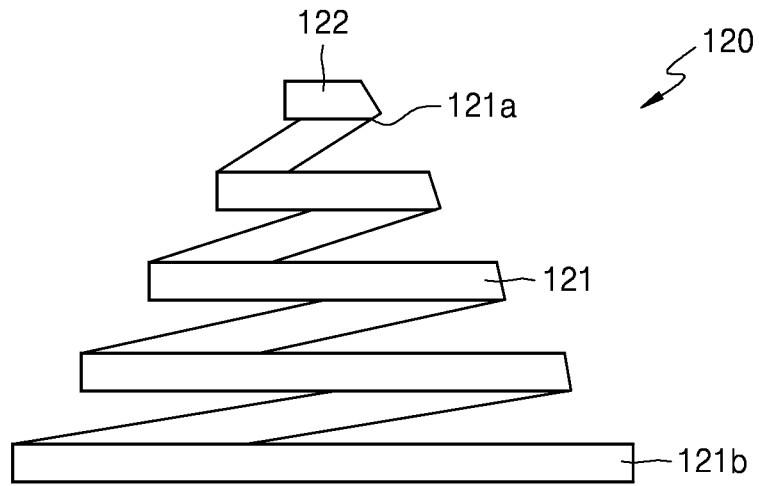
FIGS. 13A through 13C are views of the sensor support having a shape that varies according to a force of pressing the sensor support.
Figure 13B:
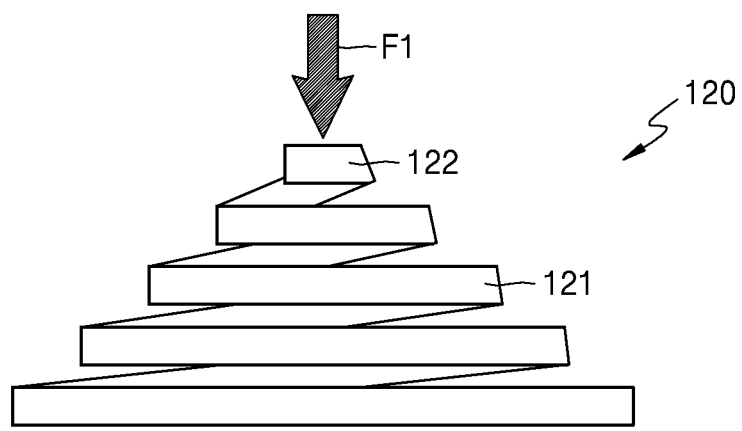
Figure 13C:
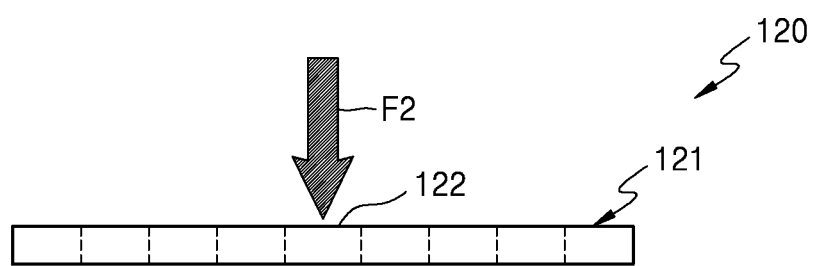

FIG. 11 is a perspective view of the sensor support 120. FIG. 12 is a plan view of the sensor support 120. FIGS. 13A through 13C are views of the sensor support 120 having a shape that varies according to a force of pressing the sensor support 120.

Referring to FIGS. 11 and 12, the sensor support 120 of the present exemplary embodiment that supports the sensor module 150 (see FIG. 3) includes the spiral spring 121 and the sensor mount portion 122 that is provided on one end 121a of the spiral spring 121.

The spiral spring 121 that is rolled into a circular spiral shape may be formed of an elastic material such as plastic or metal. The term elasticity refers to the tendency of a material to return to its original shape after it has been deformed due to an external force. When a surface on which the spiral spring 121 is placed is an xy plane, the sensor mount portion 122 may elastically move in an x-axis direction, a y-axis direction, and a z-axis direction (that is, 3-axis directions). The spiral spring 121 may elastically support the sensor module 150 in 3-axis directions. In other words, the sensor support 120 of the present exemplary embodiment allows the sensor module 150 to move in any-axis direction in a space. The sensor support 120 is connected to the main body 110 through the connection frame 130. As the head 1 moves, a fixed position of the main body 110 may slightly move, and thus one end of the connection frame 130 may move. Alternatively, as the facial expression changes, the scalp may slightly move, and thus relative positions of the sensor module 150 and the main body 110 may slightly change. In this case, since the sensor support 120 elastically supports the sensor module 150 in 3-axis directions, even though the relative positions of the sensor module 150 and the main body 110 change, the sensor module 150 may be stably attached to its original position.

Also, an elasticity of the spiral spring 121 in a direction (e.g., the z-axis direction) perpendicular to the surface (i.e., the xy plane) on which the spiral spring 121 is placed may be greater than an elasticity of the spiral spring 121 in directions (e.g., the x and y-axis directions) parallel to the xy plane, so that a force of pressing the sensor module 150 to the head 1 (that is, an elastic force in the z-axis direction) may be greater than a restoring force in the directions parallel to the xy plane (that is, an elastic force in the x and y-axis directions). For example, as shown in FIG. 11, since the spiral spring 121 is formed by rolling an elastic member having a plate shape whose width direction is the z-axis direction into a circular spiral shape, an elasticity in the z-axis direction may be greater than an elasticity in direction parallel to the xy plane. Alternatively, elasticities of the spiral spring 121 in 3-axis directions may be the same, an elasticity in the z-axis direction may be less than an elasticity in directions parallel to the xy plane, or elasticities in 3-axis directions may be different from one another.

FIGS. 13A through 13C are views of the sensor support 120 having a shape that varies according to a pressing force. FIG. 13A illustrates a case where no force is applied to the sensor support 120. As shown in FIG. 13A, the one end 121a of the spiral spring 121 on which the sensor mount portion 122 is provided may protrude in a direction (i.e., the z-axis direction) perpendicular to the surface (i.e., the xy plane) on which the spiral spring 121 is placed. As shown in FIGS. 13B and 13C, when forces F1 and F2 (where F2>F1) are vertically applied to the sensor mount portion 122, a protruding portion (that is, the sensor mount portion 122) of the spiral spring 121 may move inward. Since the sensor mount portion 122 of the spiral spring 121 protrudes, due to a protruding structure of the spiral spring 121, an area of the sensor module 150 is not affected by a size of the spiral spring 121 and a space in which the sensor module 150 vertically moves may be secured.

Although the sensor support 120 of the present exemplary embodiment is formed so that the one end 121a of the spiral spring 121 on which the sensor mount portion 122 is provided protrudes with respect to the other end 112b of the spiral spring 121 when no force is applied, the inventive concept is not limited thereto. When no force is applied, the entire spiral spring 121 may be provided in a plane.

Referring back to FIGS. 11 and 12, the sensor mount portion 122 is provided on the one end 121a of the spiral spring 121. A groove of the sensor mount portion 122 and the coupling portion 155 of the sensor module 150 may be engaged with each other. The sensor mount portion 122 has, for example, a circular groove, and the coupling portion 155 having a cylindrical shape and protruding from a rear surface of the electrode supporter 153 of the sensor module 150 is inserted into the circular groove of the sensor mount portion 122. A method of mounting the sensor module 150 on the sensor mount portion 122 is not limited thereto. For example, the coupling portion 155 of the sensor module 150 may have a square prism shape, a rectangular prism shape, a triangular prism shape, a pentagonal prism shape, or a hexagonal prism shape, and the sensor mount portion 122 may have a groove that conforms to the shape. Furthermore, the sensor mount portion 122 may be a flat surface, and the sensor module 150 may be mounted on the sensor mount portion 122 by adhering the sensor module 150 to the sensor mount portion 122.

The sensor support 120 may be integrally formed with the connection frame 130. A connection portion (that is, a portion on the other end 121b of the spiral spring 121 is provided) between the connection frame 130 and the spiral spring 121 of the sensor support 120 may have a linear shape or a gently curved shape. For example, as shown in FIG. 12, the connection portion between the connection frame 130 and the spiral spring 121 may have a gently curved outer surface with a curvature R. The curvature R may be predetermined. Accordingly, a mechanical stress which occurs as the sensor support 120 elastically supports the sensor module 150 may be prevent from being concentrated on the connection portion between the connection frame 130 and the spiral spring 121, thereby improving the mechanical durability of the sensor support 120.

Figure 14:
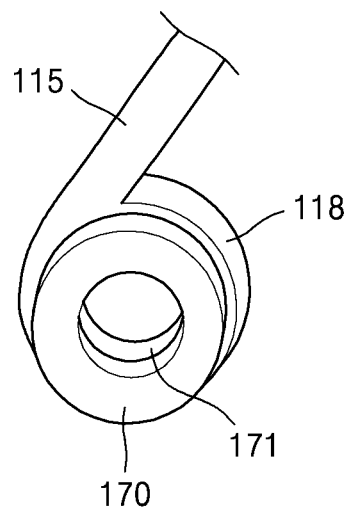
FIG. 14 is a view of a reference electrode that is provided on an ear insertion ring of the apparatus of FIG. 1.

FIG. 14 is a view of the reference electrode 170 that is provided on the ear insertion ring 118 of the apparatus 100 of the present exemplary embodiment. As shown in FIG. 14, the reference electrode 170 may be provided on the ear insertion ring 118. The reference electrode 170 may have a ring shape, and may be coupled to the ear insertion ring 118. In other words, the ear insertion ring 118 may function as an electrode supporter for the reference electrode 170. When the ear insertion ring 118 is inserted into the external part of the ear 5, an outer circumferential surface of the reference electrode 170 contacts the skin of the external part of the ear 5 to measure bioelectrical signals. The reference electrode 170 provides a reference signal for bioelectrical signals (that is, brain waves) measured by the sensor module 150. The reference signal may be a reference voltage or a reference current. Since the ear insertion ring 118 and the reference electrode 170 having a central hole 171 have ring shapes, the ear insertion ring 118 and the reference electrode 170 do not interfere with the input of external sound even when the ear insertion ring 118 and the reference electrode 170 are worn.

In some cases, the reference electrode 170 may be omitted. Alternatively, instead of the reference electrode 170, a ground electrode (not shown) may be provided on the ear insertion ring 118. The ground electrode may be grounded to the head 1, and may remove noise in bioelectrical signals measured by the sensor module 150. The apparatus 100 of the present exemplary embodiment may be provided on each of both ears 5 of the head 1, and the reference electrode 170 may be provided on the ear insertion ring 118 of the main body 110 worn on one of the left ear and the right ear and the ground electrode may be provided on the ear insertion ring 118 of the main body 110 worn on the other ear. In other words, one ear receives the reference electrode 170 and the other ear receives the ground electrode.

Figure 15:
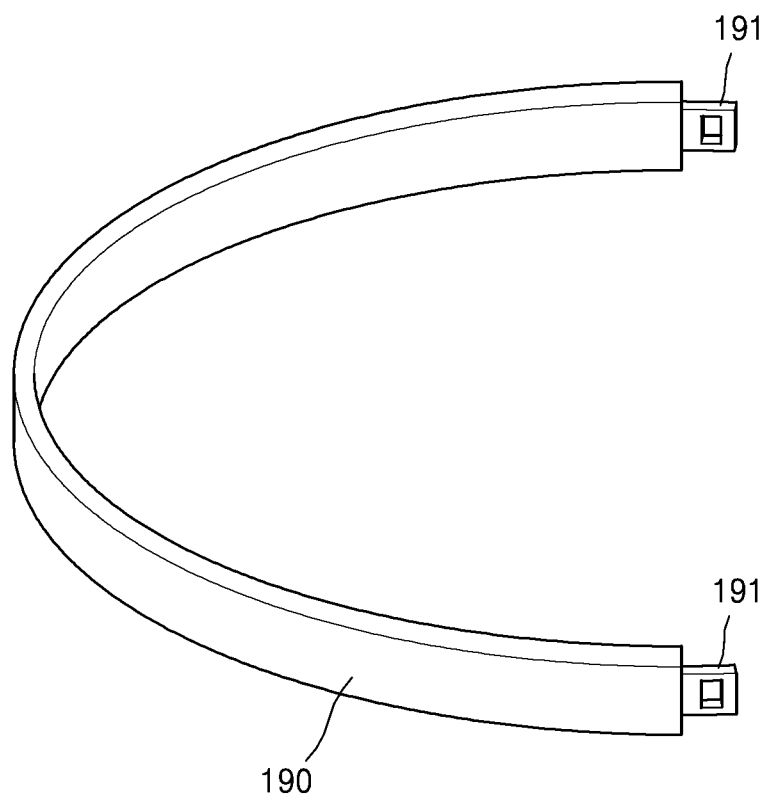
FIG. 15 is a view of an auxiliary frame of the apparatus of FIG. 1.

FIG. 15 is a view of an auxiliary frame 190 of the apparatus 100 of the present exemplary embodiment. Referring to FIG. 15, the apparatus 100 may further include the auxiliary frame 190 that has a hair band shape and fixes the main body 110 to the head 1. The auxiliary frame 190 may be detachably coupled to the main body 110. Since the plurality of slots 112 are formed in the main body 110 as described above, the slots 112 may be commonly used by the connection frame 130 and the auxiliary frame 190. In this case, the auxiliary frame 190 may be inserted into one or more slots 112 that are empty, and may stably fix the main body 110 to the head 1. The apparatus 100 may be worn on each of both ears of the head 1. In this case, one pair of the main bodies 110 may be coupled to respective ends of the auxiliary frame 190 and may be worn on the ears of the head 1. That is, two main bodies 110 may be provided, one main body 110 corresponding to each ear, and the main bodies 110 may be coupled to respective ends of the auxiliary frame 190 so as to be co-located with the wearer's ears. Moreover, the main bodies 110 may be slid along the auxiliary frame 190 to allow for positioning the main bodies 110 with respect to the wearer's ears. The auxiliary frame 190 may be provided with connectors 191 to allow for two auxiliary frames 190 to be connected together in order that the two auxiliary frames 190 may circle the wearer's head.

Figure 16:
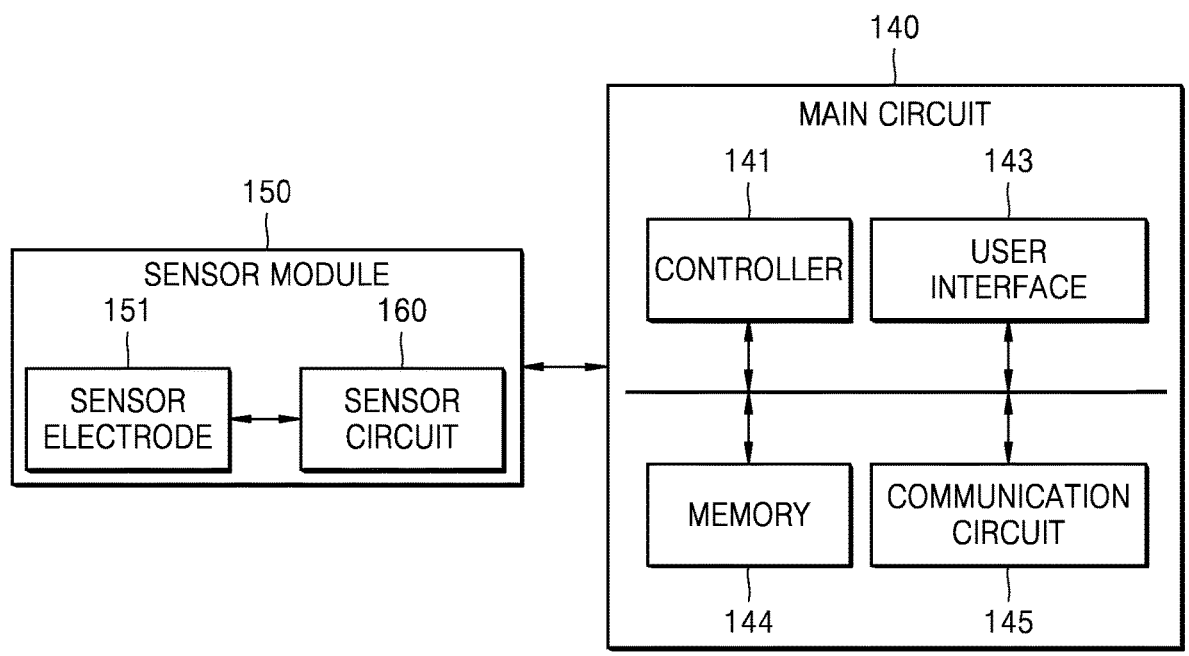
FIG. 16 is a block diagram of the apparatus of FIG. 1.

The main circuit 140 for processing bioelectrical signals obtained by the sensor module 150 may be embedded in the main body 110. FIG. 16 is a block diagram of the apparatus 100 of the present exemplary embodiment. Referring to FIG. 16, the main circuit 140 may include a controller 141, a user interface 143 that receives a control command of a user, a memory 144, and a communication circuit 145.

The controller 141 generates significant brain wave information from bioelectrical signals obtained by the sensor module 150. Signals obtained by the sensor electrode 151 may not be directly used as brain wave data. Various signals as well as brain waves may be included in the signals obtained by the sensor electrode 151. A movement of an eye, a movement of a muscle, a movement of the tongue, and a heart rate of the heart which are close to the scalp may also be input to electrodes and may affect a process of measuring brain waves. Although signals corresponding a movement of an eyelid are rarely generated, since the intensity of potential is high, the signals corresponding to the movement of the eyelid may be easily confused with brain waves. The controller 141 may remove such unnecessary information. Furthermore, the controller 141 may classify brain wave information into $\alpha$ waves, $\beta$ waves, and $\gamma$ waves according to frequencies and may process the brain wave information. Furthermore, the controller 141 may determine a state of the user based on brain wave signals obtained by the sensor electrode 151. For example, the controller 141 may analyze brain wave signals obtained by the sensor electrode 151 according to a preset brain wave model algorithm and may determine whether the user is in an emergency (see FIGS. 60 through 65). A process of additionally processing brain wave information may be performed by an external device (e.g., 1200 of FIG. 59) that wiredly or wirelessly communicates with the apparatus 100, thereby reducing the burden on the controller 141.

Furthermore, the controller 141 controls various functions of the apparatus 100. For example, the controller 141 may generally control the sensor module 150, the user interface 143, the communication circuit 145, and the memory 144 by executing programs that are stored in the memory 144. For example, when the user is in an emergency, the controller 141 may control the communication circuit 145 to transmit information about the emergency of the user to an external device or an output device 114 (see FIG. 2) to output an alarm.

The user interface 143 receives data for controlling the apparatus 100. For example, the user interface 143 includes a switch or the like and receives a control command of the user such as an on/off command or an operation mode command.

The memory 144 may store original data of bioelectrical signals obtained by the sensor module 150 or information about the living body generated by the controller 141. Also, the memory 144 may store a program for controlling an operation of the apparatus 100, a brain wave model algorithm for analyzing bioelectrical signals, or authentication information. Furthermore, the memory 144 may store state information of the user (for example, a brain wave pattern corresponding to an emergency or a brain wave pattern corresponding to a situation that needs administration), and may enable the controller 141 to determine a state of the user.

The communication circuit 145 includes at least one of a wired communication module and a wireless communication module. The wireless communication module may include, for example, a short-range communication module or a mobile communication module. The short-range communication module refers to a module for short-range communication within a predetermined distance. Examples of a short-range communication technology may include, but are not limited to, wireless LAN, Wi-Fi, Bluetooth, ZigBee, Wi-Fi Direct (WFD), ultra-wideband (UWB), infrared data association (IrDA), Bluetooth low energy (BLE), and near field communication (NFC). The mobile communication module transmits/receives wireless signals to/from at least one of a base station, an external terminal, and a server through a mobile communication network. The wired communication module refers to a module for communication using electrical signals or optical signals, and examples of a wired communication technology may include a twisted pair cable, a coaxial cable, an optical fiber cable, and an Ethernet cable. The communication circuit 145 receives bioelectrical signals obtained by the sensor module 150 and transmits a control signal or the like. Also, the communication module 145 may transmit, to an external electronic device, at least one of bioelectrical signals obtained by the sensor module 150 and information about the living body generated by the controller 141, and may obtain information for processing signals or a control signal from the external electronic device.

An output device 114 (see FIG. 2) for expressing information about the living body generated by the controller 141 may be further included in the main body 110. The output device may include at least one of a speaker, a vibration module, a lamp, and a display. The output device may display information about the living body processed by the controller 141 or may output an alarm indicating an emergency.

Also, the main circuit 140 may include at least one of a battery and an energy harvest module for driving the sensor module 150 and the main circuit 140.

Although the connection frame 130 is detachably inserted into the slot 112 of the main body 110 in the previous exemplary embodiments, the connection frame 130 may be integrally formed with the main body 110. If a 3D printer is used, the main body 110 and the connection frame 130 may be integrally formed by using a plastic mold to be suitable for a shape of the head of the user.

Although the sensor electrode 151 includes the tapering portion 151a having a circular cone shape and the protruding portion 151b having a cylindrical shape in FIGS. 5 through 8, the inventive concept is not limited thereto.

Figure 17A:
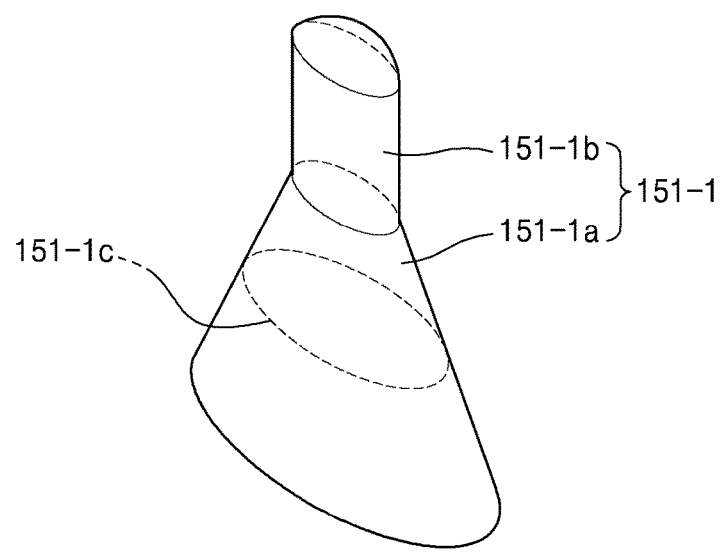
FIGS. 17A through 17D are views of various modifications of the sensor electrode according to various exemplary embodiments.
Figure 17B:
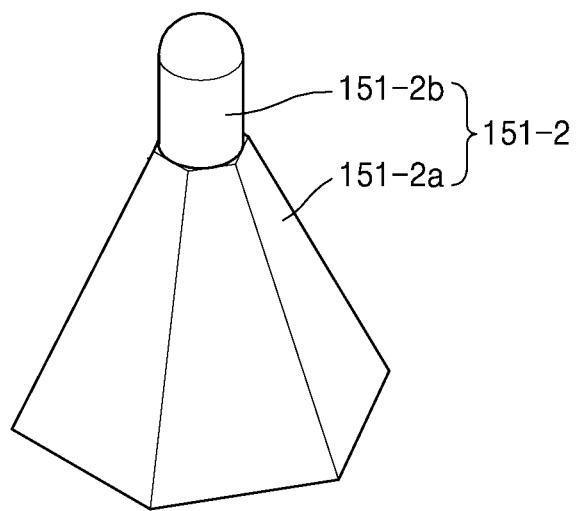
Figure 17C:
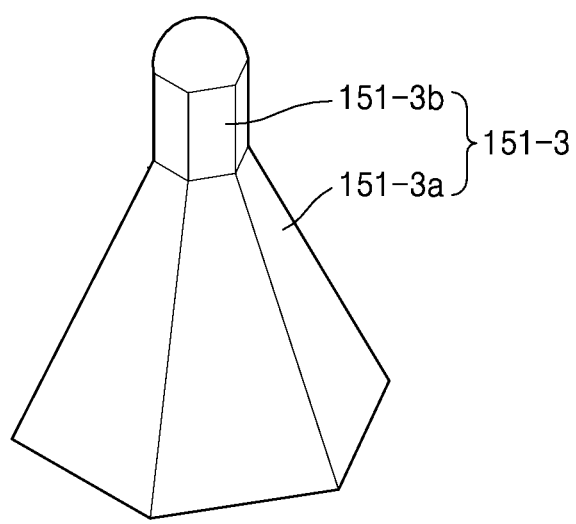
Figure 17D:
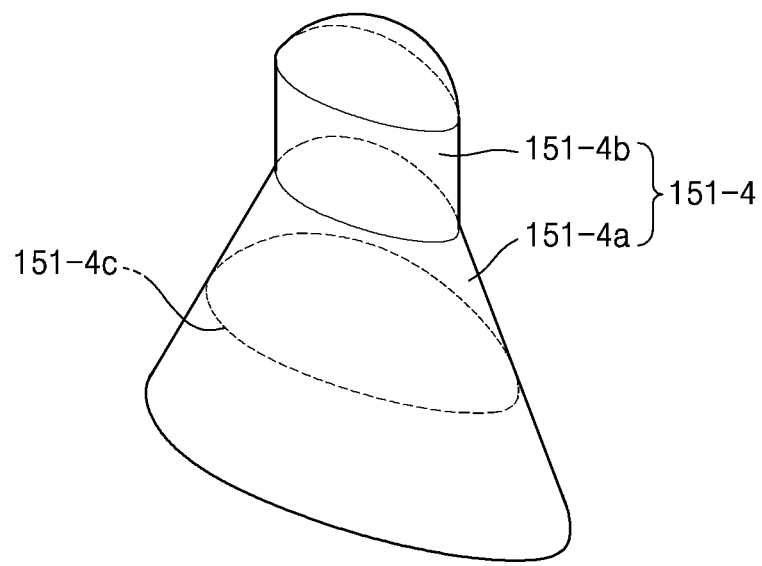

FIGS. 17A through 17D are views of various modifications of the sensor electrode 151. For example, as shown in FIG. 17A, a sensor electrode 151-1 may include a tapering portion 151-1a that has an elliptic cone shape and a protruding portion 151-1b that has an elliptic cylindrical shape and extends from one end of the tapering portion 151-1a. A cross-section 151-1c of the tapering portion 151-1a has an elliptic shape. Although it is described that the tapering portion 151-1a has an elliptic cone shape, the tapering portion 151-1a may have a truncated elliptic cone shape, and the protruding portion 151-1b may be provided on a top surface of the truncated elliptic cone shape. One end of the protruding portion 151-1*b* may have a blunt shape such as a hemispheric shape as shown in FIG. 17A. Alternatively, as shown in FIG. 17B, a sensor electrode 151-2 may include a tapering portion 151-2*a* that has a polypyramid shape and a protruding portion 151-2*b* that has a cylindrical shape and extends from one end of the tapering portion 151-2*a*. Examples of the polypyramid shape may include a triangular pyramid shape, a quadrangular pyramid shape, and a pentagonal pyramid shape. Alternatively, as shown in FIG. 17C, a sensor electrode 151-3 may include a tapering portion 151-3*a* that has a polypyramid shape and a protruding portion 151-3*b* that has a prism shape and extends from one end of the tapering portion 151-3*a*. Although it is described that each of the tapering portions 151-2*a* and 151-3*a* has a polypyramid shape, each of the tapering portion 151-2*a* and 151-3*a* may have a truncated polypyramid shape, and each of the protruding portions 151-2*b* and 151-3*b* may be provided on a top surface of the truncated polypyramid shape. Alternatively, as shown in FIG. 17D, a tapering portion 151-4*a* may have a streamlined cone shape and a cross-section 151-4*c* of the tapering portion 151-4*a* may have a streamlined shape. Alternatively, a sensor electrode may include a tapering portion that has an elliptic cone shape or a polypyramid shape and a protruding portion that has a cylindrical shape, an elliptic cylindrical shape, or a prism shape and protrudes from the tapering portion. A tapering portion of a sensor electrode may have a cone shape having an atypical cross-section. Furthermore, a central axis of the tapering portion and/or the protruding portion may be perpendicular or inclined with respect to the electrode supporter 153. The term tapering shape does not limit to a shape having a cross-sectional area that decreases away from the other end toward one end (that is, on which a protruding portion is provided). In other words, the term tapering shape may refer to a shape having a cross-sectional area that decreases from the other end toward one end in most regions and is constant in some regions.

Figure 18:
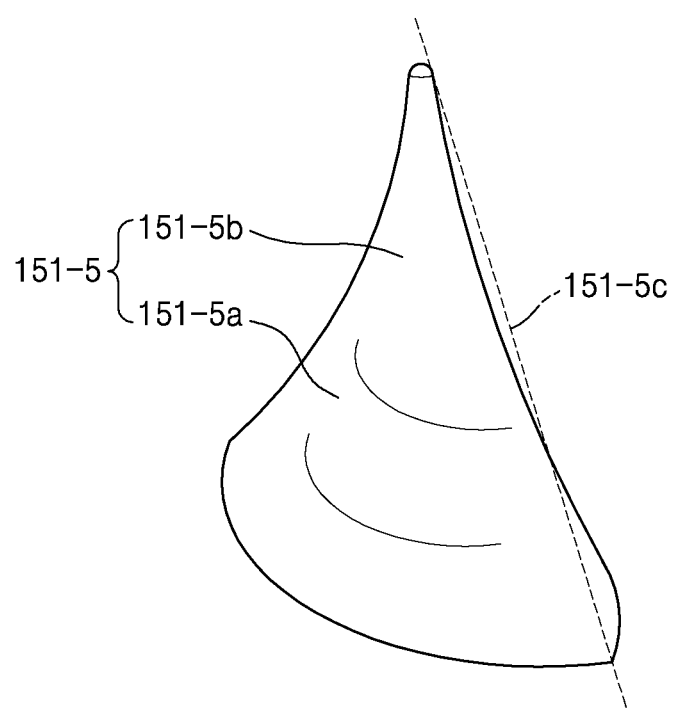
FIG. 18 is a view of a sensor electrode according to another exemplary embodiment.

FIG. 18 is a view of another modification of the sensor electrode 151. As shown in FIG. 18, in a sensor electrode 151-5, an outer surface of a tapering portion 151-5*a* and an outer surface of the protruding portion 151-5*b* may not be separated from each other and may be connected to have a gently curved surface. Furthermore, the outer surfaces of the tapering portion 151-5*a* and the protruding portion 151-5*b*, that is, an inclined plane of the sensor electrode 151-5, may be concave when compared with an inclined plane 151-5*c* of a circular cone. In other words, with respect to a bottom surface of the sensor electrode 151-5, a gradient of a longitudinal section of the sensor electrode 151-5 increases away from the tapering portion 151-5*a* toward the protruding portion 151-5*b*. A cross-sectional area of the sensor electrode 151-5 sharply decreases toward the protruding portion 151-5*b*, and thus a flexibility sharply increases toward one end. Accordingly, a portion of the sensor electrode 151-5 having a greater flexibility may be understood as the protruding portion 151-5*b*.

Figure 19A:
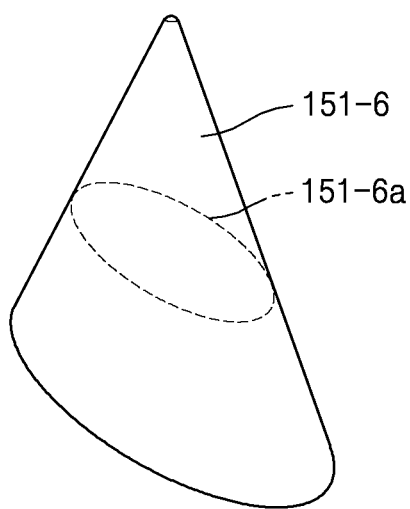
FIG. 19A is a view of a sensor electrode according to another exemplary embodiment.
Figure 19B:
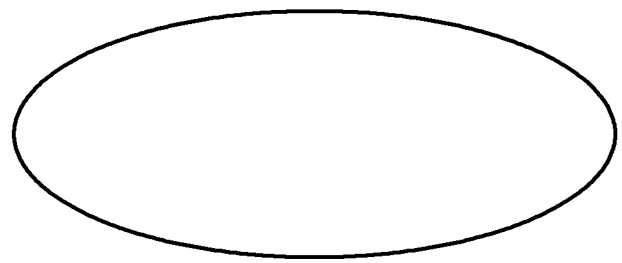
FIG. 19B is a cross-sectional view of the sensor electrode of FIG. 19A.
Figure 20:
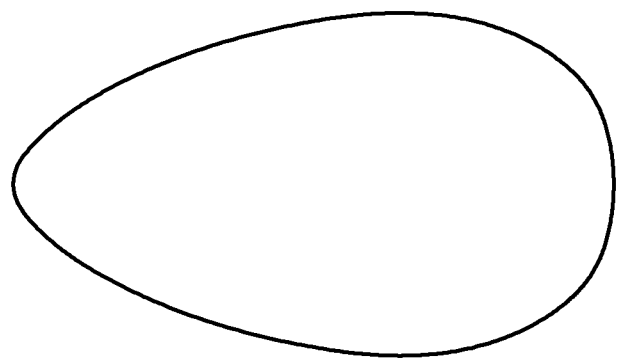
FIG. 20 is a cross-sectional view of a sensor electrode according to another exemplary embodiment.

FIGS. 19A and 19B are views of another modification of the sensor electrode 151. A sensor electrode 151-6 may include only a tapering portion 151-6*a*, without a protruding portion. As shown in FIG. 19B, a cross-section of the sensor electrode 151-6 may have an elliptic shape. One end of the sensor electrode 151-6 may have a blunt shape such as a hemispheric shape. Since a cross-section of the sensor electrode 151-6 has an elliptic shape, the sensor electrode 151-6 may contact a surface of the living body while easily passing through obstructions on the surface of the living body. For example, when bioelectrical signals (that is, brain waves) in the scalp are to be measured, although hairs densely distributed on the scalp may become obstructions, since the sensor electrode 151-6 has an elliptic cone shape, the sensor electrode 151-65 may easily pass through the hairs to reach the scalp. A cross-sectional shape of the sensor electrode 151-6 is not limited to an elliptic shape, and, for example, the sensor electrode 151-6 may have a cross-section having a streamlined shape as shown in FIG. 20.

Although the sensor electrode includes the tapering portion in the previous exemplary embodiments, the inventive concept is not limited thereto. The sensor module 150 applied to the apparatus 100 of FIG. 1 may include sensor electrodes that do not include a tapering portion but that include only a protruding portion having a prism shape (e.g., 151*b* of FIG. 5). In this case, when each sensor electrode contacts a body part, a protruding portion is bent by a pressing force, and a side portion, that is, an outer circumferential surface, of the protruding portion contacts the body part, to sense bioelectrical signals.

Furthermore, the sensor module 150 applied to the apparatus 100 of FIG. 1 may include sensor electrodes each having a hemispheric shape or sensor electrodes each including a protruding portion having a stepped shape.

FIGS. 21A through 21E are views of the sensor support 120 according to other exemplary embodiments.

Figure 21A:
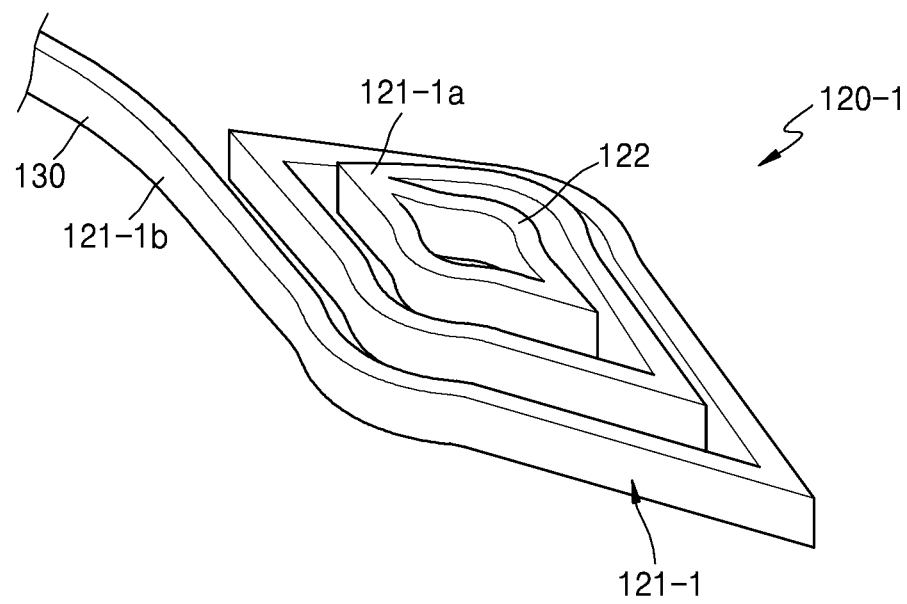
FIGS. 21A through 21E are views of the sensor support according to other exemplary embodiments.

Although the sensor support 120 includes the spiral spring 121 that is rolled into a circular shape in FIGS. 3, 11, 12, and 13A through 13C, the inventive concept is not limited thereto. For example, as shown in FIG. 21A, a sensor support 120-1 may include a spiral spring 121-1 that is rolled into a diamond shape. The spiral spring 121-1 having a diamond shape is an example, and any of other spiral springs having various atypical shapes may be used. The sensor mount portion 122 may be provided on one end 121-1*a* of the spiral spring 121-1, and the connection frame 130 and the other end 121-1*b* of the spiral spring 121-1 may be connected to each other to have a gently curved surface.

Figure 21B:
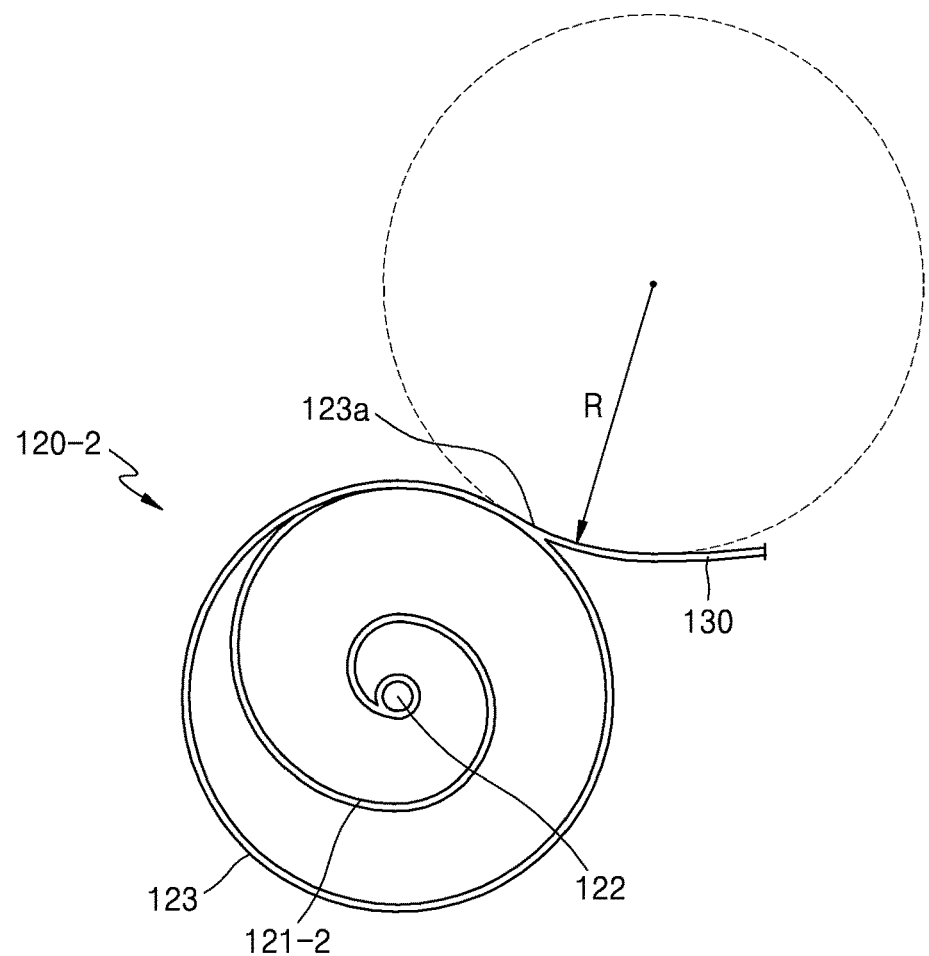

Also, although the sensor support 120 includes only the spiral spring 121 and the sensor mount portion 122 in FIGS. 3, 11, 12, and 13A through 13C, the inventive concept is not limited thereto. For example, as shown in FIG. 21B, a sensor support 120-2 may further include an edge support 123 that surrounds an outer surface of a spiral spring 121-2. The edge support 123 protects and supports the spiral spring 121-2. The edge support 123 is connected to the connection frame 130. Outer surfaces of the edge support 123 and the connection frame 130 may be connected to each other to have a gently curved surface. For example, as shown in FIG. 21B, the outer surfaces of the edge support 123 and the connection frame 130 may be connected to each other to have a gently curved surface with a predetermined curvature R.

Figure 21C:
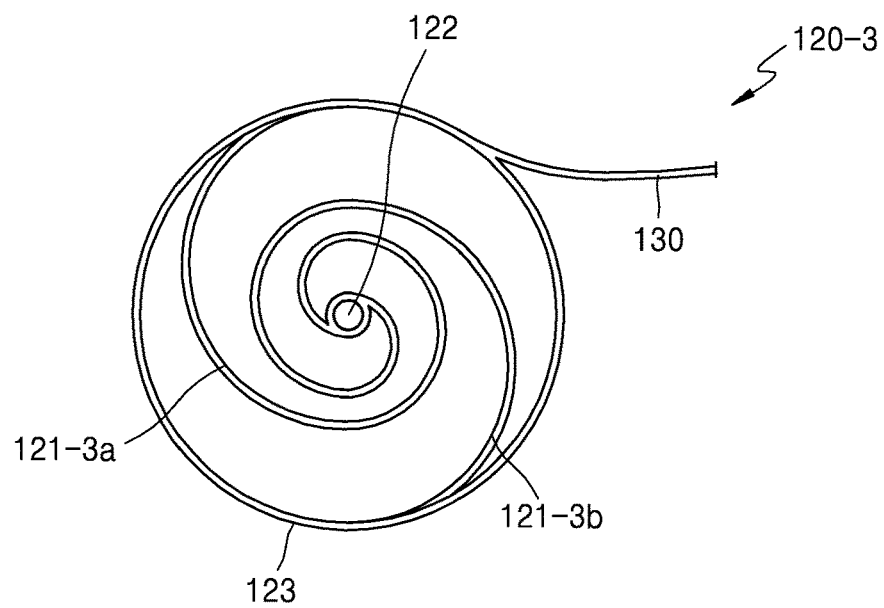
Figure 21D:
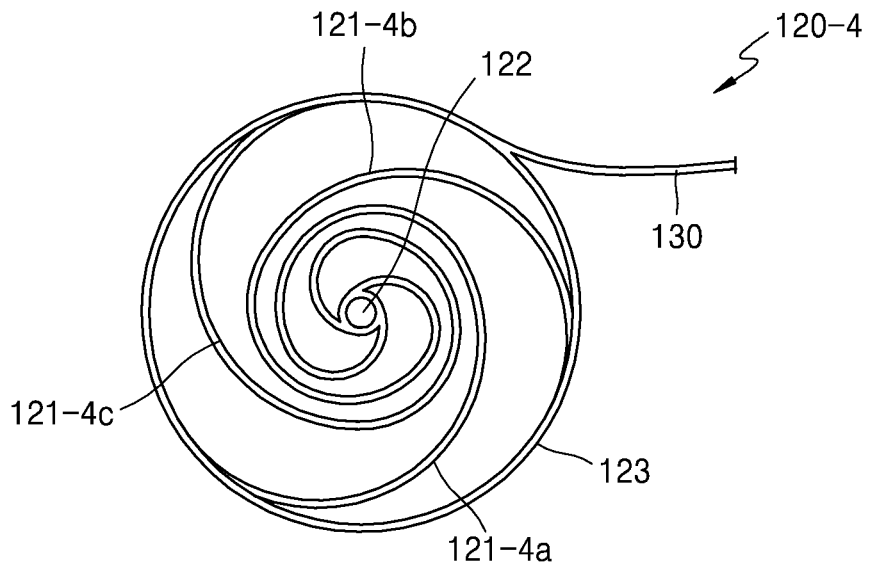
Figure 21E:
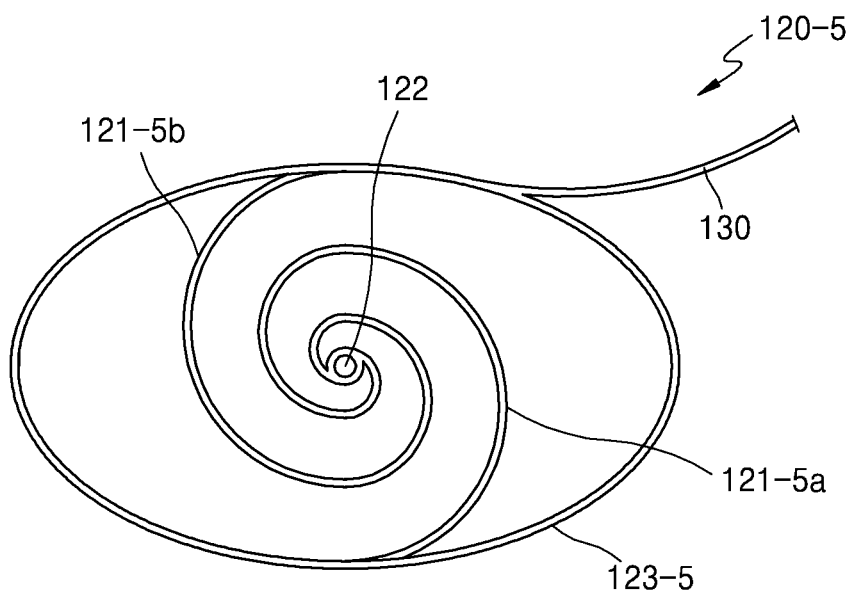

Also, although the sensor supports 120, 120-1, and 120-2 include one spiral spring, such as spring 121, 121-1, and 121-2 in FIGS. 3, 11, 12, and 13A through 13C, the inventive concept is not limited thereto. For example, as shown in FIG. 21C, a sensor support 120-3 may include two spiral springs 121-3*a* and 121-3*b*, or as shown in FIG. 21D, a sensor support 120-4 may include three spiral springs 121-4*a*, 121-4*b*, and 121-4*c*. The number of spiral springs included in a sensor support in each exemplary embodiment is exemplary, and the inventive concept is not limited thereto. As the number of spiral springs increases, an elasticity may be more uniformly provided, and a force of supporting the sensor module 150 may be distributed. Alternatively, as shown in FIG. 21E, a sensor support 120-5 may include spiral springs 121-5*a* and 121-5*b* that is rolled into an elliptic shape. In this case, the sensor support 120-5 may further include an edge support 123-5 that has an elliptic shape and surrounds outer surfaces of the spiral springs 121-5a and 121-5b. Outer surfaces of the edge support 123-5 and the connection frame 130 may be connected to each other to have a gently curved surface. Although the spiral springs 121-5a and 121-5b have elliptic shapes, the spiral springs 121-5a and 1321-5b may be modified into any of various other shapes to have a design element.

The spiral springs of the sensor supports 120-2, 120-3, and 120-5 of FIGS. 21B through 21E may be provided in a plane. Alternatively, as described with reference to FIG. 11, one end on which the sensor mount portion 122 is provided may protrude with respect to a portion to which the edge support 123 is connected.

The spiral spring 121 is, for example, but is not limited to, a support structure that elastically supports the sensor electrode 151 so that the sensor electrode 151 moves in 3-axis directions.

Figure 22A:
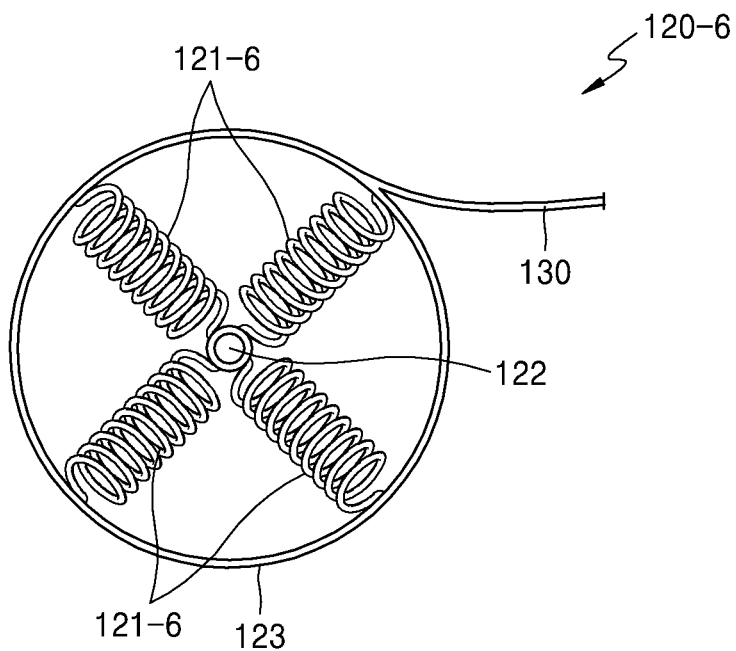
FIGS. 22A and 22B are views of sensor supports according to other exemplary embodiments.

FIG. 22A is a view of a sensor support 120-6 according to another exemplary embodiment. Referring to FIG. 22A, the sensor support 120-6 may include the edge support 123 that is spaced apart by an interval from the sensor mount portion 122 on which the sensor module 150 is mounted and surrounds an outer surface of the sensor mount portion 122 and four springs 121-6 that connect the edge support 123 and the sensor mount portion 122. The interval may be predetermined. The springs 121-6 may be coil springs, rubber bands, or other elastic members. The four springs 121-6 elastically support the sensor mount portion 122 so that the sensor mount portion 122 moves in 3-axis directions. Elasticities of the four springs 121-6 may be appropriately designed so that an elasticity applied in a direction perpendicular to a surface on which the sensor support 120-6 is placed is greater than an elasticity applied in a direction parallel to the surface on which the sensor support 120-6 is placed, an elasticity applied in a vertical axis direction is less than an elasticity applied in a direction parallel to a plane, elasticities applied in 3-axis directions are the same, or elasticities applied in 3-axis directions are different from one another. Although the four springs 121-6 are provided as a support structure in FIG. 22A, the number of the springs 121-6 is not limited thereto.

Figure 22B:
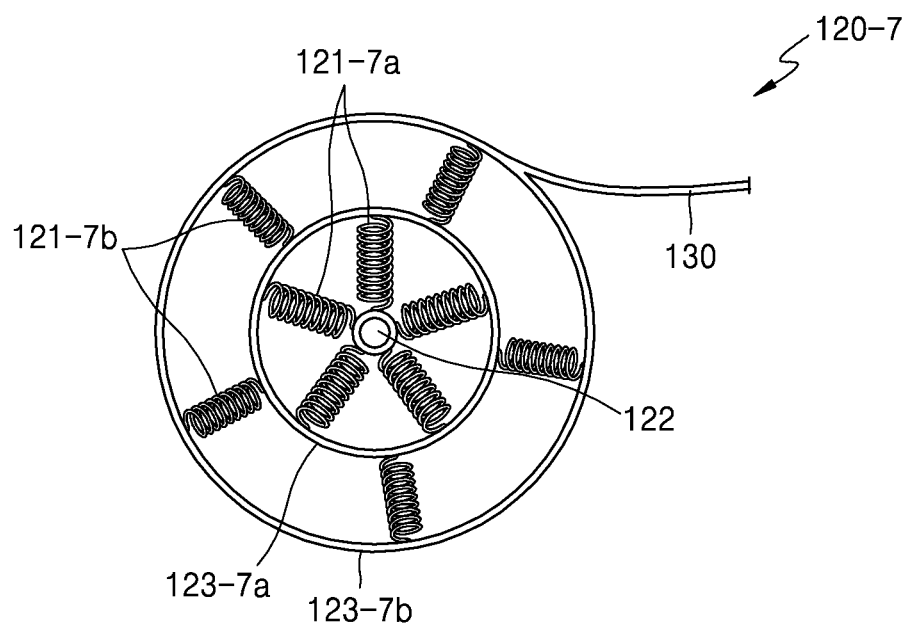

FIG. 22B is a view of a sensor support 120-7 according to another exemplary embodiment. Referring to FIG. 22B, the sensor support 120-7 includes a first edge support 123-7a that is spaced apart by an interval from the sensor mount portion 122 on which the sensor module 150 is mounted and surrounds an outer surface of the sensor mount portion 122, and a second edge support 123-7b that is spaced apart by an interval from the first edge support 123-7a and surrounds an outer surface of the first edge support 123-7a. The intervals may be predetermined and may be different. The sensor mount portion 122 and the first edge support 123-7a are elastically connected to each other by five first springs 121-7a, and the first edge support 123-7a and the second edge support 123-7b are elastically connected to each other by five second springs 121-7b. An elastic modulus of each first spring 121-7a and an elastic modulus of each second spring 123-7b may be the same or different from each other. The number of the first and second springs 121-7a and 121-7b is not limited. Furthermore, although two edge supports are used, the number of edge supports may be three or more.

Although the sensor module 150 includes the sensor circuit 160 including the analog circuit 161 and the digital circuit 162 in the previous exemplary embodiment, the inventive concept is not limited thereto.

Figure 23:
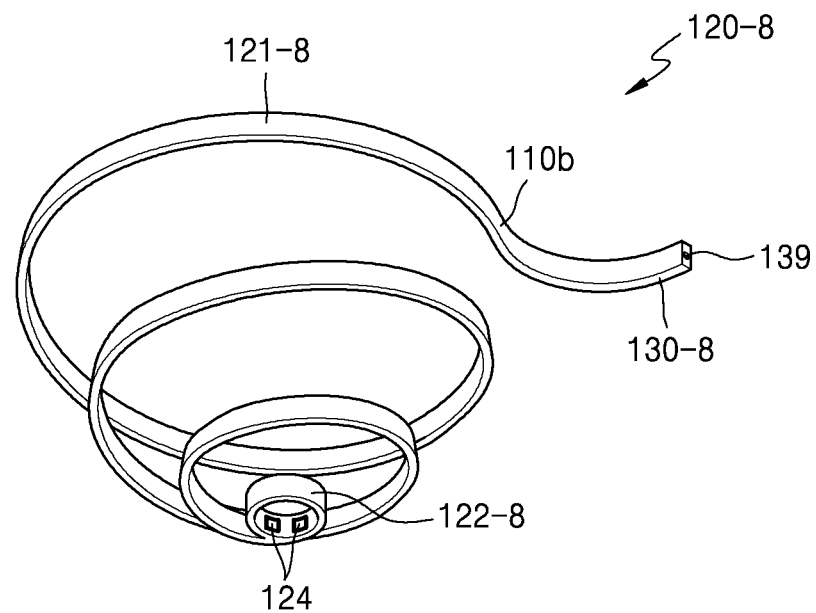
FIG. 23 is a view of a sensor support according to another exemplary embodiment.

Although the cable 158 of the sensor module 150 is exposed to the outside in the previous exemplary embodiment, the inventive concept is not limited thereto. FIG. 23 is a view of a sensor support 120-8 according to another exemplary embodiment. Referring to FIG. 23, the sensor support 120-8 of the present exemplary embodiment includes a spiral spring 121-8 in which a wiring is buried. Connection terminals 124 for electrical connection when the sensor module 150 is mounted may be provided on a sensor mount portion 122-8 of the sensor support 120-8. In this case, instead of the cable 158, connection terminals (not shown) for electrical contact with the connection terminals 124 of the sensor mount portion 122-8 may be provided on the coupling portion 155 of the sensor module 150 (see FIG. 3). The sensor support 120-8 may be integrally formed with the connection frame 130 as described above. In this case, a wiring 139 may also be buried in the connection frame 130. Alternatively, inner portions of the connection frame 130 and the sensor support 120-8 may be empty, and a cable may be inserted into the inner portions of the connection frame 130 and the sensor support 120-8. Alternatively, the inner portions of the sensor support 120-8 and the connection frame 130 may each be formed of a conductor, and may function as the cable 158.

Although the sensor module 150 includes the plurality of sensor electrodes 151 that are provided on one electrode supporter 153 in the previous exemplary embodiments, the inventive concept is not limited thereto. One sensor electrode 151 may be provided on one electrode supporter 153. Also, the electrode supporter 153 may be integrally formed with the sensor mount portion 122 (see FIG. 11), and may not be structurally separated from the sensor mount portion 122. Accordingly, the sensor module 150 may be understood as one individual sensor electrode 151 as compared with the previous exemplary embodiments.

Although the sensor circuit 160 of the sensor module 150 includes the analog circuit 161 and the digital circuit 162 including the wired communication module and the ADC in FIG. 10, the inventive concept is not limited thereto.

Figure 24A:
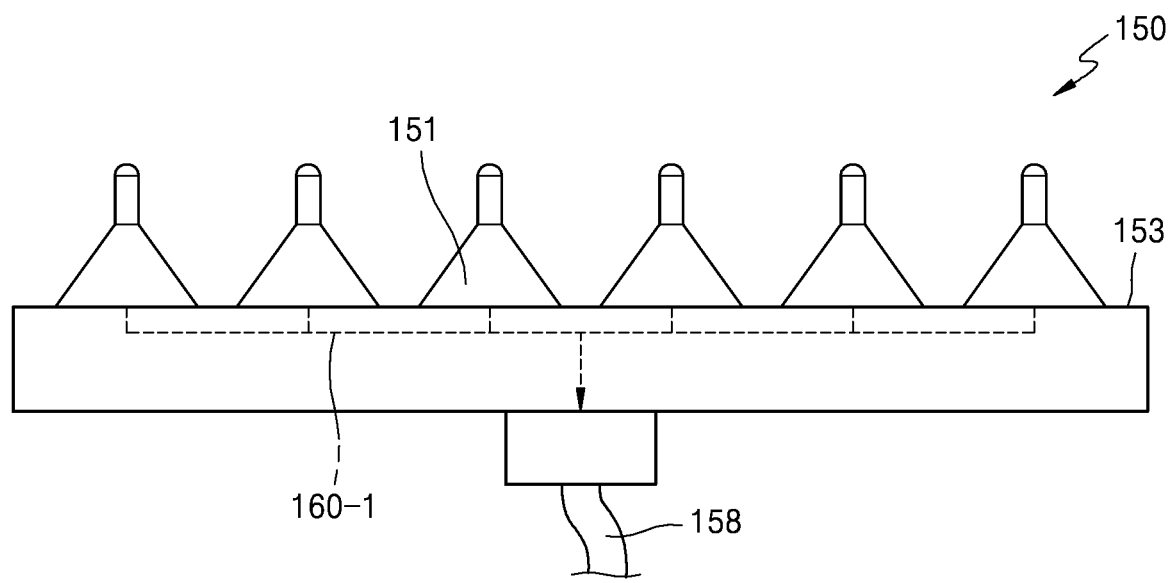
FIGS. 24A through 24D are block diagrams of wirings or sensor circuits in the electrode supporter of the sensor module according to exemplary embodiments.

FIG. 24A is a block diagram of a wiring circuit 160-1 in the electrode supporter 153 of the sensor module 150. Referring to FIG. 24A, the sensor module 150 includes the electrode supporter 153, and the plurality of sensor electrodes 151 that are provided on the electrode supporter 153. The electrode supporter 153 may be formed of a non-conductive material. For example, the electrode supporter 153 may be formed of, for example, a plastic resin. The wiring circuit 160-1 electrically connected to the sensor electrodes 151 may be buried in the electrode supporter 153, or may be formed as a printed circuit on a surface of the electrode supporter 153 on which the sensor electrodes 151 are provided or a rear surface that is opposite to the surface on which the sensor electrodes 151 are provided. The wiring circuit 160-1 may commonly connect the sensor electrodes 151, may sum bioelectrical signals measured by the sensor electrodes 151, and may output the summed bioelectrical signals through the cable 158. For example, the wiring circuit 160-1 may connect the sensor electrodes 151 in series and may sum voltages of measured bioelectrical signals. Alternatively, the wiring circuit 160-1 may connect the sensor electrodes 151 in parallel and may sum currents of measured bioelectrical signals. In this case, output bioelectrical signals may be analog signals. Since bioelectrical signals measured by the plurality of sensor electrodes 151 are all summed, detection signals of the bioelectrical signals that are weak may be further enhanced. Alternatively, the sensor electrodes 151 may be individually connected to the wiring circuit 160-1 or may be grouped and then connected to the wiring circuit 160-1, and bioelectrical signals measured by the sensor electrodes 151 may be individually output to the outside or may be grouped and summed and then output to the outside. Since analog bioelectrical signals are output through the cable 158 in FIG. 24A, an additional power line or an additional line for driving a circuit is not necessary.

Figure 24B:
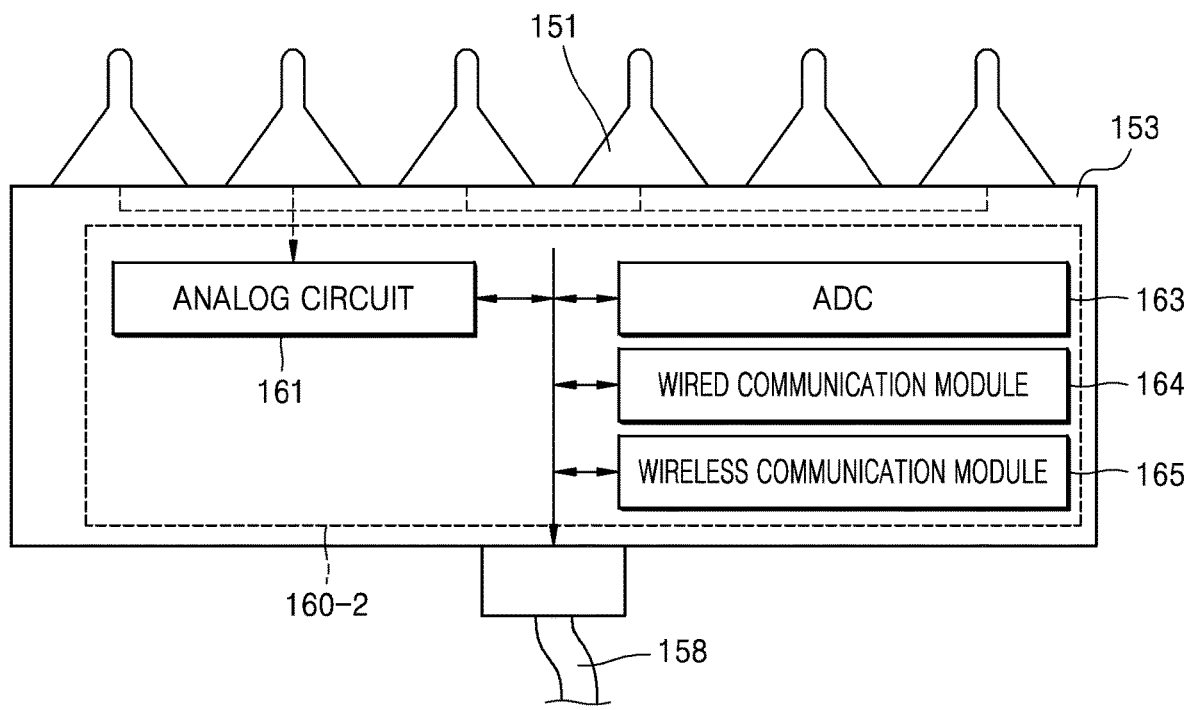

FIG. 24B is a block diagram of a sensor circuit 160-2 of the sensor module 150 according to another exemplary embodiment.

Referring to FIG. 24B, the sensor circuit 160-2 may include the analog circuit 161, an ADC 163, and a wired communication module 164, and may further include a wireless communication module 165. The wireless communication module 165 may be a module using, for example, but not limited to, wireless LAN, Wi-Fi, Bluetooth, ZigBee, WFD, UWB, infrared communication, BLE, or NFC. The wired communication module 164 or the wireless communication module 165 may selectively transmit bioelectrical signals detected by the sensor electrodes 151 to the main body 110 or an external electronic device in a wired or wireless manner. The sensor circuit 160-2 may include only the wireless communication module 165, without the wired communication module.

Figure 24C:
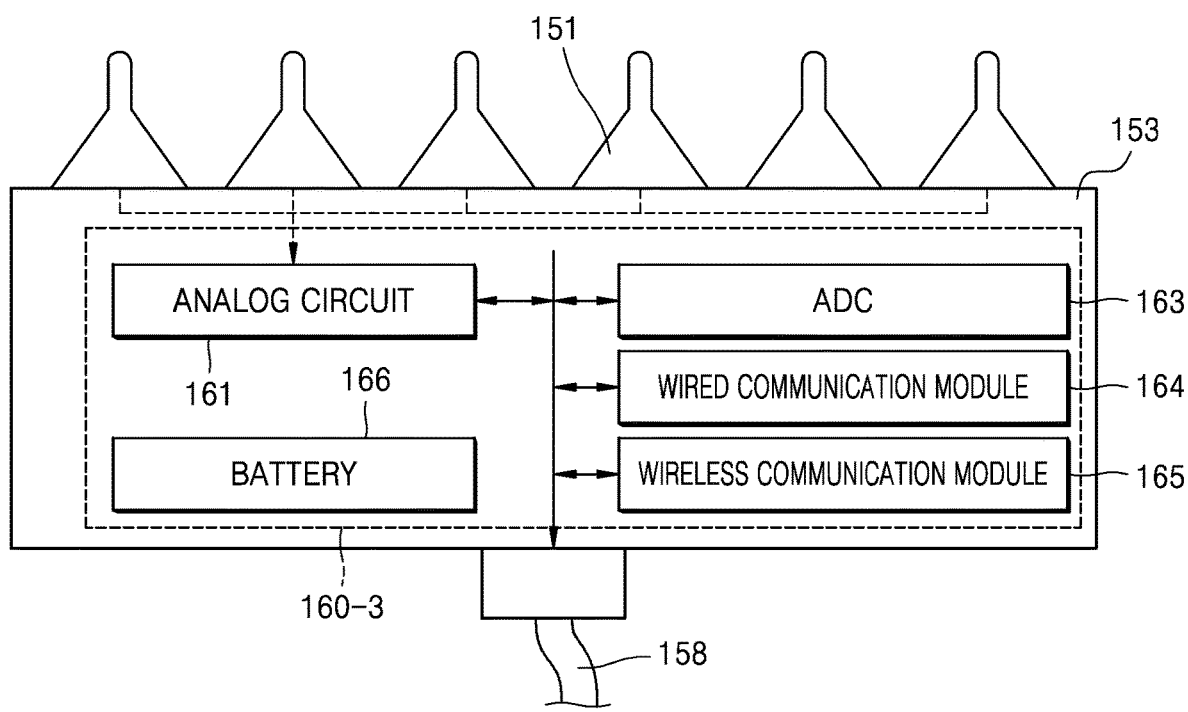

FIG. 24C is a block diagram of a sensor circuit 160-3 of the sensor module 150 according to another exemplary embodiment. Referring to FIG. 24C, the sensor circuit 160-3 may include the analog circuit 161, the ADC 163, the wired communication module 164, and the wireless communication module 165, and may further include a battery 166. In this case, a power line of the cable 158 may be omitted. Alternatively, a power line may be provided in the cable 158 and the battery 166 may be used as an auxiliary member.

Figure 24D:
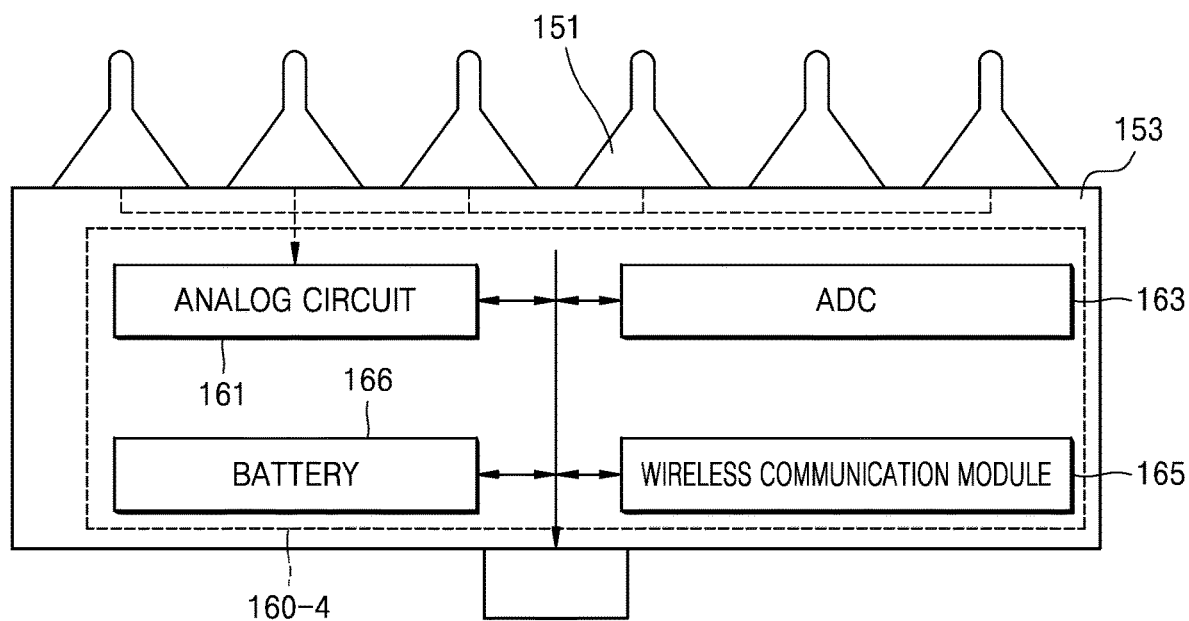

FIG. 24D is a block diagram of a sensor circuit 160-4 of the sensor module 150 according to another exemplary embodiment. Referring to FIG. 24D, the sensor circuit 160-4 may include the analog amplification circuit 161, the ADC 163, the wireless communication module 165, and the battery 166, and may omit a wired communication module. In this case, the sensor module 150 communicates with the main body 110 or an external electronic device in a wireless manner through the wireless communication module 165 without using a cable. The sensor circuit 160-4 may include, additionally or instead of a battery, a wireless power module that wirelessly receives power or an energy harvest module that harvests as energy a movement of the head 1 to which the apparatus 100 is attached.

Although a digital circuit is provided in the sensor module 150 in FIGS. 24B through 24D, the digital circuit may be omitted and only the analog circuit 161 may be provided. In this case, the cable 158 may include a line for transmitting amplified analog signals, a source (Vcc) line and a ground (GND) line for supply power to drive the analog circuit 161, and a reference signal line.

Figure 25:
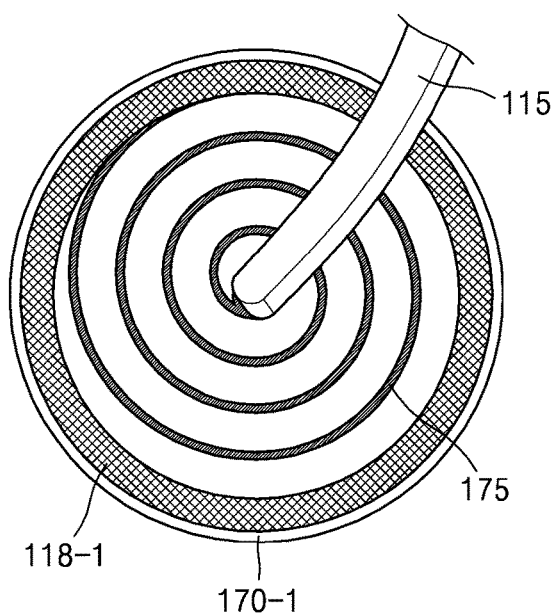
FIG. 25 is a view of a reference electrode provided on an ear insertion ring of an apparatus for measuring bioelectrical signals, according to another exemplary embodiment.

FIG. 25 is a view of a reference electrode 170-1 provided on the apparatus 100 according to another exemplary embodiment. Referring to FIG. 25, the apparatus 100 may further include a sensor support 175 that connects the ear connection ring 115 and an ear insertion ring 118-1 and elastically supports the reference electrode 170-1 so that the reference electrode 170-1 moves in 3-axis directions. The reference electrode 170-1 having a ring shape is attached to the ear insertion ring 118-1. That is, the ear insertion ring 118-1 may be understood as an electrode supporter for the reference electrode 170-1. The sensor support 175 may have a spiral spring shape similar to that of the spiral spring 121 of FIG. 11, and one inner end of the spiral spring shape is coupled to one end of the ear connection ring 115 and the other outer end of the spiral spring shape is coupled to the ear insertion ring 118-1. Accordingly, the reference electrode 170-1 may be elastically supported by the sensor support 175 so that the reference electrode 170-1 moves in 3-axis directions, and the reference electrode 170-1 may be stably inserted into the external part of the ear 5 even as the main body 110 moves. Instead of the reference electrode 170-1, a ground electrode may be provided on the ear insertion ring 118-1.

Figure 26:
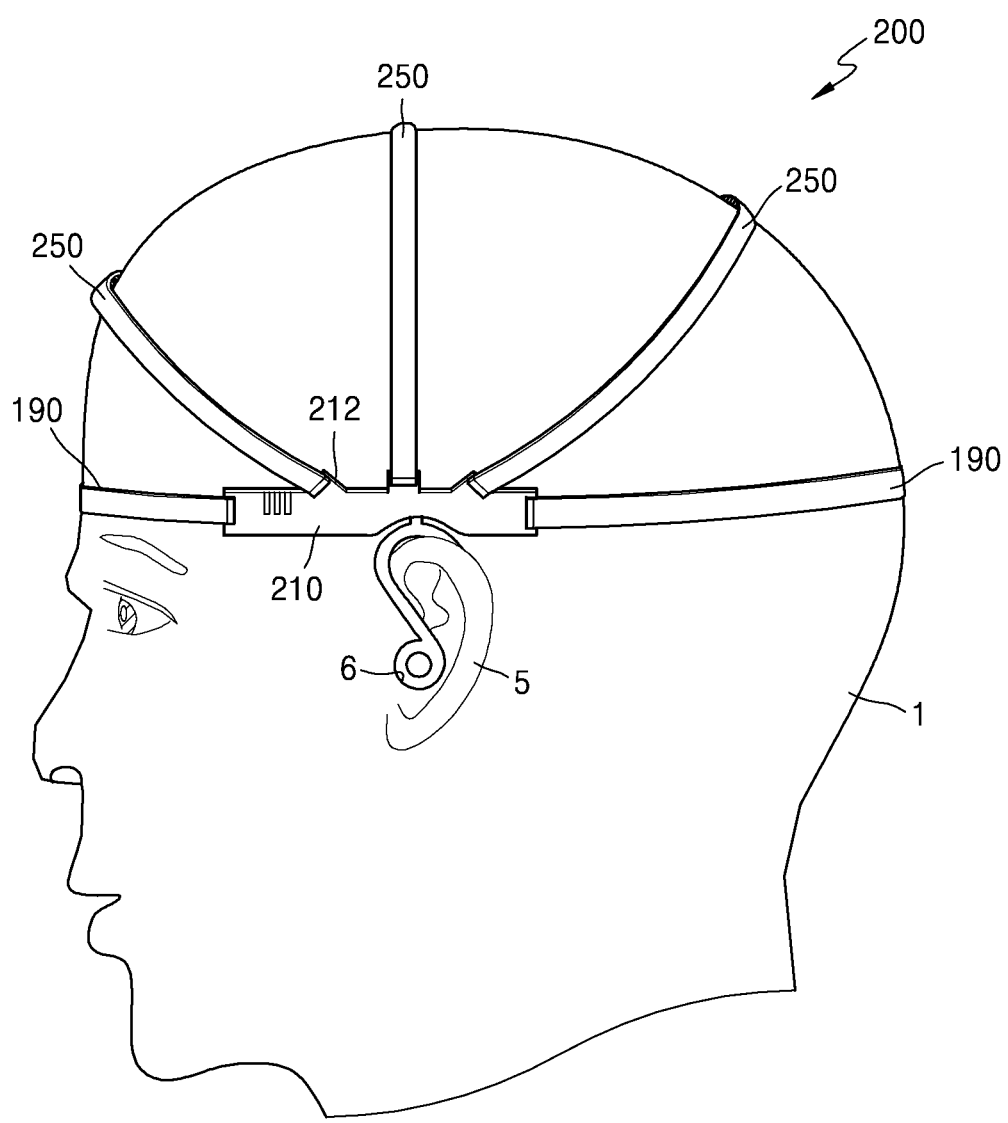
FIG. 26 is a view of an apparatus for measuring bioelectrical signals according to another exemplary embodiment.
Figure 27:
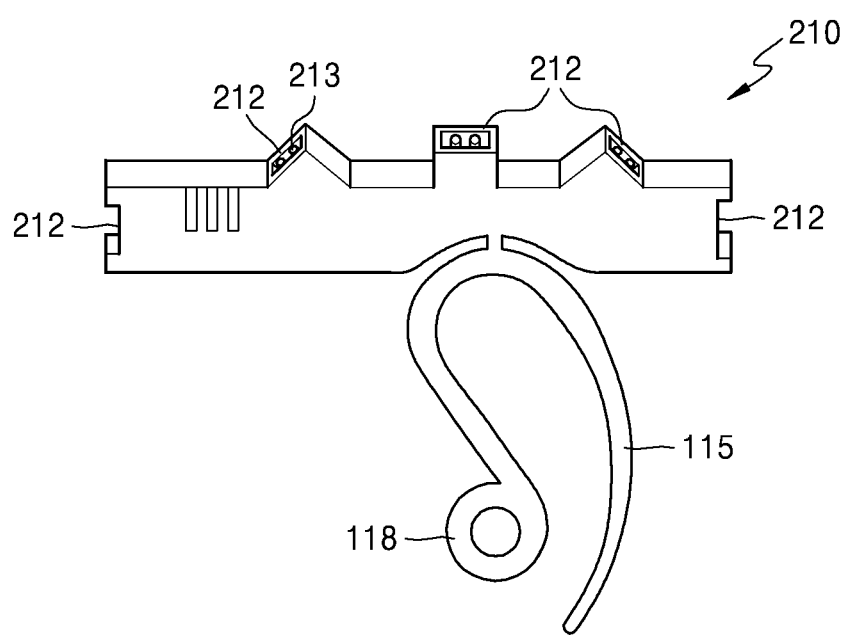
FIG. 27 is a view of a main body of the apparatus of FIG. 26.
Figure 28:
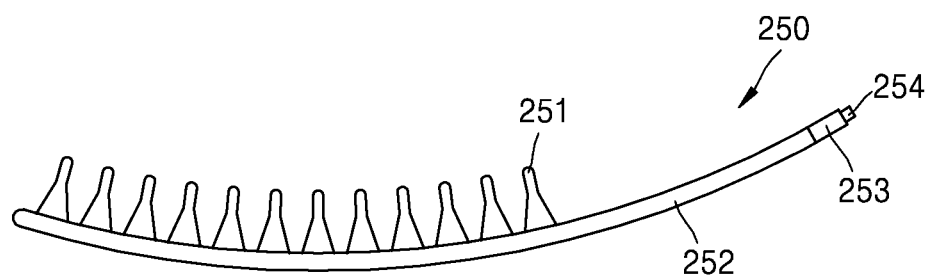
FIG. 28 is a view of a sensor module of the apparatus of FIG. 26.

FIG. 26 is a view of an apparatus 200 for measuring bioelectrical signals according to another exemplary embodiment. FIG. 27 is a view of a main body 210 of the apparatus 200 of the present exemplary embodiment. FIG. 28 is a view of a sensor module 250 of the apparatus 200 of the present exemplary embodiment.

Referring to FIGS. 26 through 28, the apparatus 200 of the present exemplary embodiment is substantially the same as the apparatus 100 of FIGS. 1 through 16 except the sensor module 250 and a connection frame structure, and thus the following will focus on the difference.

The apparatus 200 includes the main body 210 in the form of an earset and the sensor module 250 detachably coupled to the main body 210.

The main circuit 140 (see FIG. 16) for processing bioelectrical signals obtained by the sensor module 250 may be embedded in the main body 210. A plurality of slots 212 may be formed in the main body 210, and one end 253 of the sensor module 250 (see FIG. 28) may be detachably inserted into one of the slots 212. The slots 212 may be arranged in a plurality of directions about the ear 5 of the head 1 as shown in FIG. 26. The main body 210 may further include the ear connection ring 115 that is fixed to the ear 5 of the person, and the ear insertion ring 118 that is inserted into the external part of the ear 5 and more stably fixes the main body 210 to the ear 5. A reference electrode and/or a ground electrode may be provided on the ear insertion ring 118. A connector terminal 213 is provided in each of the slots 212.

Referring to FIG. 28, the sensor module 25 includes sensor electrodes 251 and an electrode supporter 252. The electrode supporter 252 may have a bar shape that longitudinally and curvedly extend to conform to a curved shape of the head 1. The sensor electrodes 251 may be disposed on one surface of the electrode supporter 252. Each of the plurality of sensor electrodes 251 may include a tapering portion having a circular cone shape, an elliptic cone shape, or a polypyramid shape and a protruding portion having a cylindrical shape or a prism shape.

The sensor circuit (see any of FIGS. 10, and 24A through 24D) may be provided in the electrode supporter 252. A connector terminal 254 is exposed through the one end 253 of the sensor module 250. The connector terminal 254 may include a power supply connector terminal and/or a signal connector terminal. When the one end 253 of the sensor module 250 is inserted into the slot 212 of the main body 210, a connector terminal 213 in the slot 212 and the connector terminal 254 are electrically connected to each other.

Figure 29:
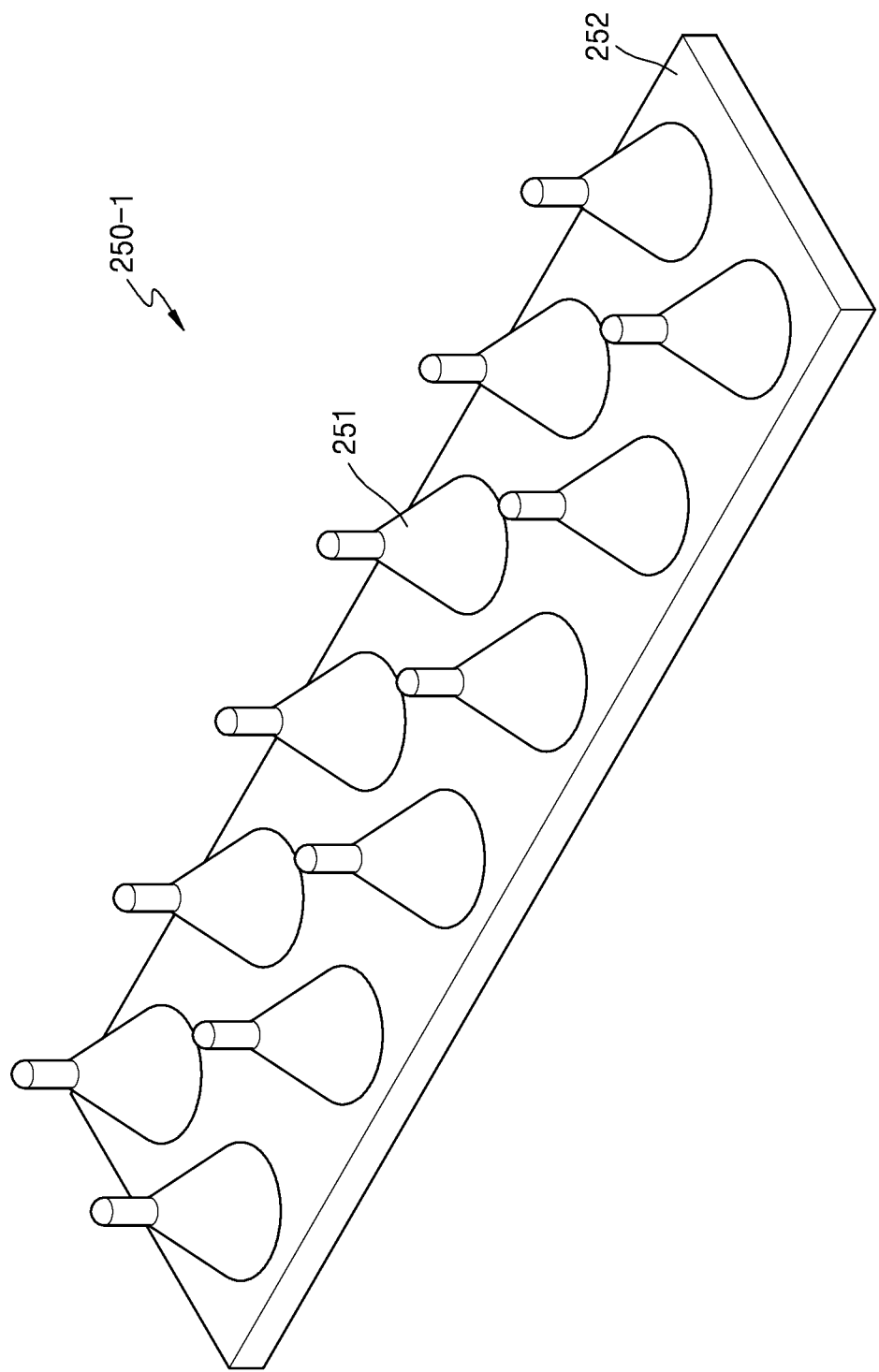
FIG. 29 is a view illustrating an arrangement of sensor electrodes provided on a sensor module, according to an exemplary embodiment.

FIG. 29 is a view illustrating an arrangement of the sensor electrodes 251 provided on a sensor module 250-1. As shown in FIG. 29, the sensor electrodes 251 may each include a tapering portion having a circular cone shape and a protruding portion having a cylindrical shape, and may be arranged in two or more columns in a longitudinal direction of the electrode supporter 252.

Figure 30:
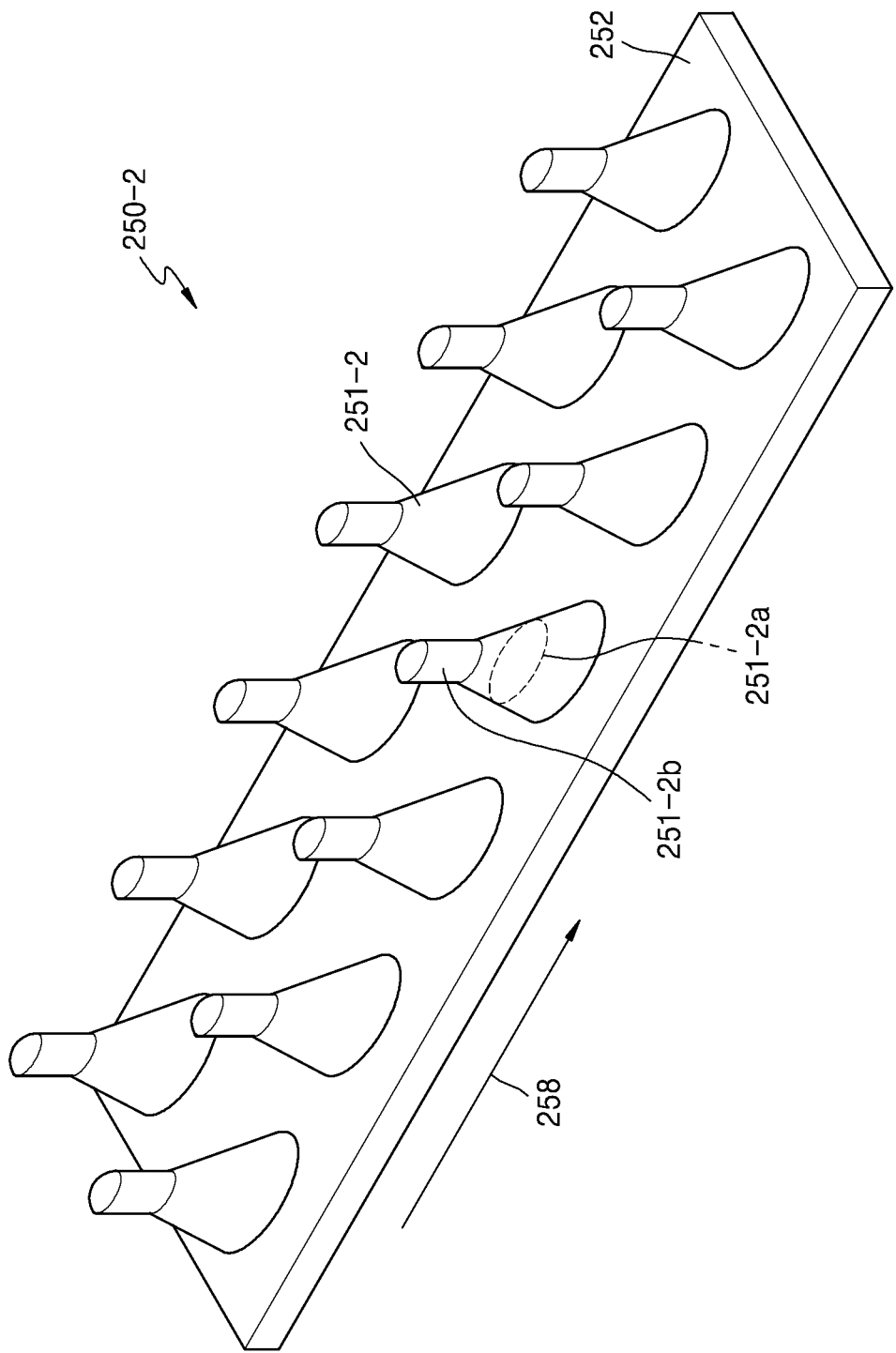
FIG. 30 is a view of sensor electrodes provided on a sensor module, according to another exemplary embodiment.
Figure 31:
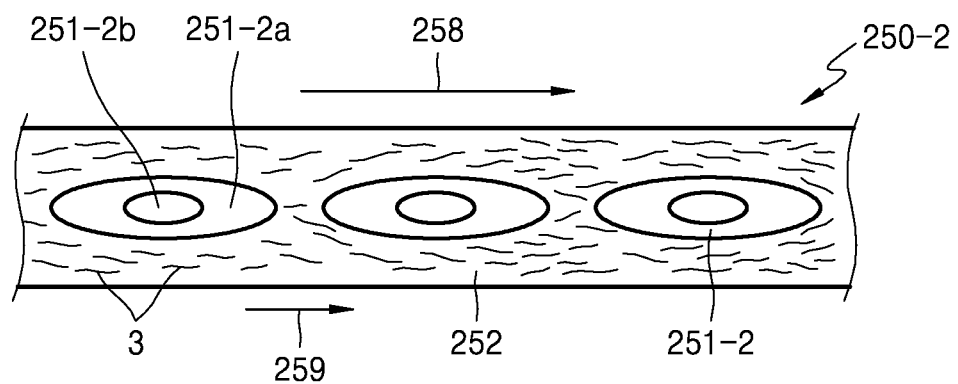
FIG. 31 is a view illustrating a case where the sensor module of FIG. 30 is attached to the scalp.

FIG. 30 is a view of sensor electrodes 251-2 provided on a sensor module 250-2 according to another exemplary embodiment. FIG. 31 is a view illustrating a case where the sensor module 250-2 of FIG. 30 is attached to the scalp.

Referring to FIG. 30, the sensor module 250-2 of the present exemplary embodiment includes the electrode supporter 252 and the plurality of sensor electrodes 251-2 provided on the electrode supporter 252. Each of the sensor electrodes 251-2 may include a tapering portion 251-2a and a protruding portion 251-2b each having an elliptic cone shape as described with reference to FIG. 17A. The sensor electrodes 251-2 may be arranged in one or more columns in one direction 258 on the electrode supporter 252. Hereinafter, the direction 258 in which the sensor electrodes 251-2 are arranged will be referred to as an arrangement direction. The sensor electrodes 251-2 are arranged so that long axes of cross-sections of the tapering portions 251-2a having elliptic cone shapes are parallel to the arrangement direction 258.

Referring to FIG. 31, since the sensor electrodes 251-2 of the sensor module 250-2 are arranged so that the long axes of the cross-sections of the tapering portions 251-2 having elliptic cone shapes are parallel to the arrangement direction 258, as shown in FIG. 31, widths of the tapering portions 251-2a having elliptic cone shapes of the sensor electrodes 251-2 in a direction perpendicular to the arrangement direction 258 are less than widths of the tapering portions 251-2a in a direction parallel to the arrangement direction 258. Accordingly, since the hairs 3 of the scalp are distributed in a direction 259, the sensor module 250-2 may be worn in consideration of the direction 259 of the hairs 3. For example, when the sensor module 250-2 is worn on the scalp so that the arrangement direction 258 of the sensor electrodes 251-2 is parallel to the direction 259 of the hairs 3, the sensor electrodes 251-2 of the sensor module 250-2 may easily pass through the hairs 3 that are densely distributed to reach the scalp. Also, since the sensor electrodes 251-2 have funnel shapes including the tapering portions 251-2a and the protruding portions 251-2b having elliptic cone shapes and thus the hairs 3 may be located in wide spaces between the tapering portions 251-2a having elliptic cone shapes, the protruding portions 251-2b of the sensor electrodes 251-2 may easily contact the scalp. Also, when the sensor electrodes 251-2 are pressed toward the scalp, the protruding portions 251-2b are bent as described above, thereby increasing contact areas between the sensor electrodes 251-2 and the scalp.

Although the sensor electrodes 251-2 are arranged so that the long axes of the cross-sections of the tapering portions 251-2a having elliptic cone shapes are parallel to the arrangement direction 258 in the present exemplary embodiment, the inventive concept is not limited thereto.

Figure 32:
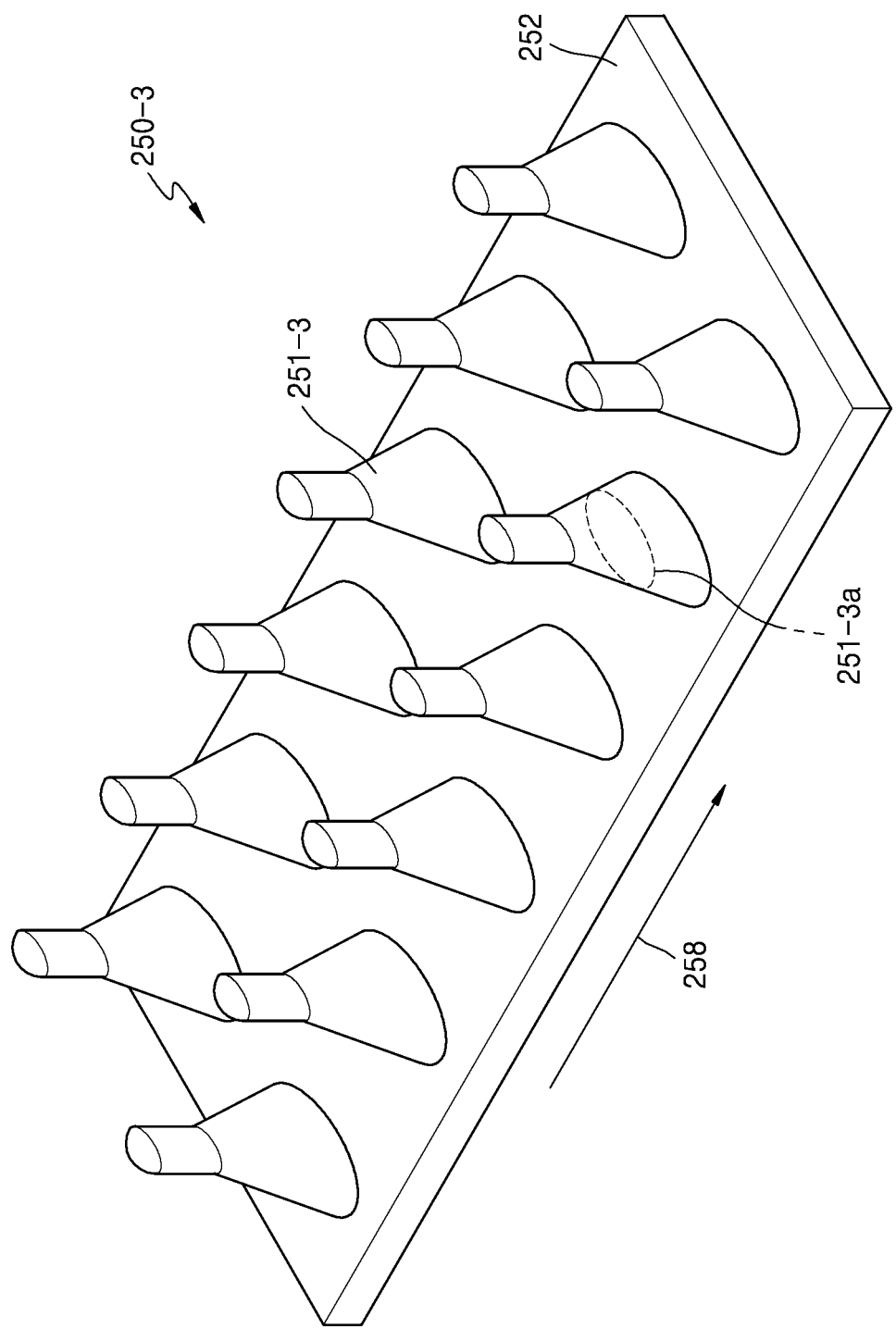
FIG. 32 is a view of a sensor electrode provided on a sensor module according to another exemplary embodiment.
Figure 33:
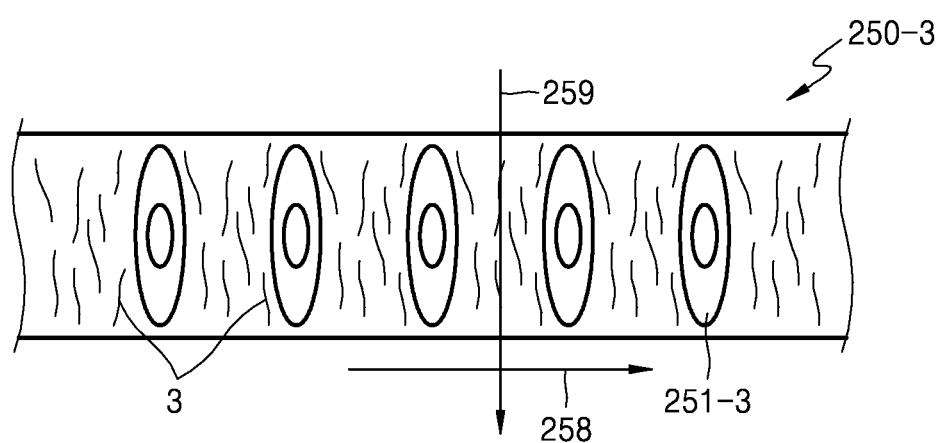
FIG. 33 is a view illustrating a case where the sensor module of FIG. 32 is attached to the scalp.

FIG. 32 is a view of a sensor module 250-3 according to another exemplary embodiment. FIG. 33 is a view illustrating a case where the sensor module 250-3 of FIG. 32 is attached to the scalp. Referring to FIG. 32, sensor electrodes 251-3 of the sensor module 250-3 may be arranged on the electrode supporter 252 so that long axes of cross-sections of tapering portions 251-3a having elliptic cone shapes are perpendicular to the arrangement direction 258. That is, widths of the tapering portions 251-3a having elliptic cone shapes of the sensor electrodes 251-3 in a direction parallel to the arrangement direction 258 may be less than widths of the tapering portions 251-3a in a direction perpendicular to the arrangement direction 258. Accordingly, when the sensor module 250-3 is worn on the scalp so that the arrangement direction 258 of the sensor electrodes 251-3 is perpendicular to the direction 259 of the hairs 3, the sensor electrodes 250-3 may easily pass through the hairs 3 that are densely distributed to reach the scalp due to shapes and an arrangement of the sensor electrodes 251-3.

Figure 34:
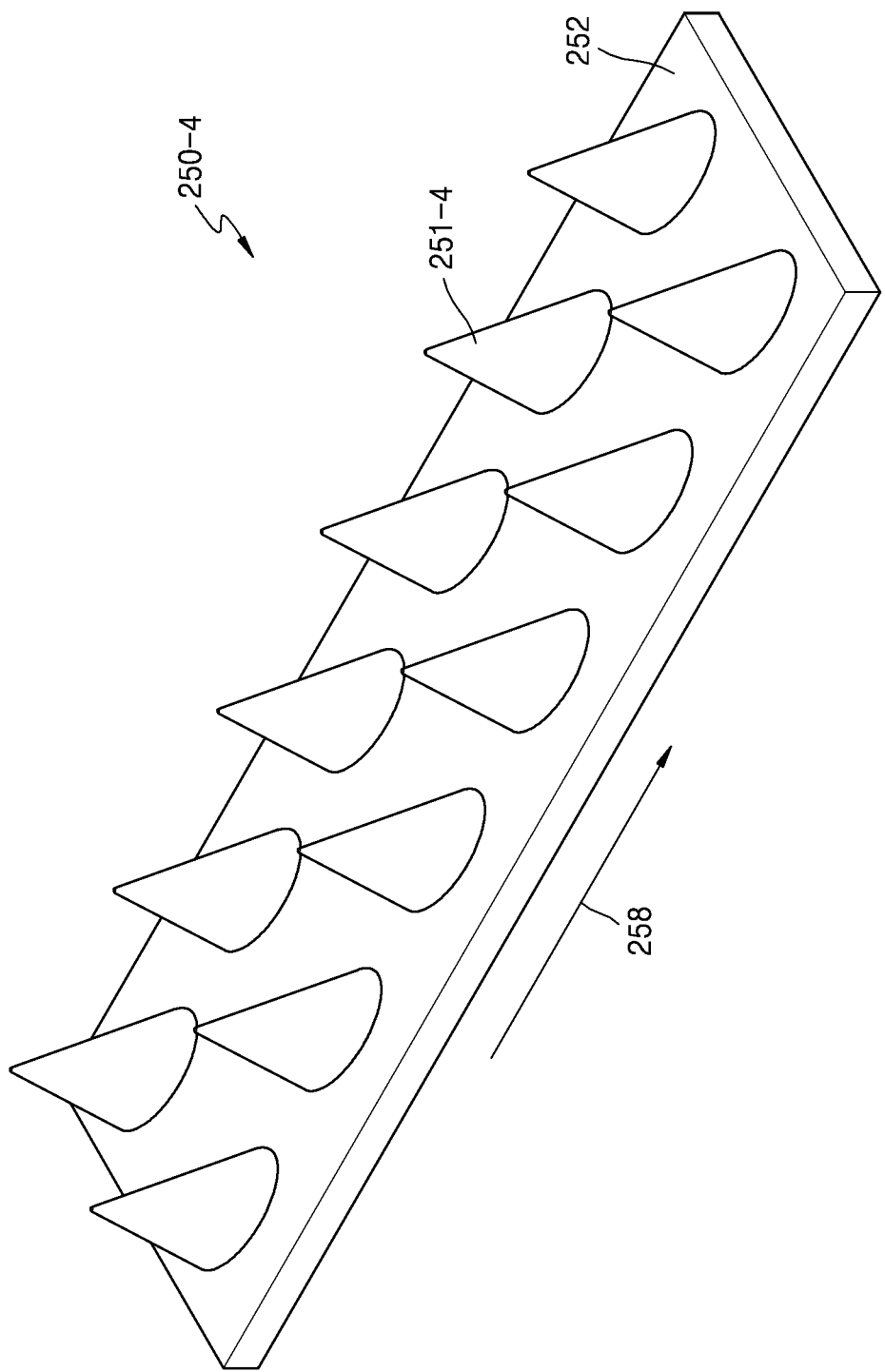
FIG. 34 is a view of a sensor electrode provided on a sensor module, according to another exemplary embodiment.

Also, although the sensor electrodes of the sensor module each include a tapering portion and a protruding portion in FIGS. 29 through 33, the inventive concept is not limited thereto. FIG. 34 is a view of a sensor module 250-4 for measuring bioelectrical signals according to another exemplary embodiment. Referring to FIG. 34, the sensor module 250-4 may include sensor electrodes 251-4 arranged on the electrode supporter 252, and the sensor electrodes 251-4 may each include only a tapering portion having an elliptic cone shape without a protruding portion as described with reference to FIG. 19A and may be arranged so that long axes of cross-sections are parallel or perpendicular to the arrangement direction 258. Alternatively, cross-sections of the sensor electrodes 251-4 may have streamlined shapes as described with reference to FIG. 20, and the sensor electrodes 251-4 may be arranged so that longitudinal directions of the streamlined shapes are parallel or perpendicular to the arrangement direction 258. Alternatively, the plurality of sensor electrodes 251-4 may be individually arranged so that long axes of cross-sections are parallel to the direction 259 of the hairs 3 of the living body.

Although the apparatus 100 is fixed to the head 1 by using the auxiliary frame 190 having a hair band shape in FIGS. 1 and 15, the inventive concept is not limited thereto.

Figure 35A:
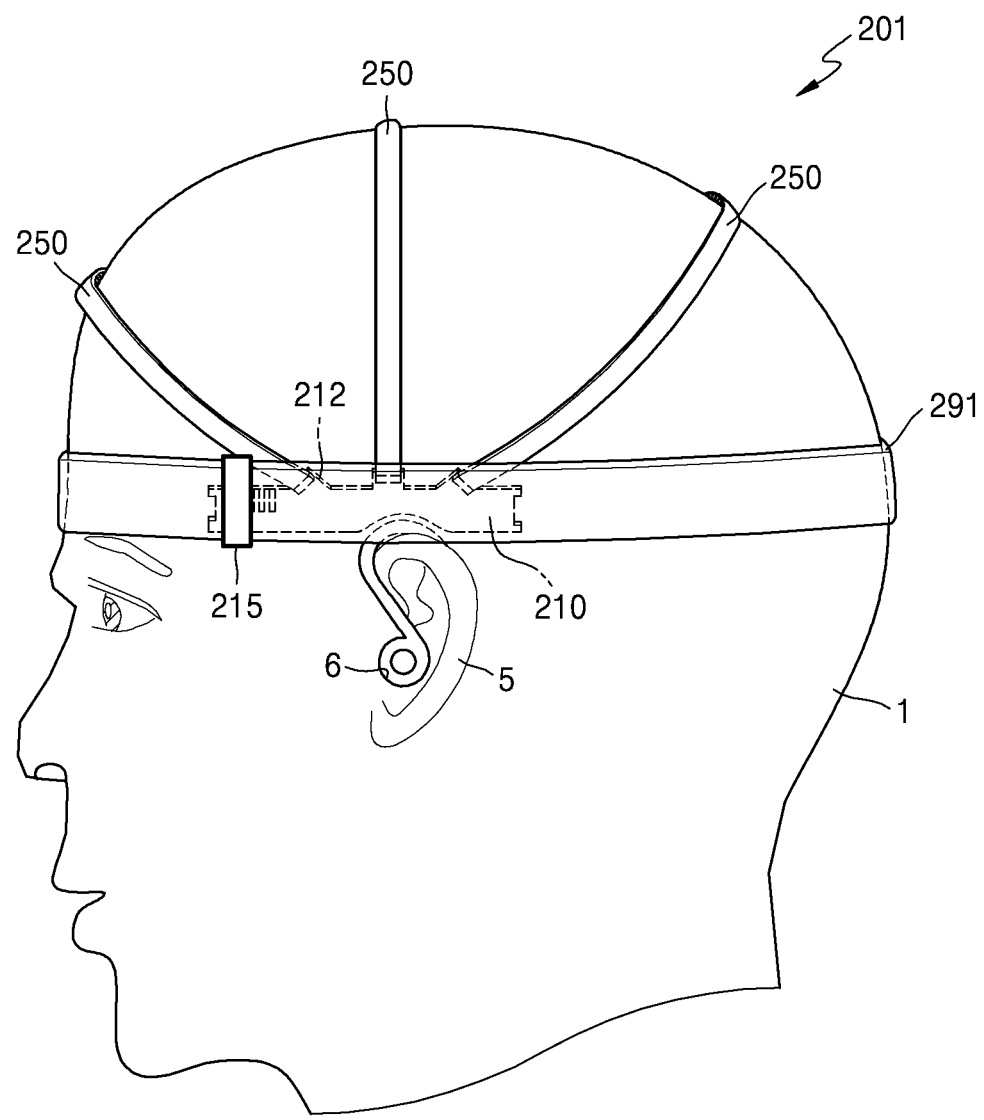
FIGS. 35A and 35B are views of an apparatus for measuring bioelectrical signals, according to another exemplary embodiment.

FIG. 35A is a view of an apparatus 201 for measuring bioelectrical signals according to another exemplary embodiment. Referring to FIG. 35A, the apparatus 201 may be fixed to the head 1 by using a hair band 291. An attachment/detachment coupler 215 may be provided on the main body 210 and/or the hair band 291 of the apparatus 201 to be attached/detached to/from the main body 210. The hair band 291 may be fixed to the main body 210.

Figure 35B:
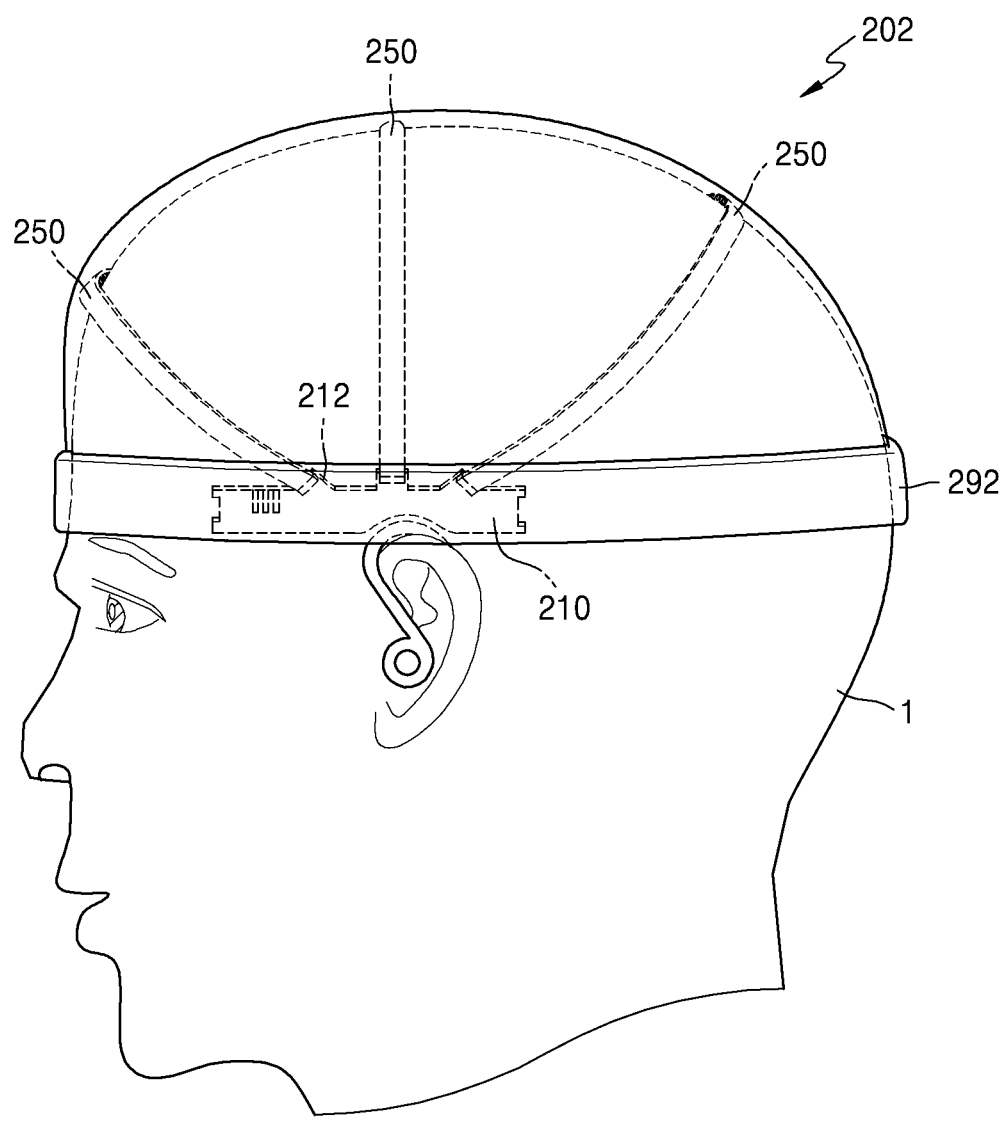

FIG. 35B is a view of an apparatus 202 for measuring bioelectrical signals according to another exemplary embodiment. Referring to FIG. 35B, the apparatus 202 may be fixed to the head 1 by using a cap 292. A fixing member (not shown) for fixing the main body 210 may be provided on an inner surface of the cap 292. The fixing member may have a detachable structure. Furthermore, a fixing member (not shown) for fixing a position of the sensor module 250 may be additionally provided on the inner surface of the cap 292. Since the main body 210 is fixed by using the cap 292, the main body 210 may be less affected by an external condition. For example, the apparatus 202 of the present exemplary embodiment may stably measure brain waves while a user sleeps.

Figure 36:
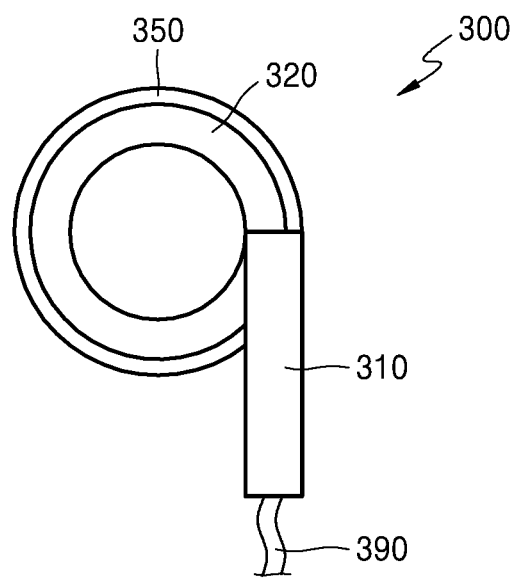
FIG. 36 is a view of an apparatus for measuring bioelectrical signals, according to another exemplary embodiment.
Figure 37:
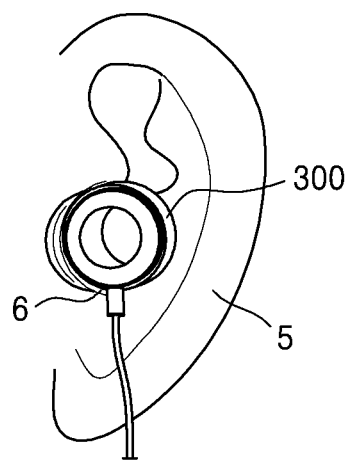
FIG. 37 is a view illustrating a case where the apparatus of FIG. 36 is inserted into an external part of an ear.

FIG. 36 is a view of an apparatus 300 for measuring bioelectrical signals according to another exemplary embodiment. FIG. 37 is a view illustrating a case where the apparatus 300 is inserted into an external part 6 of the ear 5. Referring to FIGS. 36 and 37, the apparatus 300 includes a sensor holder 320 that is inserted into the external part 6 of the ear 5 and a sensor electrode 350 that is provided on the sensor holder 320. The apparatus 300 may have an earphone shape. For example, the sensor holder 320 may have a cylindrical shape that may be inserted into the external part 6. The sensor electrode 350 may have a circular ring shape that surrounds an outer circumferential surface of the sensor holder 320. The sensor electrode 350 contacts the skin of the external part 6 and detects bioelectrical signals. Hollow portions may be formed in the sensor holder 320 and the sensor electrode 350 and external sound may be input to the ear 5. The apparatus 300 may further include an extending support portion 310 that supports the sensor holder 320 and is exposed through the auricle of the ear 5 and a cable 390 that is connected to the extending support portion 310. The sensor holder 320 and the extending support portion 310 may be integrally formed with each other or the sensor holder 320 may be fixed to the extending support portion 310. The sensor circuit (see any of FIG. 10, and FIGS. 24A through 24D) for processing bioelectrical signals measured by the sensor electrode 350 and/or the main circuit 140 (see FIG. 16) may be provided in the extending support portion 310. The apparatus 300 may be provided on an earphone that outputs a sound.

Figure 38:
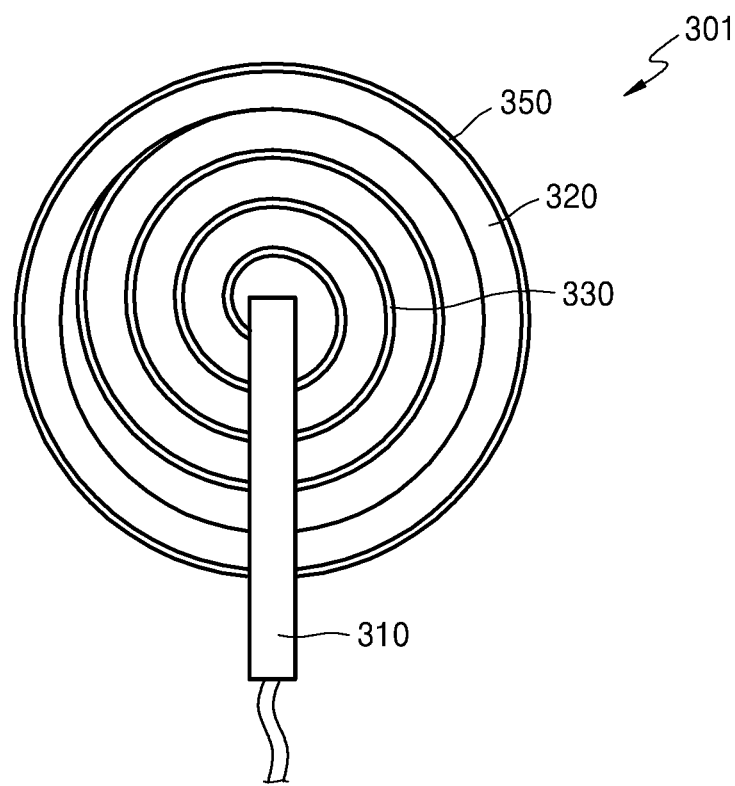
FIG. 38 is a view of an apparatus for measuring bioelectrical signals, according to another exemplary embodiment.
Figure 39:
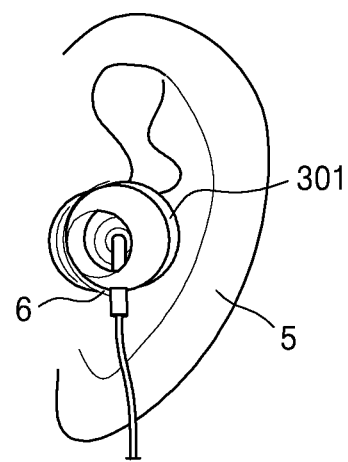
FIG. 39 is a view illustrating a case where the apparatus of FIG. 38 is inserted into an external part of an ear.

Although the sensor holder 320 is fixed to the extending support portion 310 in the present exemplary embodiment, the inventive concept is not limited thereto. FIG. 38 is a view of an apparatus 301 for measuring bioelectrical signals according to another exemplary embodiment. FIG. 39 is a view illustrating a case where the apparatus 301 of FIG. 38 is inserted into the external part 6 of the ear 5. Referring to FIGS. 38 and 39, the apparatus 301 may further include a sensor support 330 that is disposed between the sensor holder 320 and the extending support portion 310 and elastically supports the sensor electrode 350 so that the sensor electrode 350 independently moves in 3-axis directions. The sensor support 330 may have a spiral spring shape similar to that of the spiral spring of FIG. 11 or 25. That is, one inner end of the spiral spring shape is coupled to the extending support portion 310 and the other outer end of the spiral spring shape is coupled to the sensor holder 320. Accordingly, since the sensor electrode 350 is elastically supported by the sensor support 330 to move in 3-axis directions, even when the extending support portion 310 slightly moves, the sensor electrode 350 may stably contact the skin of the external part 6 of the ear 5.

Figure 40:
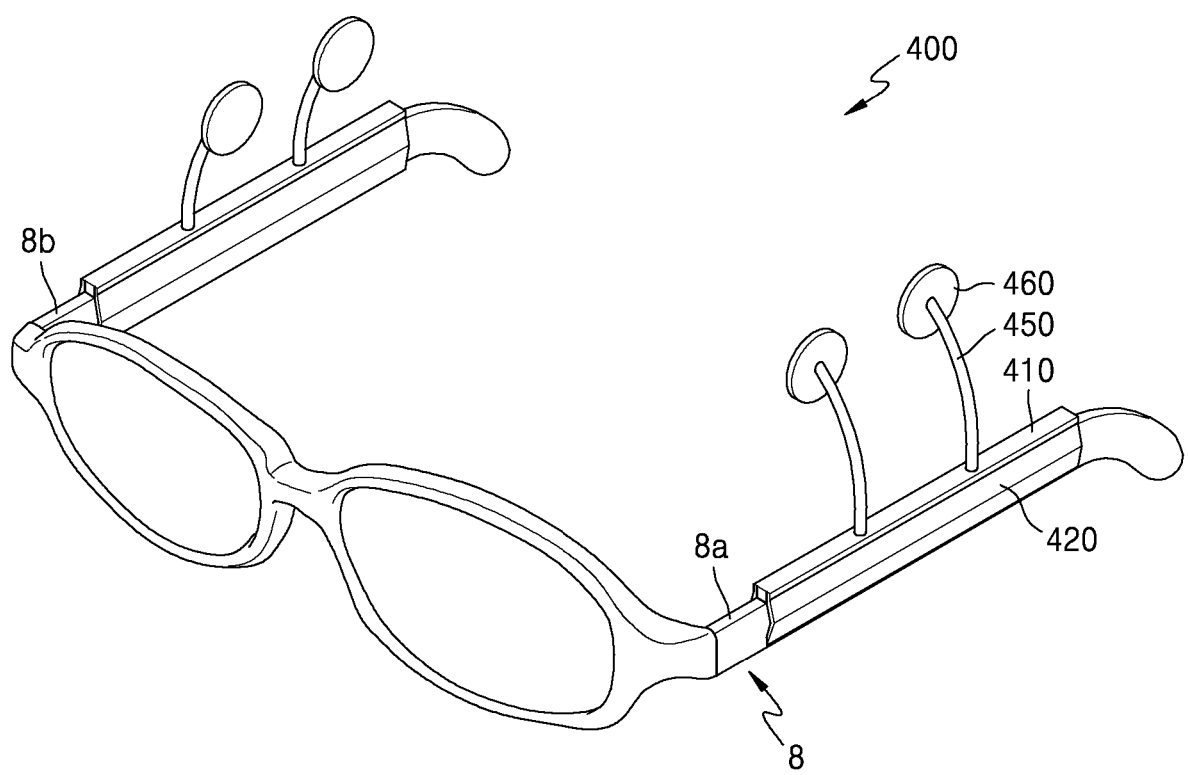
FIG. 40 is a view of an apparatus for measuring bioelectrical signals, according to another exemplary embodiment.
Figure 41A:
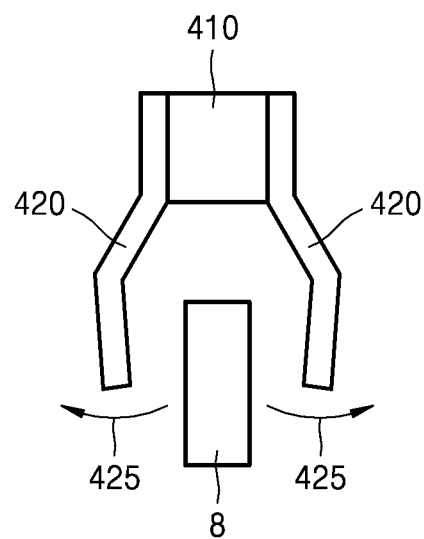
FIGS. 41A and 41B are views of an attachment/detachment coupler of the apparatus of FIG. 40, according to an exemplary embodiment.
Figure 41B:
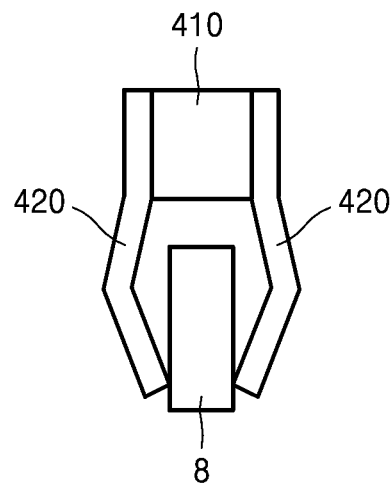

FIG. 40 is a view of an apparatus 400 for measuring bioelectrical signals according to another exemplary embodiment. FIGS. 41A and 41B are views of an attachment/detachment coupler 420 of the apparatus 400 of FIG. 40.

The apparatus 400 of the present exemplary embodiment includes a main body 410 that is coupled to each leg 8 of glasses (referred to as glasses leg 8), a connection frame 450 that extends from the main body 410, and a sensor module 460 that is provided on the connection frame 450 and measures bioelectrical signals. The apparatus 400 is provided on each of left and right glasses legs 8a and 8b and measures bioelectrical signals of a living body who wears the glasses.

The apparatus 400 may further include the attachment/detachment coupler 420 that enables the main body 410 to be detachably attached/detached to/from the glasses.

The main body 410 is provided over each glasses leg 8. The connection frame 450 has a curved bar shape that longitudinally extends upward from the main body 410 to closely contact the skin of the living body about the ear of the living body. The connection frame 450 may be integrally coupled to the main body 410 or may be detachably coupled to the main body 410. The main body 410 and/or the connection frame 450 may be customized by using, for example, a 3D printer.

The main circuit 140 (see FIG. 16) for processing bioelectrical signals obtained by the sensor module 460 may be embedded in the main body 410.

The sensor module 460 supported by the connection frame 450 may be the same as the sensor module 150 of FIGS. 3 and 4 or modifications of the sensor module 150. For example, the sensor module 460 may include the sensor electrode of any of FIGS. 5, 17A through 17D, and 18 through 20. Alternatively, the sensor module 460 may include a well-known sensor electrode. The sensor circuit 160 (see FIG. 10) for amplifying bioelectrical signals detected by the sensor electrode or converting bioelectrical signals into digital signals may be provided on the sensor module 460.

Furthermore, the sensor support 120 (see FIGS. 3 and 11) that elastically supports the sensor module 460 so that the sensor module 460 moves in 3-axis directions may be further provided between the sensor module 460 and the connection frame 450.

The attachment/detachment coupler 420 may have a clip structure that elastically opens and closes as shown in FIGS. 41A and 41B. Referring to FIG. 41A, the glasses leg 8 may be inserted by increasing an interval between terminal portions of the attachment/detachment coupler 420 in an outward direction 425, and as shown in FIG. 41B, the main body 410 may be fixed to the glasses leg 8 by decreasing the interval between the terminal portions of the attachment/detachment coupler 420.

Figure 42A:
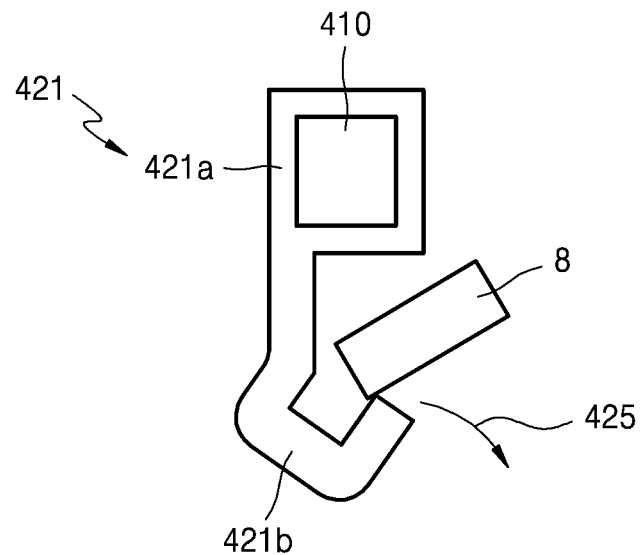
FIGS. 42A and 42B are views of an attachment/detachment coupler of the apparatus of FIG. 40, according to another exemplary embodiment.
Figure 42B:
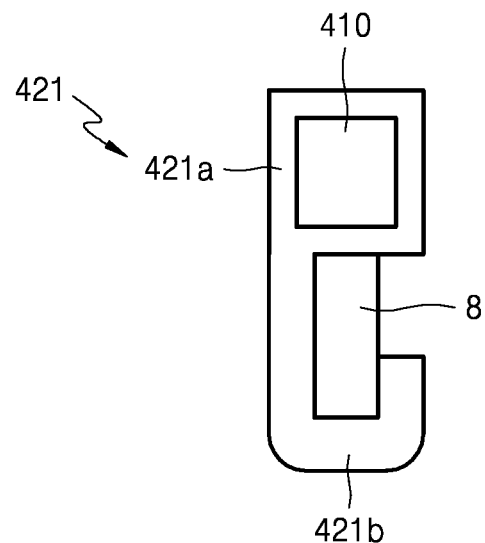

FIGS. 42A and 42B are views of an attachment/detachment coupler 421 of the apparatus 400 of FIG. 40 according to another exemplary embodiment. The attachment/detachment coupler 421 may have an insertion structure including a fixing portion 421a that surrounds and fixes the main body 410 and a groove portion 421b having a groove into which the glasses leg 8 may be inserted as shown in FIGS. 42A and 42B. The attachment/detachment coupler 421 may be formed of a rubber material. Referring to FIG. 42A, the glasses leg 8 may be inserted by bending back the groove portion 421b of the attachment/detachment coupler 421, and as shown in FIG. 42B, the main body 410 may be fixed to the glasses leg 8 by returning the groove portion 421b to its original position.

Figure 43A:
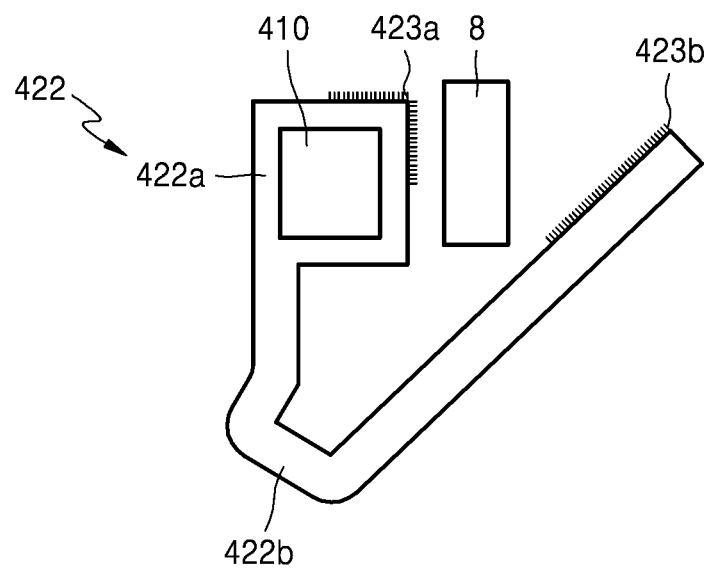
FIGS. 43A and 43B are views of an attachment/detachment coupler of the apparatus of FIG. 40, according to another exemplary embodiment.
Figure 43B:
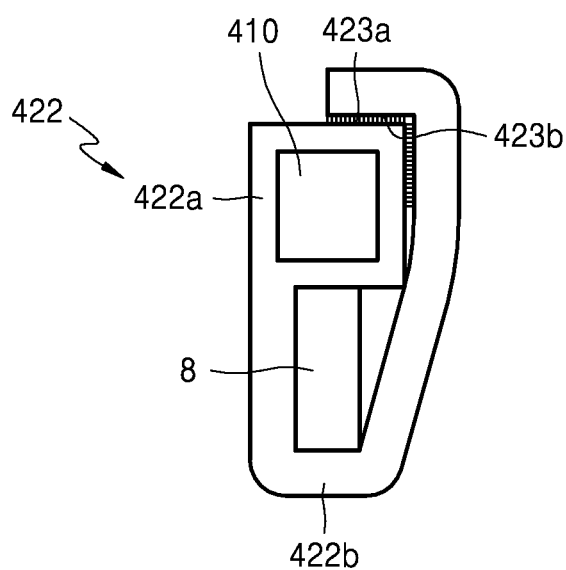

FIGS. 43A and 43B are views of an attachment/detachment coupler 422 of the apparatus 400 of FIG. 40 according to another exemplary embodiment. The attachment/detachment coupler 422 may have a Velcro structure including a fixing portion 422a that surrounds the main body 410 and to which one Velcro 423a is attached and a belt 422b that surrounds the glasses leg 8 and on which another Velcro 423b is provided as shown in FIGS. 43A and 43B. Referring to FIG. 43A, the glasses leg 8 may be inserted by pulling back the belt 422b of the attachment/detachment coupler 422, and as shown in FIG. 43B, the main body 410 may be fixed to the glasses leg 8 by winding the belt 422b and attaching the Velcros 423a and 423b to each other.

Figure 44A:
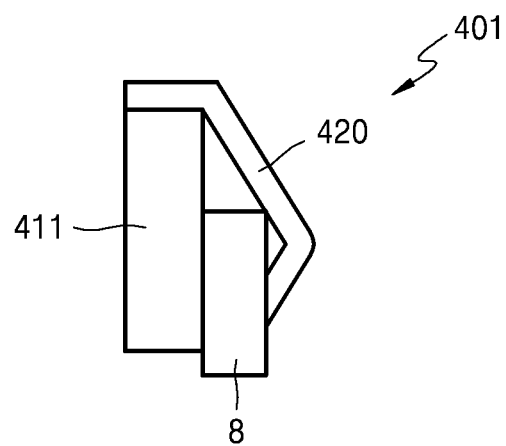
FIGS. 44A through 44C are views of attachment/detachment couplers of an apparatus for measuring bioelectrical signals, according to other exemplary embodiments.
Figure 44B:
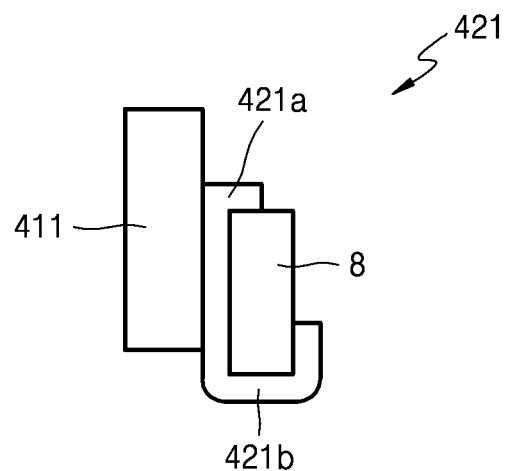
Figure 44C:
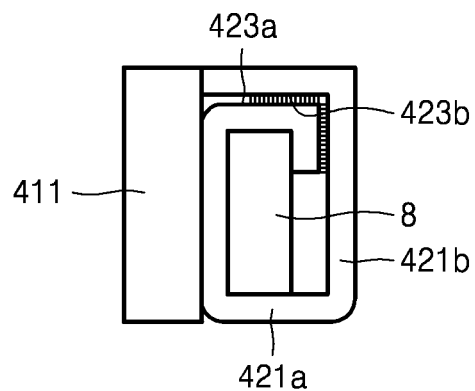

FIGS. 44A through 44C are views of attachment/detachment couplers of an apparatus 401 for measuring bioelectrical signals according to other exemplary embodiments. In the apparatus 401 of FIGS. 44A through 44C, a main body 411 is provided at a side of the glasses leg 8. As shown in FIGS. 44A through 44C, even when the main body 411 is provided at a side of the glasses leg 8, the main body 411 may be fixed to the glasses leg 8 by using the attachment/detachment coupler 420 having a clip structure, the attachment/detachment coupler 421 having an insertion structure, the attachment/detachment coupler 422 having a Velcro structure, or another well-known unit.

Figure 45:
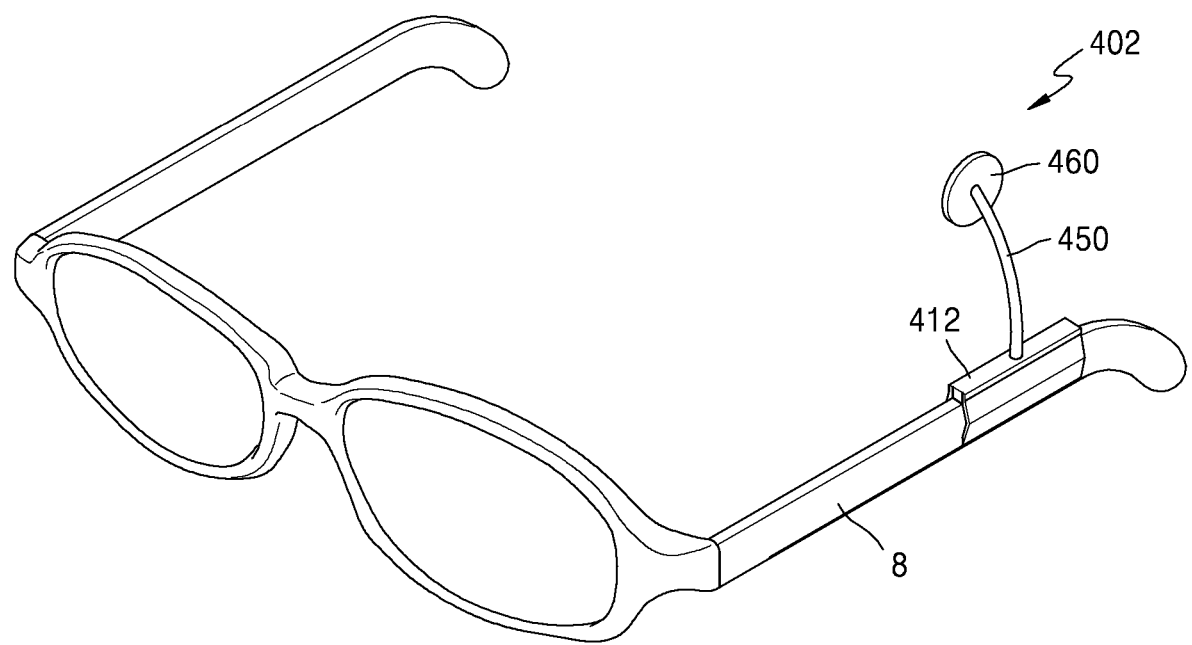
FIG. 45 is a view of an apparatus for measuring bioelectrical signals, according to another exemplary embodiment.

Although the apparatus 400 is provided on each of the left and right glasses legs 8a and 8b in FIG. 40, the inventive concept is not limited thereto. FIG. 45 is a view of an apparatus 402 for measuring bioelectrical signals according to another exemplary embodiment. As shown in FIG. 45, the apparatus 400 may be provided on only one glasses leg 8.

Although the sensor module 460 of any of the apparatuses 400, 401, and 402 is supported by the connection frame 450 in any of FIGS. 40 through 45, the inventive concept is not limited thereto. For example, the sensor module 460 may be provided on a surface, that is, an inner surface, of the main body that contacts the head 1 when the main body of the apparatus is attached to the glasses leg 8 and is worn on the head 1. In this case, the sensor module 460 may be supported by the sensor support 120 (see FIG. 3) such as a spiral spring.

Figure 46:
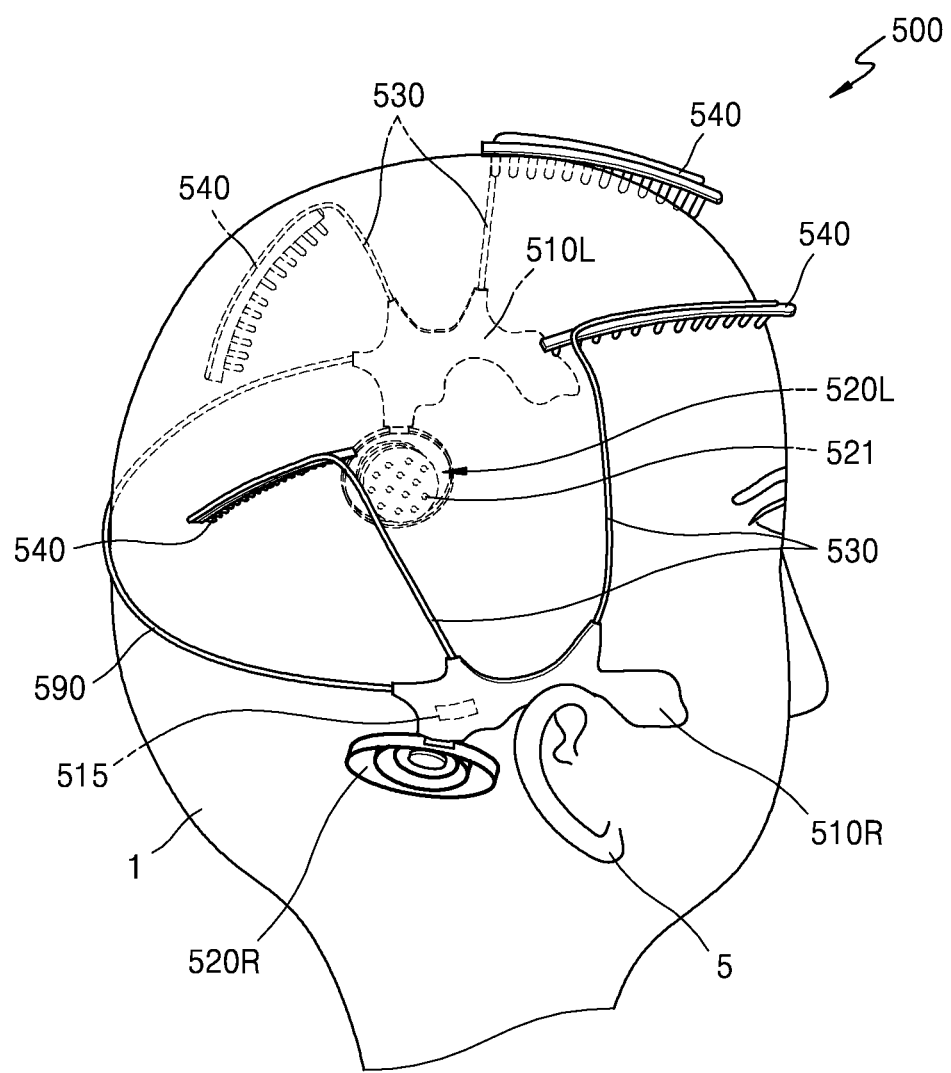
FIG. 46 is a view of an apparatus for measuring bioelectrical signals, according to another exemplary embodiment.

FIG. 46 is a view of an apparatus 500 for measuring bioelectrical signals according to another exemplary embodiment.

The apparatus 500 includes a frame that is mounted on the head 1 and a sensor module 540 that is provided on the frame and measures bioelectrical signals. The frame includes left and right main frames 510L and 510R that are provided on both sides of the head 1 of the living body, a connection frame 530 that supports the sensor module 540 and is connected to the left and right main frames 510L and 510R, and a fixing frame 590 that connects the left and right main frames 510L and 510R.

The left and right main frames 510L and 510R may each be formed of a plastic mold, and may fix the connection frame 530 and the fixing frame 590. The left and right main frames 510L and 510R may be provided over the ears 5 when being worn, and may be customized to conform to the head 1 of the living body who wears the apparatus 500.

The connection frame 530 and the fixing frame 590 may be integrally formed with the left and right main frames 510L and 510R. Alternatively, at least one slot (not shown) may be formed in each of the left and right main frames 510L and 510R, and the connection frame 530 and/or the fixing frame 590 may be detachably inserted into the at least one slot.

The connection frame 530 may have a curved bar shape that longitudinally extends to closely contact the scalp of the living body about the ear 5 of the living body. The connection frame 530 may be formed of an elastic material to elastically press the sensor module 540 to the scalp. The sensor module 540 may be provided on one end of the connection frame 530. The sensor module 540 may have, for example, a structure of any of FIGS. 29 through 34. The sensor module 540 may include the sensor electrodes of any of FIGS. 5, 17A through 17D, and 18 through 20. Alternatively, the sensor module 540 may use well-known sensor electrodes. The sensor circuit 160 (see FIG. 10) for amplifying bioelectrical signals detected by the sensor electrodes or converting bioelectrical signals into digital signals may be provided in the sensor module 540.

A reference electrode 520L may be coupled to the left main frame 510L to be located behind the left ear of the head 1 when the apparatus 500 is worn on the head 1. A ground electrode 520R may be coupled to the right main frame 510R to be located behind the right ear of the living body when the apparatus 500 is worn on the living body.

Figure 47:
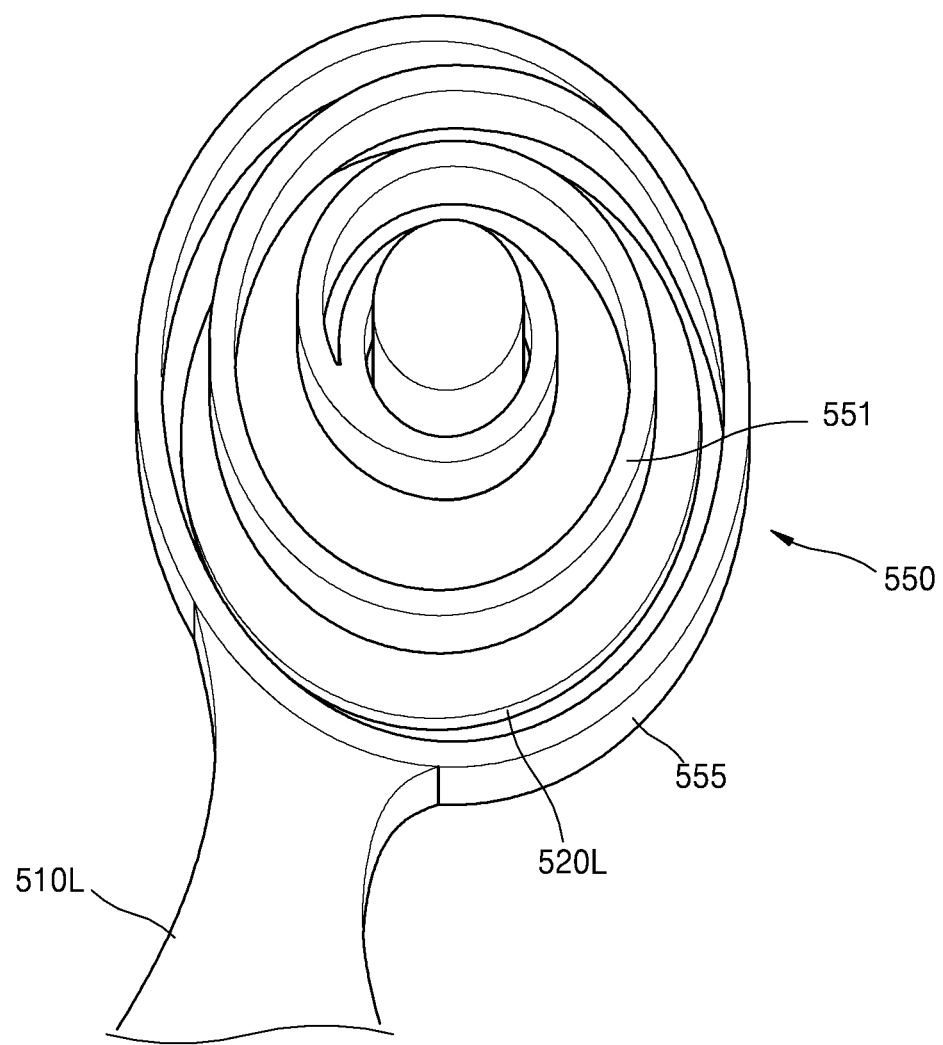
FIG. 47 is a view of a reference electrode attached to the apparatus of FIG. 46 and a sensor support that supports the reference electrode.

FIG. 47 is a view of the reference electrode 520L that is attached to the apparatus 500 and a sensor support 550 that supports the reference electrode 520L. Referring to FIG. 47, the sensor support 550 that elastically supports the reference electrode 520L so that the reference electrode 520L moves in 3-axis directions with respect to the left main frame 510L may be provided between the left main frame 510L and the reference electrode 520L. The sensor support 550 may include a spiral spring 551 and a support edge 555. The reference electrode 520L is attached to one inner end of the spiral spring 551 and the other outer end of the spiral spring 551 is fixed to the support edge 555. The support edge 555 is fixed to a portion of the left main frame 510L that is behind the ear, to allow the reference electrode 520L to contact a portion behind the ear. The spiral spring 551 and the edge support 555 may be integrally formed by using a plastic material. Also, a cable including a wiring for receiving a reference signal and a power wiring for supplying power to the reference electrode 520L may be buried in the spiral spring 551 and the support edge 555. The support edge 555 may be omitted, and the spiral spring 551 may be directly fixed to the left main frame 510L. The ground electrode 520R may also be supported by a sensor support that elastically supports the ground electrode 520R so that the ground electrode 520R moves in 3-axis directions.

Positions of the reference electrode 520L and the ground electrode 520R may be exchanged so that the reference electrode may be coupled to the right main frame 510R and the ground electrode may be coupled to the left main frame 510L.

A main circuit 515 (see FIG. 46) may be provided in at least one of the left main frame 510L and the right main frame 510R. For example, as shown in FIG. 46, the main circuit 515 may be embedded in the right main frame 510R and only a simple wiring may be provided in the left main frame 510L. In this case, the right main frame 510R may be understood as a main body and the left main frame 510L may be understood as a dummy frame. Alternatively, the left main frame 510L may function as a main body and the main circuit 515 may be embedded in the left main frame 510L. Alternatively, a part of the main circuit 515 may be provided in the left main frame 510L and another part of the main circuit 515 may be provided in the right main frame 510R, or the main circuit 515 may be provided in each of the left and right main frames 510L and 510R. In this case, both the left and right main frames 510L and 510R may be understood as main bodies.

The main circuit 515 may process bioelectrical signals obtained by the sensor module 540, the reference electrode 520L, and the ground electrode 520R and may communicate with the outside as described with reference to FIG. 16.

Figure 48:
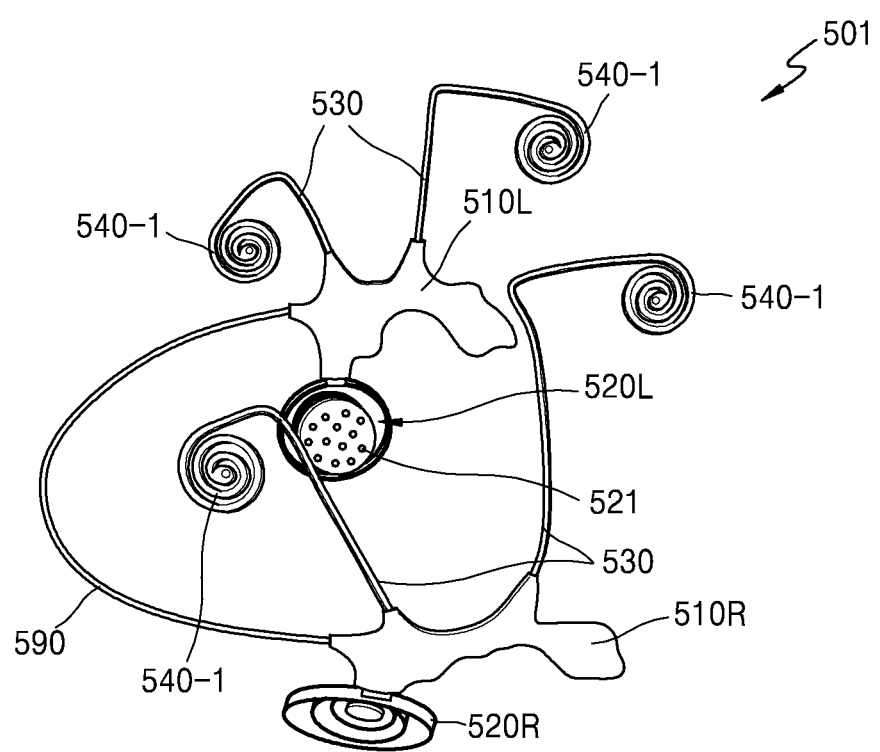
FIG. 48 is a view of an apparatus for measuring bioelectrical signals, according to another exemplary embodiment.

FIG. 48 is a view of an apparatus 501 for measuring bioelectrical signals according to another exemplary embodiment. Referring to FIG. 48, the apparatus 501 of the present exemplary embodiment is substantially the same as the apparatus 500 of FIGS. 46 and 47 except a sensor module 540-1. The sensor module 540-1 may be provided on one end of the connection frame 530, and may have, for example, a structure of FIGS. 3 and 4. That is, a sensor support that has a spiral spring shape and elastically supports the sensor module 540-1 may be provided between the connection frame 530 and the sensor module 540-1. The sensor support may be integrally formed with the connection frame 530.

Figure 49:
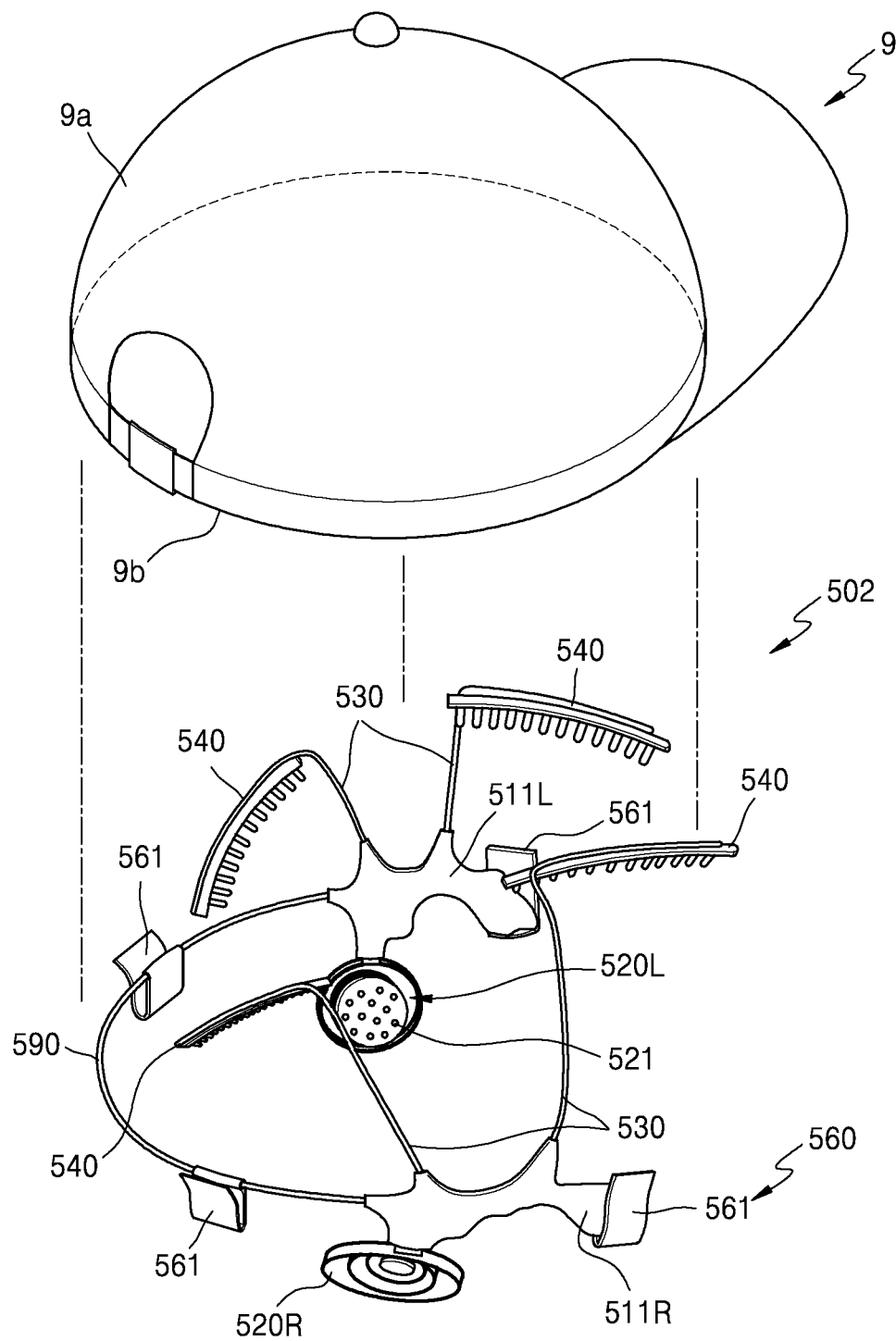
FIG. 49 is a view of an apparatus for measuring bioelectrical signals, according to another exemplary embodiment.

FIG. 49 is a view of an apparatus 502 for measuring bioelectrical signals according to another exemplary embodiment. Referring to FIG. 49, the apparatus 502 includes an attachment/detachment coupler 560 that is attached to a cap 9. The apparatus 502 of the present exemplary embodiment is substantially the same as the apparatus 500 of FIGS. 46 and 47 except the attachment/detachment coupler 560. The attachment/detachment coupler 560 may include left and right main frames 511L and 511R and/or a clip 561 provided on the fixing frame 590. The clip 561 may fit around an edge 9b of a cap portion 9a of the cap 9 when the apparatus 501 is inserted into the cap portion 9a of the cap 9. The apparatus 501 may be attached to the cap 9 and may be used daily while being worn. Since the apparatus 502 of the present exemplary embodiment is fixed to the head 1 by using the cap 9, the apparatus 502 may be less affected by an external condition. For example, the apparatus 502 may stably measure brain waves even while the person sleeps.

Although the attachment/detachment coupler 560 has a clip structure in FIG. 49, the inventive concept is not limited thereto. For example, the attachment/detachment coupler 560 may use a well-known structure such as an insertion structure or a Velcro structure.

Figure 50:
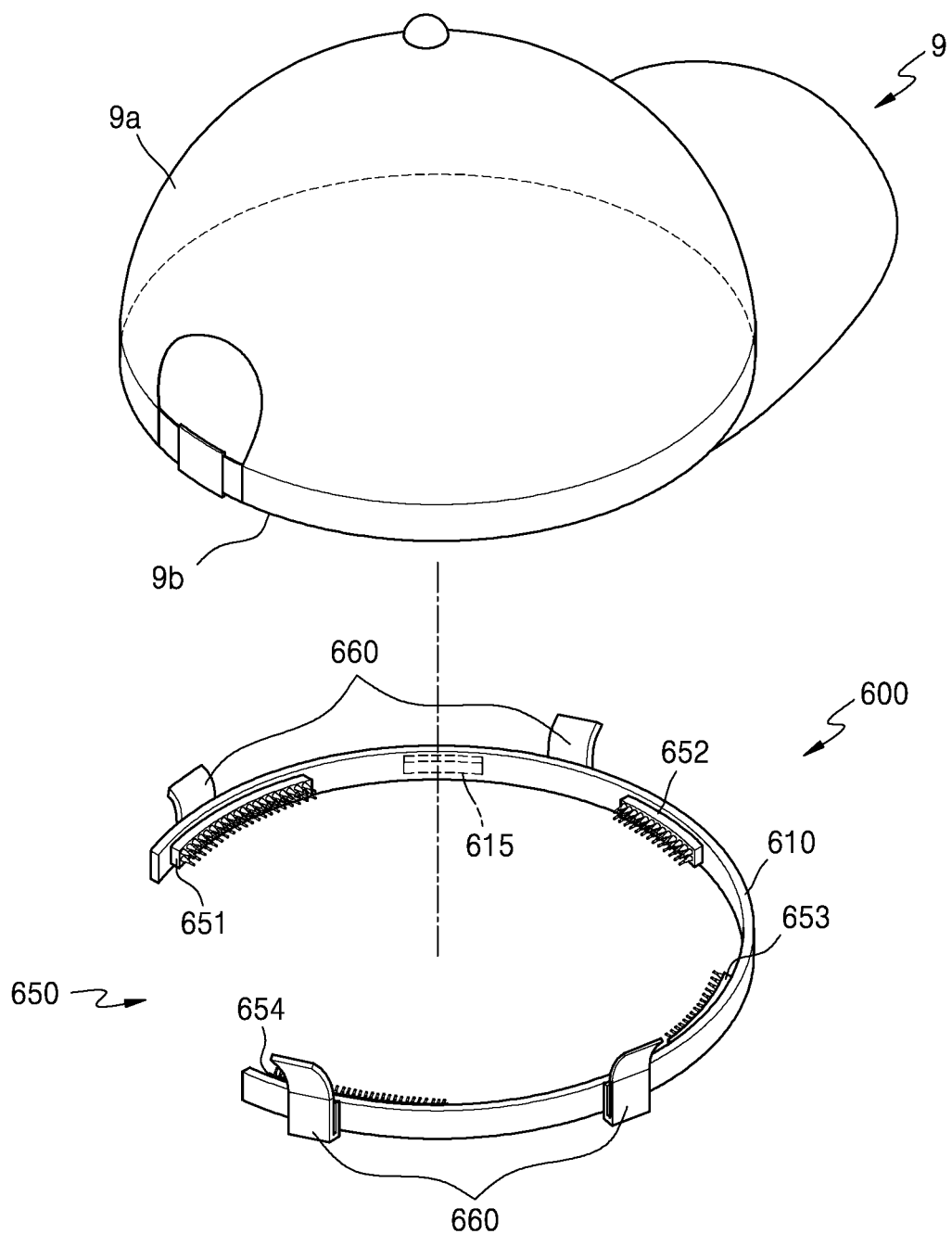
FIG. 50 is a view of an apparatus for measuring bioelectrical signals, according to another exemplary embodiment.

FIG. 50 is a view of an apparatus 600 for measuring bioelectrical signals according to another exemplary embodiment. Referring to FIG. 50, the apparatus 600 that is attached to the cap 9, and includes a main body 610 having an edge shape, a sensor module 650 disposed on an inner surface of the main body 610, and an attachment/detachment coupler 660. The main body 610 may be formed of an elastic plastic mold. The sensor module 650 may include a plurality of sensor electrodes 651, 652, 653, and 654 having different measurement positions. Some of the plurality of sensor electrodes 651, 652, 653, and 654 may function as reference electrodes and/or ground electrodes, and the remaining sensor electrodes may function as sensor electrodes for measuring brain waves. The sensor module 650 may include the sensor electrodes of any of FIGS. 5, 17A through 17D, and 18 through 20. Alternatively, the sensor module 650 may include well-known sensor electrodes. The sensor module 650 may be supported by the sensor support 120 (see FIG. 3) having a spiral spring shape.

A main circuit 615 may be embedded in the main body 610. The main circuit 615 may process bioelectrical signals obtained by the sensor module 650 and may communicate with the outside as described with reference to FIG. 16. The attachment/detachment coupler 660 may be provided on the main body 610, may have, for example, a clip structure, and may be coupled to the edge 9b of the cap portion 9a of the cap 9 when the apparatus 600 is inserted into the cap portion 9a of the cap 9. Although the attachment/detachment coupler 660 has a clip structure in FIG. 50, the inventive concept is not limited thereto. For example, the attachment/detachment coupler 660 may have a well-known structure such as an insertion structure or a Velcro structure.

Since the apparatus 600 of the present exemplary embodiment is fixed to the head 1 by using the cap 9, the apparatus 600 may be less affected by an external condition. For example, the apparatus 600 of the present exemplary embodiment may stably measure brain waves even while the person sleeps.

Figure 51:
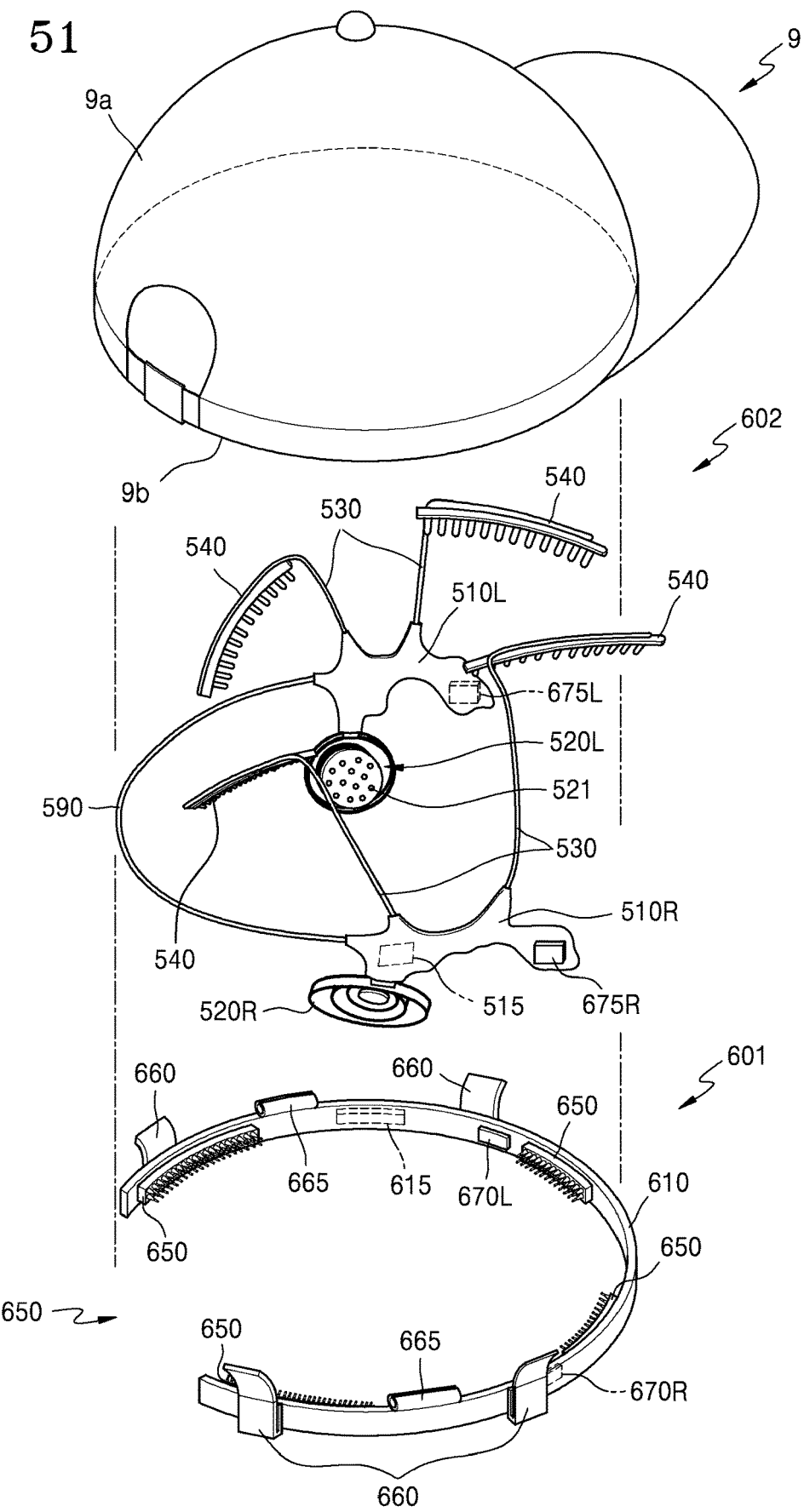
FIG. 51 is a view of an apparatus for measuring bioelectrical signals, according to another exemplary embodiment.

FIG. 51 is a view of an apparatus for measuring bioelectrical signals according to another exemplary embodiment.

Referring to FIG. 51, the apparatus of the present exemplary embodiment includes a first apparatus 601 for measuring bioelectrical signals that has an edge shape and is attached to the cap 9 and a second apparatus 602 for measuring bioelectrical signals that is detachably coupled to the first apparatus 601. The first apparatus 601 includes the main body 610 having an edge shape and to be attached to an inner surface of the cap 9, the sensor module 650 disposed on an inner surface of the main body 610, and the attachment/detachment coupler 660 attached/detached to/from the cap 9. Also, the second apparatus 602 includes the left and right main frames 510L and 510R located on both sides of the head 1, the connection frame 530 connected to the left and right main frames 510L and 510R, the sensor module 540 located on one end of the connection frame 530, and the fixing frame 590 configured to connect the left and right main frames 510L and 510R. Coupling portions 670L, 670R, 675L, and 675R are provided on the main body 610 of the first apparatus 601 and the left and right main frames 510L and 510R of the second apparatus 602. Each of the coupling portions 670L, 670R, 675L, and 675R may have a detachable structure such as a permanent magnet or a Velcro. Furthermore, a connection unit (not shown) for electrically connecting the first apparatus 601 and the second apparatus 602 may be provided on the coupling portions 670L, 670R, 675L, and 675R. The first apparatus 601 and the second apparatus 602 may be substantially the same as the apparatus 500 of FIG. 46 and the apparatus 600 of FIG. 50 except the coupling portions 670L, 670R, 675L, and 675R.

Figure 52:
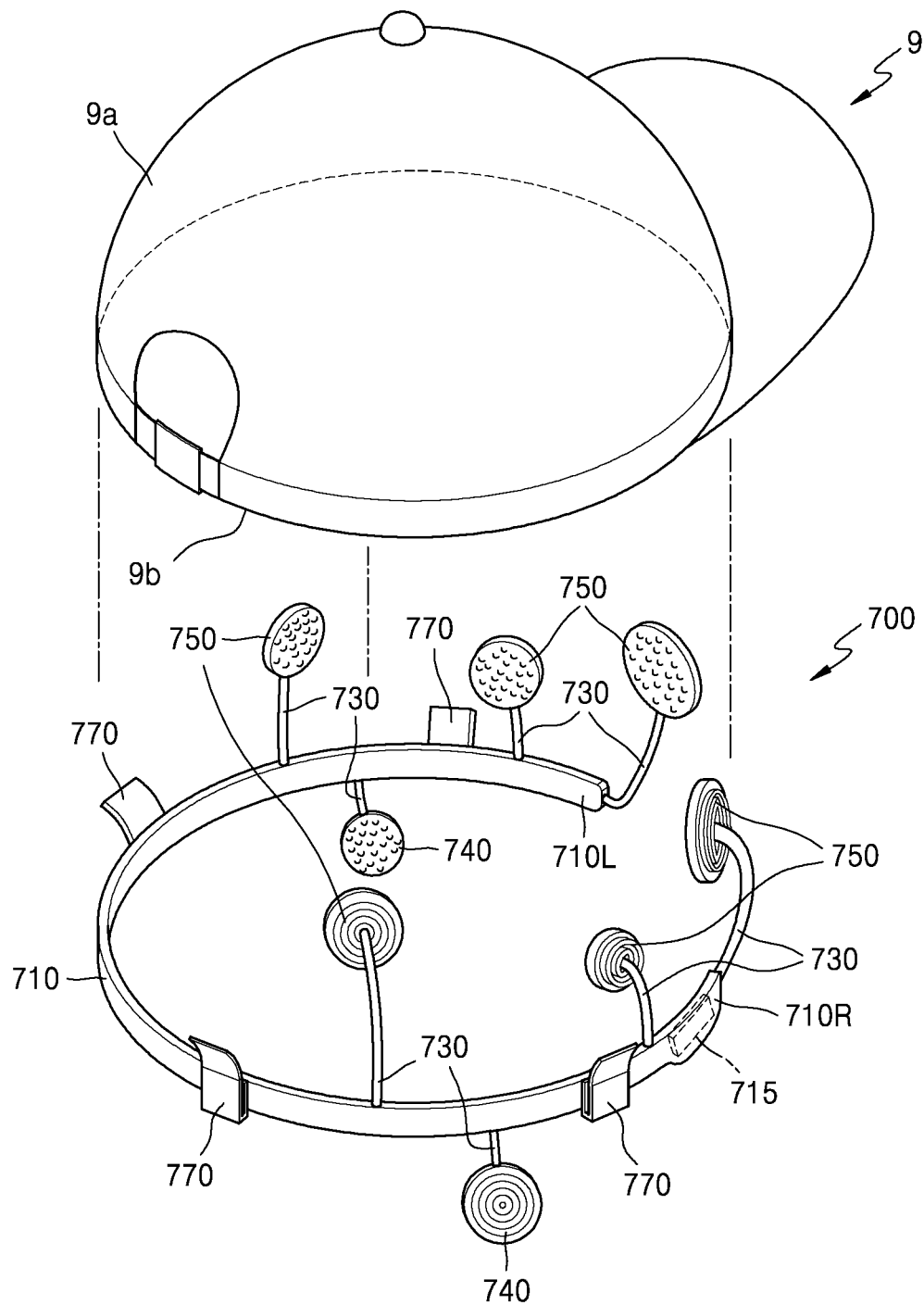
FIG. 52 is a view of an apparatus for measuring bioelectrical signals, according to another exemplary embodiment.

FIG. 52 is a view of an apparatus 700 for measuring bioelectrical signals according to another exemplary embodiment. Referring to FIG. 52, the apparatus 700 of the present exemplary embodiment includes a main body 710 having an edge shape and attached to the cap 9, a connection frame 730 extending from the main body 710, and a sensor module 750 disposed on one end of the connection frame 730. The connection frame 730 may be formed of an elastic material to elastically press the sensor module 750 to the scalp. The sensor module 750 may be provided on the one end of the connection frame 730 and may have, for example, a structure of FIGS. 3 and 4. That is, a sensor support having a spiral spring shape and elastically supporting the sensor module 750 in 3-axis directions may be provided between the sensor module 750 and the connection frame 730. The sensor support may be integrally formed with the connection frame 730. Alternatively, as shown in FIG. 53, the sensor module 750 may be directly supported by the connection frame 730 without the sensor support having a spiral spring shape.

A main circuit 715 may be embedded in the main body 710. An attachment/detachment coupler 770 may be provided on the main body 710, may have, for example, a clip structure, and may be coupled to the edge 9b of the cap portion 9a of the cap 9 when the apparatus 700 is inserted into the cap portion 9a of the cap 9. Since the apparatus 700 of the present exemplary embodiment is fixed to the head 1 by using the cap 9, the apparatus 700 may be less affected by an external condition. For example, the apparatus 700 of the present exemplary embodiment may stably measure brain waves even while the person sleeps.

Figure 53:
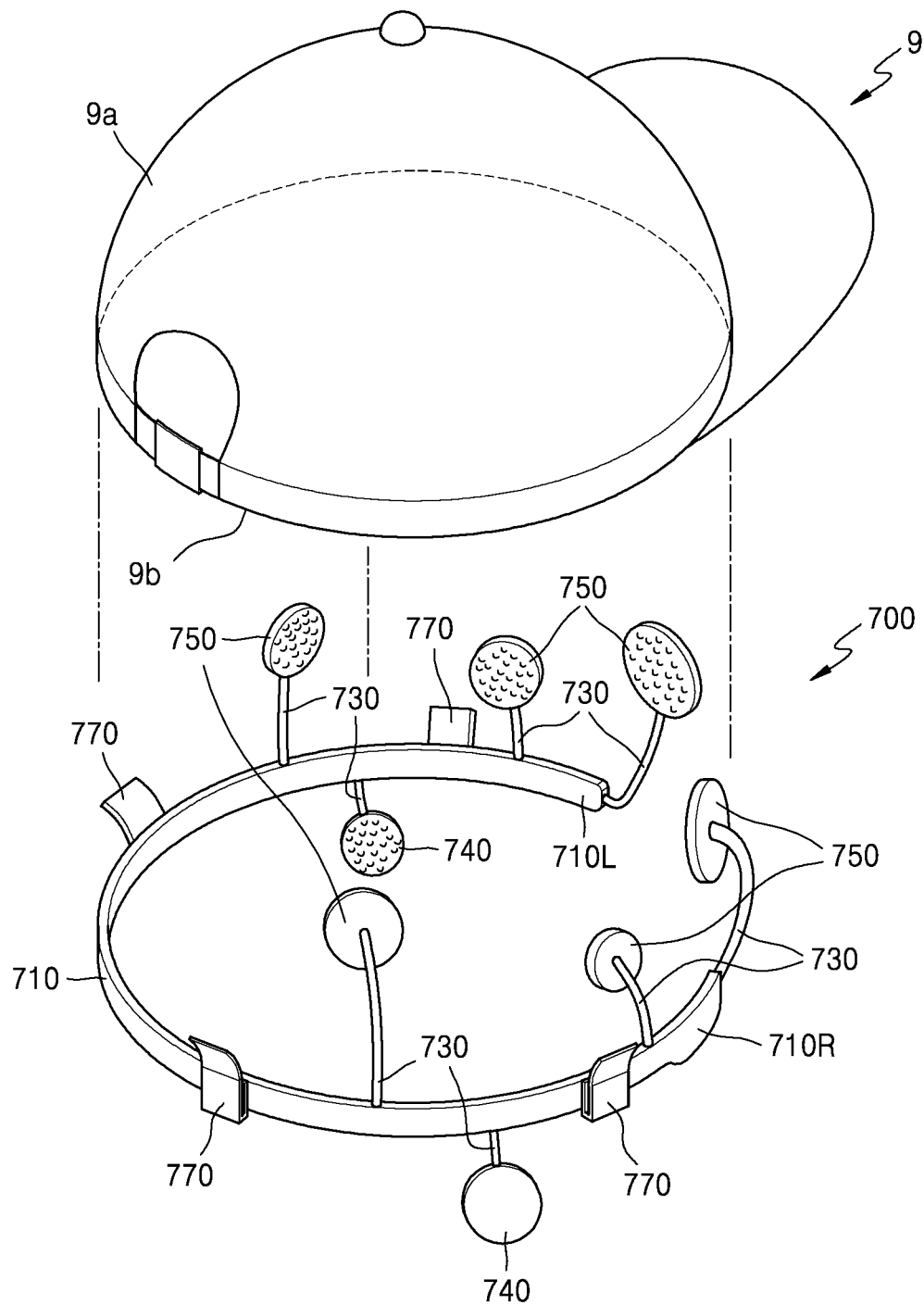
FIG. 53 is a view of an apparatus for measuring bioelectrical signals, according to another exemplary embodiment.

Although the attachment/detachment coupler 770 has a clip structure in FIGS. 52 and 53, the inventive concept is not limited thereto. For example, the attachment/detachment coupler 770 may have a well-known structure such as an insertion structure or a Velcro structure.

Figure 54A:
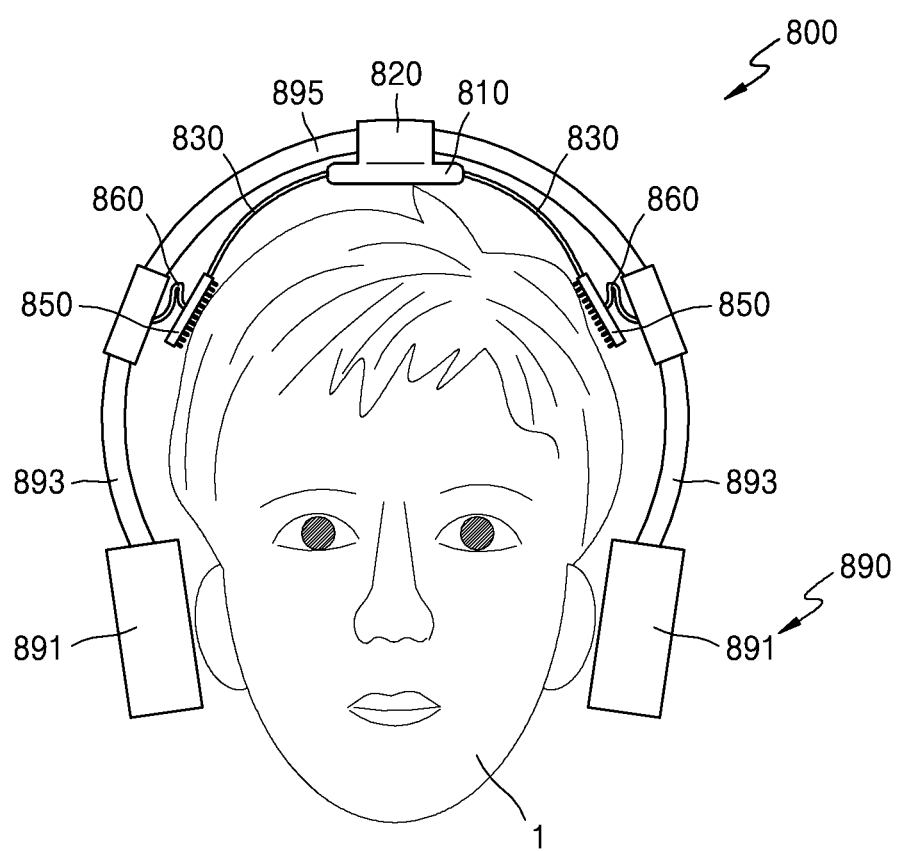
FIG. 54A is a view of an apparatus for measuring bioelectrical signals, according to another exemplary embodiment.

FIG. 54A is a view of an apparatus 800 for measuring bioelectrical signals according to another exemplary embodiment.

Referring to FIG. 54A, the apparatus 800 of the present exemplary embodiment is attached to a headphone 890 and measures brain waves of a person. The headphone 890 has a structure in which one pair of driver housings 891 on which drivers for outputting sounds are provided are connected to each other by a headband 895. Reference numeral 893 denotes a slider for adjusting a length of the headband 895. When the headphone 890 is worn, the headband 895 and the top of the head 1 may be spaced apart by an interval from each other. The interval may be predetermined. A shape of the headphone 890 is exemplary and the inventive concept is not limited thereto. The apparatus 800 includes a main body 810 disposed between the head 1 and the headband 895 when the headphone 890 is worn, an attachment/detachment coupler 820 configured to attach/detach the main body 810 to/from a lower end of the headband 895, one pair of connection frames 830 extending from the main body 610 to both sides of the head 1, and one pair of sensor modules 850 respectively attached to the one pair of connection frames 830.

A main circuit (not shown) may be embedded in the main body 810. The main circuit may alternatively be provided in one of the driver housings 891. The main circuit may process bioelectrical signals obtained by the sensor module 850 and may communicate with the outside as described with reference to FIG. 16.

The connection frame 830 may be formed of an elastic material to elastically press the sensor module 850 to the scalp. The connection frame 830 may be integrally coupled to the main body 610 or may be detachably coupled to the main body 610. The attachment/detachment coupler 820 may have, for example, a clip structure provided on an upper end of the main body 810 and may fit around the headband 895. Alternatively, the attachment/detachment coupler 820 may have a well-known structure such as a Velcro structure or a button structure.

The sensor module 850 may include the sensor electrodes of any of FIGS. 5, 17a through 17D, and 18 through 20. Alternatively, the sensor module 850 may include well-known sensor electrodes. Furthermore, the sensor module 850 may have, for example, a structure of FIGS. 3 and 4. Alternatively, the sensor module 850 may have, for example, a structure of any of FIGS. 29 through 34. The sensor support 120 (see FIG. 3) having a spiral spring shape and elastically supporting the sensor module 850 in 3-axis directions may be provided between the sensor module 850 and the connection frame 830.

Figure 54B:
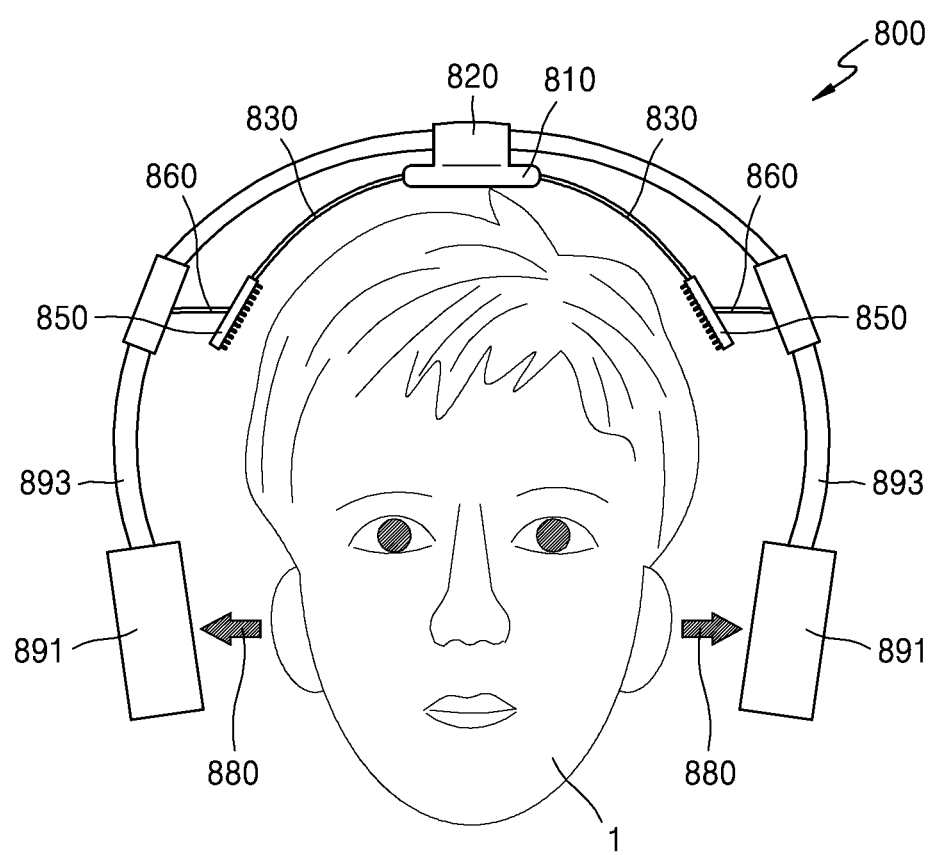
FIG. 54B is a view illustrating a case where the apparatus of FIG. 54A is worn or is taken off.

The one pair of sensor modules 850 located on the left and right of the head 1, respectively, when worn on the head 1 may be connected by using strings 860 to the left and right of the headphone 890. FIG. 54B is a view illustrating a case when the apparatus 800 of the present exemplary embodiment is worn or taken off. As shown in FIG. 54B, a user increases an interval between the driver housings 891 in order to wear or take off the headphone 890. Since the strings 860 may allow an interval between the sensor modules 850 to be increased as the interval between the driver housings 891 is increased, the apparatus 800 may be easily worn when the headphone 890 is worn. The string 860 connected to each sensor module 850 may be a cable for electrical connection with the main circuit in the sensor module 850 and the main body 810. Alternatively, a cable may be additionally provided in consideration of mechanical durability. Alternatively, a cable may be buried in the connection frame 830

Although the sensor modules 850 are respectively provided at the left and right of the main body 810 in the present exemplary embodiment, the sensor module 850 may be provided only at one side of the main body 810 or two or more sensor modules 850 may be respectively provided at the left and right of the main body 810. For example, three or more connection frames 830 may extend from the main body 810.

Figure 55:
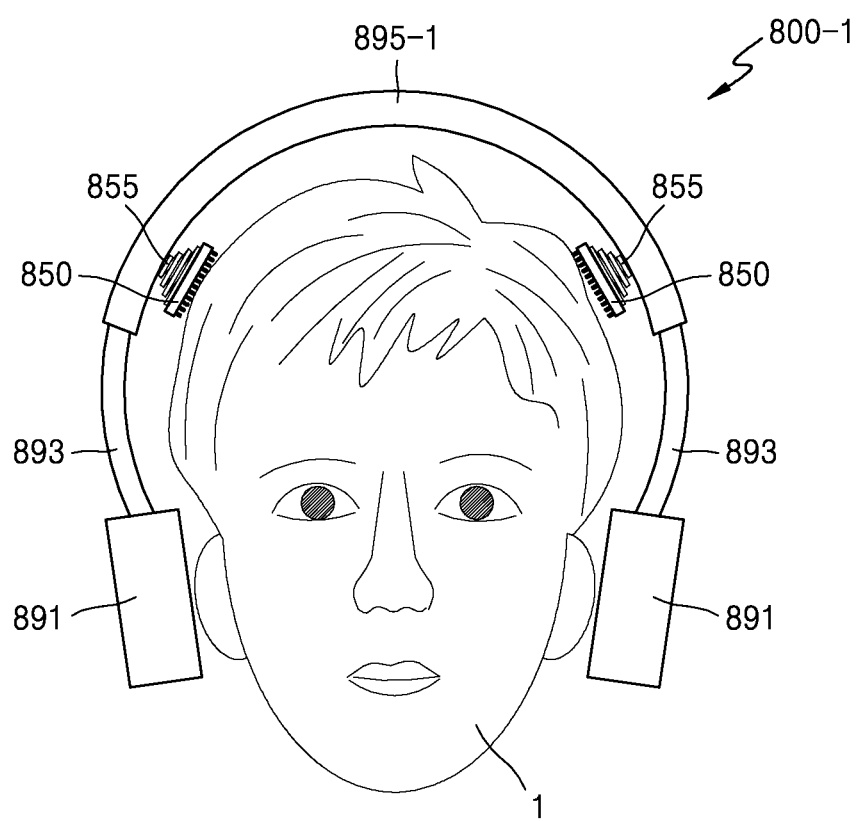
FIG. 55 is a view of an apparatus for measuring bioelectrical signals, according to another exemplary embodiment.

FIG. 55 is a view of an apparatus 800-1 for measuring bioelectrical signals according to another exemplary embodiment. Referring to FIG. 55, the apparatus 800-1 of the present exemplary embodiment has a headphone shape and includes one pair of driver housings 891 and a headband 895-1 that connects the one pair of driver housings 891. The headphone shape is exemplary and the inventive concept is not limited thereto. The sensor module 850 is provided on a bottom surface of the headband 895-1 and measures brain waves of a person. At least a part of the headband 895-1 may be formed of a hard material such as plastic and may support the sensor module 850. One pair of sensor modules 850 may be disposed to measure, for example, points over both ears. Alternatively, one sensor module 850 or three or more sensor modules 850 may be disposed on the bottom surface of the headband 895-1. A sensor support 855 including the spiral spring 121 (see FIG. 3) that elastically supports the sensor module 850 in 3-axis directions may be provided between the sensor module 850 and the headband 895-1. A main circuit (not shown) may be provided in the main body 810. The main circuit may be provided in the headband 895-1 or each of the driver housings 891.

Figure 56:
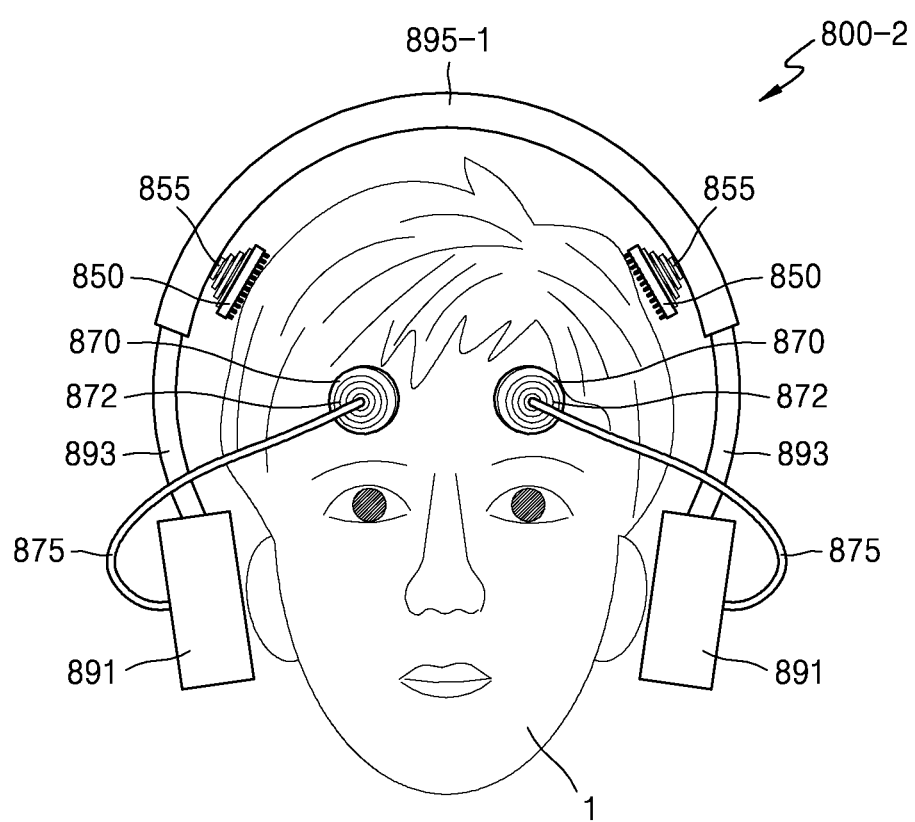
FIG. 56 is a view of an apparatus for measuring bioelectrical signals, according to another exemplary embodiment.

FIG. 56 is a view of an apparatus 800-2 for measuring bioelectrical signals according to another exemplary embodiment. The apparatus 800-2 of the present exemplary embodiment includes one pair of driver housings 891, the headband 895-1 that connects the one pair of driver housings 891, the sensor modules 850 (referred to as first sensor modules 850) that are disposed on a bottom surface of the headband 895-1, and second sensor modules 870 that extend from the one pair of driver housings 891. The apparatus 800-2 may be obtained by adding the second sensor modules 870 to the apparatus 800-1 of FIG. 55. The second sensor modules 870 are supported by connection frames 875 that extend from the driver housings 891 to the forehead of the person. The second sensor modules 870 are attached to the forehead and detect bioelectrical signals. Sensor supports 872 including the spiral springs 121 (see FIG. 3) that elastically support the second sensor modules 870 in 3-axis directions may be provided between the second sensor modules 870 and the connection frames 875. The connection frames 875 may be detachably coupled to the driver housings 891 or may be integrally formed with the driver housings 891. The connection frame 875 may be bent to adjust positions, or may be rotatably coupled to the driver housings 891. Although one pair of second sensor modules 870 and one pair of connection frames 875 are provided in the present exemplary embodiment, the sensor module 870 and the connection frame 875 may be provided on only one of the driver housings 891.

Figure 57:
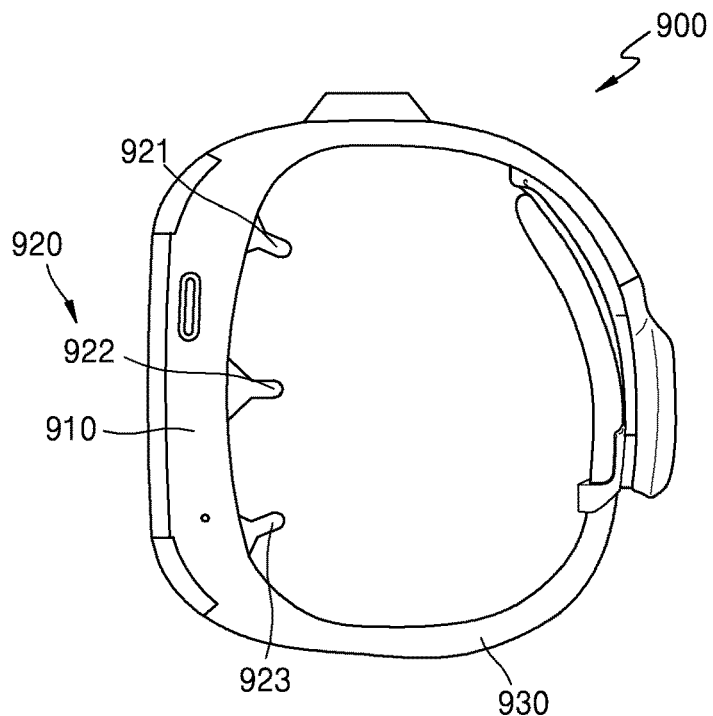
FIG. 57 is a view of an apparatus for measuring bioelectrical signals, according to another exemplary embodiment.

FIG. 57 is a view of an apparatus 900 for measuring bioelectrical signals according to another exemplary embodiment. The apparatus 900 of the present exemplary embodiment includes a main body 910 and a band 930 that supports the main body 910 and is worn on a wrist. The main body 910 and the band 930 may be understood as a wristwatch or a wristband. The main circuit 140 (see FIG. 16) may be embedded in the main body 910. A sensor module 920 is provided on an inner surface, that is, a surface of the main body 910 that contacts the wrist. The sensor module 920 may include at least one sensor electrode 921 for measuring bioelectrical signals, a reference electrode 922, and a ground electrode 923. According to a method of processing bioelectrical signals, one or both of the reference electrode 922 and the ground electrode 923 may be omitted. The sensor module 920 may measure, for example, EMG signals in the wrist. The sensor electrode 921, and the reference electrode 922, and the ground electrode 923 may be the electrodes of any of FIGS. 5, 17A through 17D, and 18 through 20. Sizes of the sensor electrode 921, and the reference electrode 922, and the ground electrode 923 of FIG. 57 are exaggerated for clarity, and a plurality of the sensor electrodes 921, and the reference electrodes 922, and the ground electrodes 923 having small sizes may be provided. A concave space may be formed in the inner surface of the main body 910 and a sensor support (not shown) for elastically supporting the sensor module 920 may be located in the concave space. For example, the sensor support may have a spiral spring shape similar to that of the spiral spring of FIG. 11 or 25, and one end of the spiral spring shape may be coupled to the main body 910 and the other end of the spiral spring shape may be coupled to the sensor module 920.

Although the sensor module 920 of the apparatus 900 is provided on the inner surface of the main body 910, the inventive concept is not limited thereto. Various modifications of the apparatus 900 will now be explained with reference to FIGS. 58A through 58F.

Figure 58A:
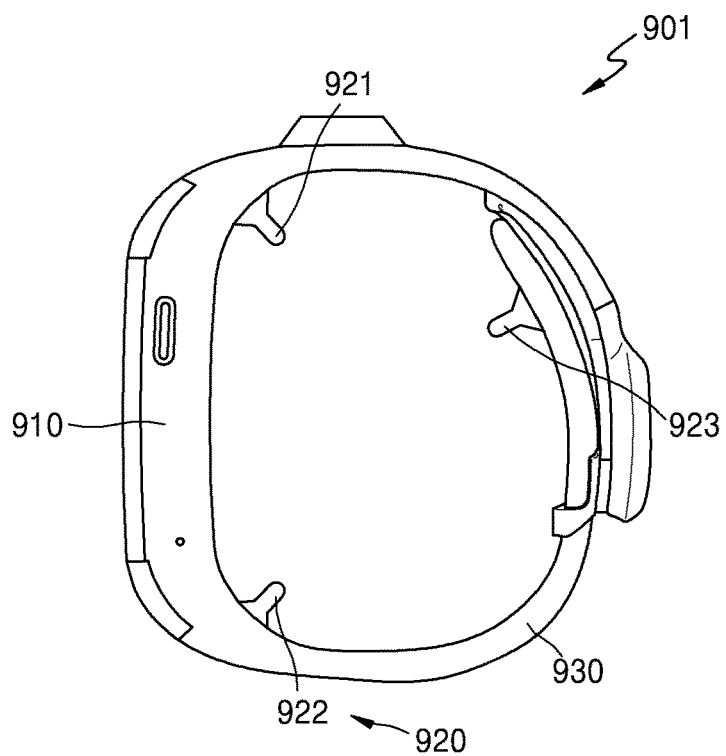
FIGS. 58A through 58F are views of various modifications of the apparatus of FIG. 57.

For example, as shown in FIG. 58A, in an apparatus 901 for measuring bioelectrical signals, the sensor electrode 921, and the reference electrode 922, and the ground electrode 923 may be provided on an inner surface of a wristband that contacts a wrist.

Figure 58B:
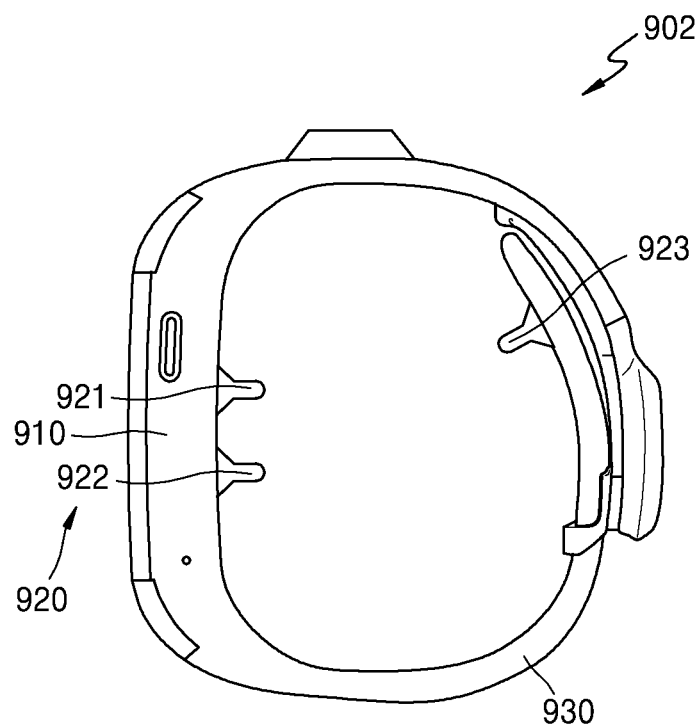

Alternatively, as shown in FIG. 58B, in an apparatus 902 for measuring bioelectrical signals, the sensor electrode 921 and the reference electrode 922 may be provided on an inner surface of the main body 910 and the ground electrode 923 may be provided on an inner surface of a wristband.

Figure 58C:
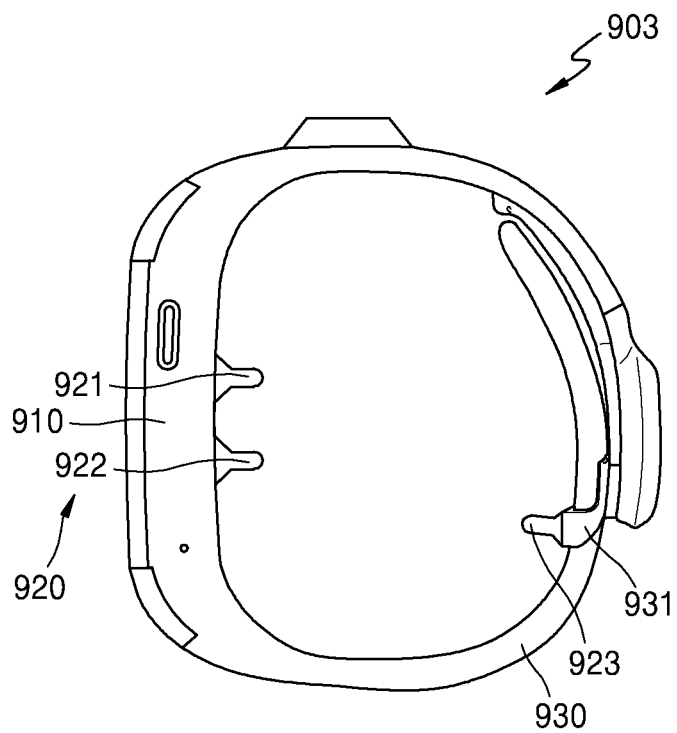

Alternatively, as shown in FIG. 58C, in an apparatus 903 for measuring bioelectrical signals, the sensor electrode 921 and the reference electrode 922 may be provided on an inner surface of the main body 910 and the ground electrode 923 may be provided on a buckle 931 of a wristband 930.

Figure 58D:
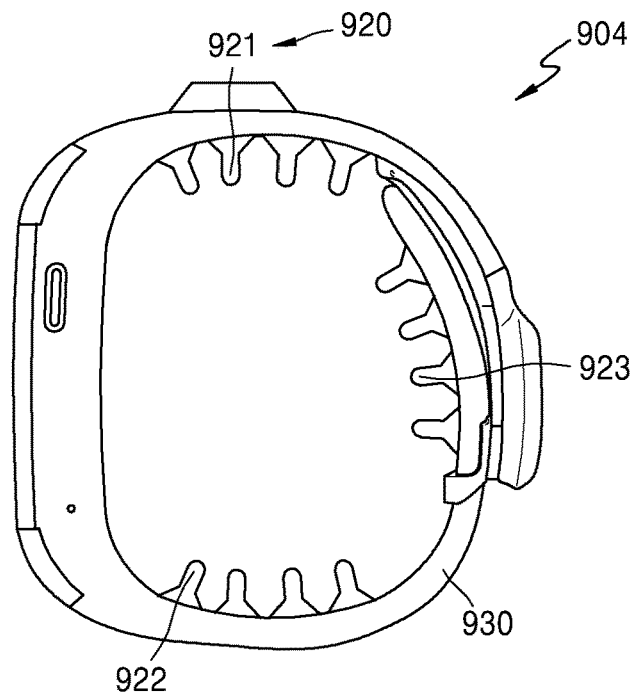

Alternatively, as shown in FIG. 58D, in an apparatus 904 for measuring bioelectrical signals, a plurality of the sensor electrodes 921 for measuring bioelectrical signals, the reference electrodes 922, and the ground electrodes 923 may be grouped and may be provided on an inner surface of a wristband that contacts a wrist.

Figure 58E:
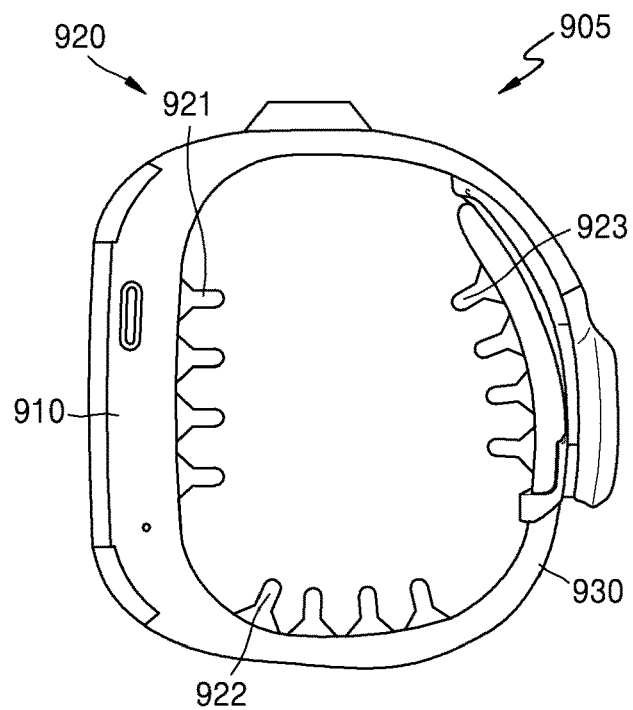

Alternatively, as shown in FIG. 58E, in an apparatus 905 for measuring bioelectrical signals, a plurality of the sensor electrodes 921 for measuring bioelectrical signals may be provided on an inner surface of the main body 910 and a plurality of the reference electrodes 922 and the ground electrodes 923 may be grouped and may be provided on an inner surface of a wristband that contacts a wrist.

Figure 58F:
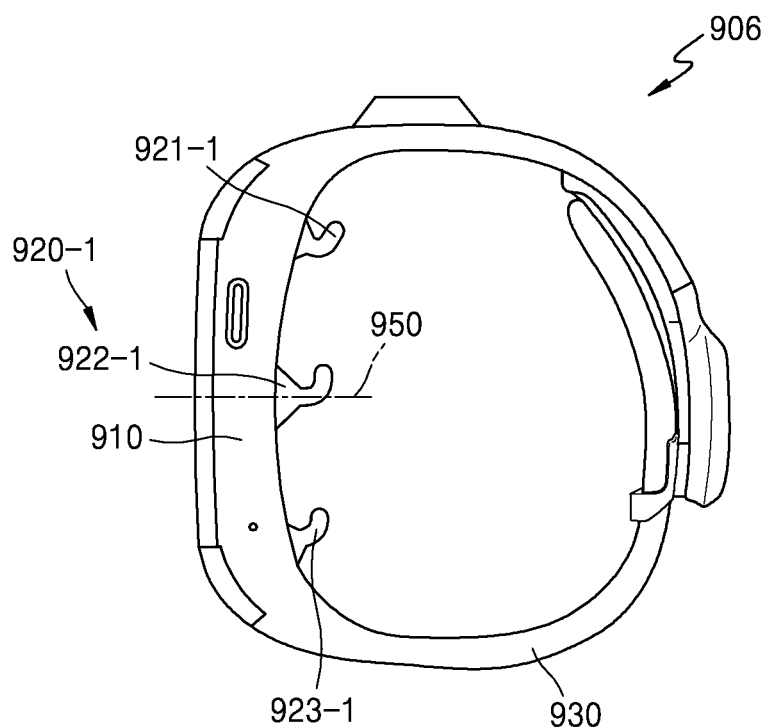

Alternatively, as shown in FIG. 58F, in an apparatus 906 for measuring bioelectrical signals, a sensor module 920-1 may be formed so that protruding portions are bent or inclined with respect to a direction 950 that is perpendicular to a surface on which sensor electrodes 921-1, 922-1, and 923-1 are attached. Since the protruding portions of the sensor electrodes 921-1, 922-1, and 923-1 are bent or inclined, a pressure applied to a user may be further reduced and a measurement area may be increased as discussed above.

Although the sensor electrodes include the tapering portions in any of FIGS. 57 and 58A through 58F, the inventive concept is not limited thereto. The sensor modules 920 or 920-1 may include sensor electrodes including only protruding portions (for example, 2010b of FIG. 65) having prism shapes, without tapering portions. In this case, when the sensor electrodes contact a wrist portion, the protruding portions are bent by a pressing force, and side portions, that is, outer circumferential surfaces, of the protruding portions contact the wrist portion, to measure EMG signals.

Figure 59:
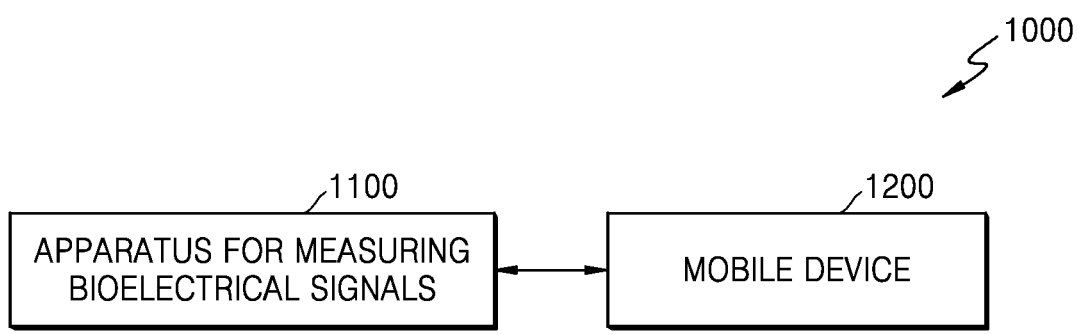
FIG. 59 is a view of a system for processing bioelectrical signals, according to another exemplary embodiment.
Figure 60:
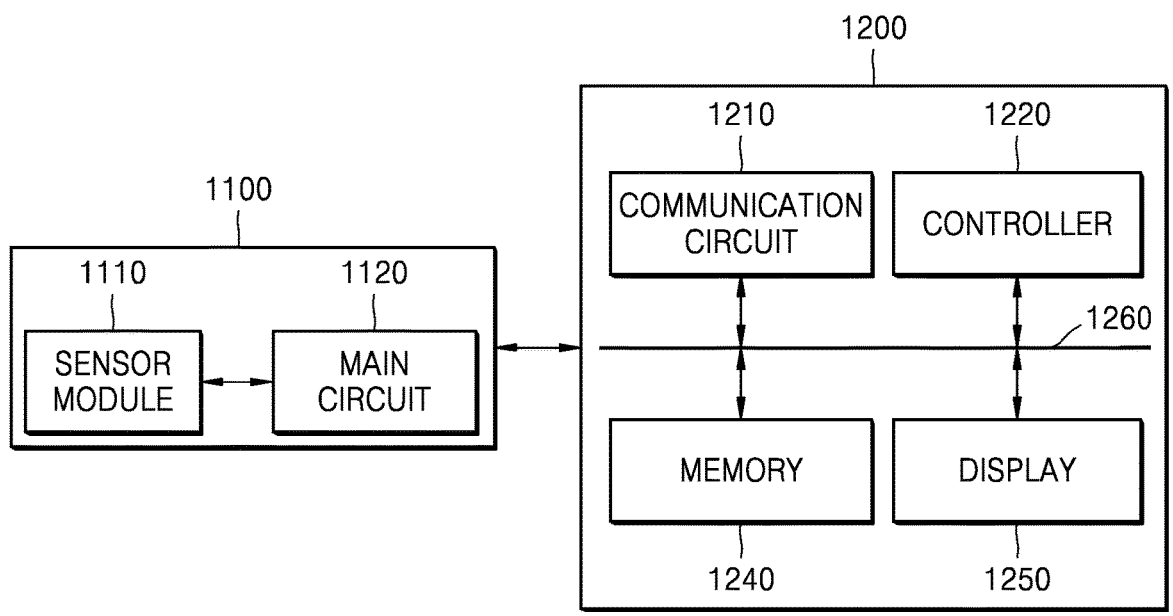
FIG. 60 is a block diagram of the system of FIG. 59.
Figure 61:
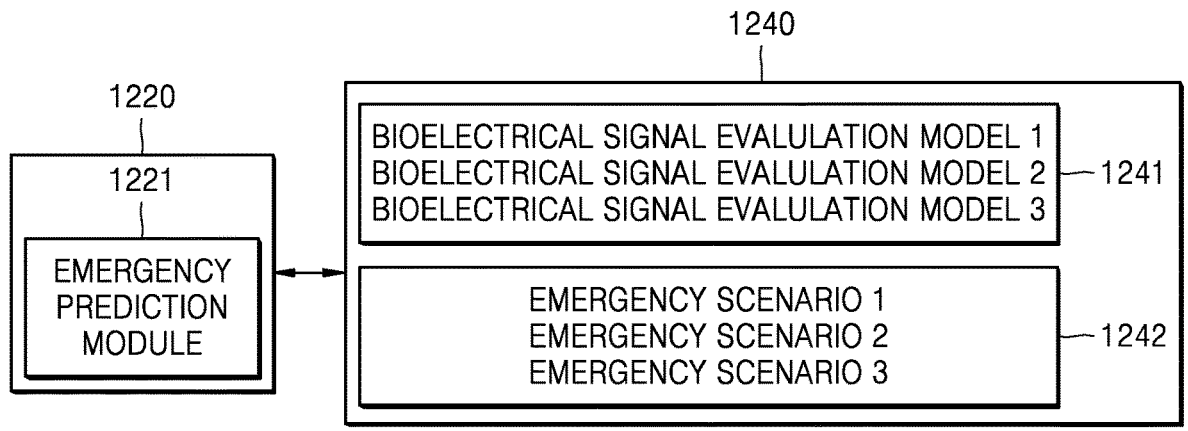
FIG. 61 is a view of a controller and a memory of a mobile device in the system of FIG. 60.

FIG. 59 is a view of a system 1000 for measuring bioelectrical signals according to another exemplary embodiment. FIG. 60 is a block diagram of a mobile device 1200 in the system 1000 of the present exemplary embodiment. FIG. 61 is a view of a controller 1220 and a memory 1240 of the mobile device 1200 in the system 1000 of FIG. 60.

Referring to FIG. 59, the system 1000 of the present exemplary embodiment includes an apparatus 1100 for measuring bioelectrical signals, and the mobile device 1200 wiredly or wirelessly connected to the apparatus 1100. The mobile device 1200 processes bioelectrical signals obtained by the apparatus 1100. The apparatus 1100 includes a sensor module 1110 for measuring bioelectrical signals of a person, and a main circuit 1120 for processing the bioelectrical signals measured by the sensor module 1110. The apparatus 1100 may be any of the apparatuses of FIGS. 1 through 58F. The apparatus 1100 may have an accessory shape usually worn on the person or may have a shape attached to an accessory usually worn on the person, and may usually measure bioelectrical signals of the person.

Referring to FIG. 60, the mobile device 1200 includes a communication circuit 1210, the controller 1220, the memory 1240, and a display 1250. Examples of the mobile device 1200 may include, but are not limited to, a mobile phone, a smart phone, a tablet computer, a personal digital assistant (PDA), and a laptop computer.

The communication circuit 1210 communicates with the communication circuit 145 (see FIG. 16) provided in the main circuit 1120 of the apparatus 1100. The communication circuit 1210 may include a wired communication module or a wireless communication module using, for example, wireless LAN, Wi-Fi, Bluetooth, ZigBee, WFD, UWB, infrared communication, BLE, and NFC. The communication circuit 1210 receives bioelectrical signal information processed by the main circuit 1120 of the apparatus 1100 and transmits a control command to the main circuit 1120 of the apparatus 1100.

The controller 1220 may process the bioelectrical signal information received from the main circuit 1120 into significant living body data. The controller 1220 may include an emergency prediction module 1221 as shown in FIG. 61. The emergency prediction module 1221 predicts an emergency of a subject who wears the apparatus 1100 from the living body data. The controller 1220 controls units in the mobile device 1200 such as the communication circuit 1210, the memory 1240, and the display 1250. The memory 1240 stores information related to a process of processing bioelectrical signals. For example, the memory 1240 may include bioelectrical signal evaluation models 1241 for evaluating bioelectrical signals in order for the controller 1220 to process bioelectrical signal information into significant living body data. Also, the memory 1240 may include emergency scenarios 1242 to be handled by the controller 1220 when the controller 1220 determines that an emergency occurs after the bioelectrical signals are evaluated. For example, the memory 1240 may include an address of a server of an emergency center to be contacted, an address of a server of a hospital to which a user usually goes, a personal computer in a house of the user, a phone number of a doctor in charge of the user, and a phone number of a guardian. The display 1240 may include a display that displays living body data or information related to the living body data. Furthermore, the mobile device 1200 may further include a well-known unit for transmitting information to the user such as a speaker or a vibration module.

Since the brain works without stopping, brain waves are generated at all times and diseases such as a stroke, a faint, a depression, a dementia, and an attention deficit hyperactivity disorder (ADHD) have unique brain wave features. Also, states where a person is sleepy and has a high stress level also have unique brain wave features. Accordingly, when the apparatus 1100 measures brain waves, the controller 1220 extracts brain wave features by processing received brain wave information. Brain wave signal evaluation models may include information about brain wave features of various diseases, and the emergency prediction module 1221 may match the brain wave features extracted by the controller 1220 to the brain wave features of the various diseases and may determine a sign of an abnormal condition of the subject. Furthermore, the emergency prediction module 1221 may assign scores to diseases according to whether the subject shows symptoms in an early stage, a mid stage, or an end stage, and may determine a current state of the subject according to risks or emergencies.

A detailed process performed by the emergency prediction module 1221 to determine a risk of a stroke based on brain wave signals will now be explained with reference to FIGS. 62 through 64.

Figure 62:
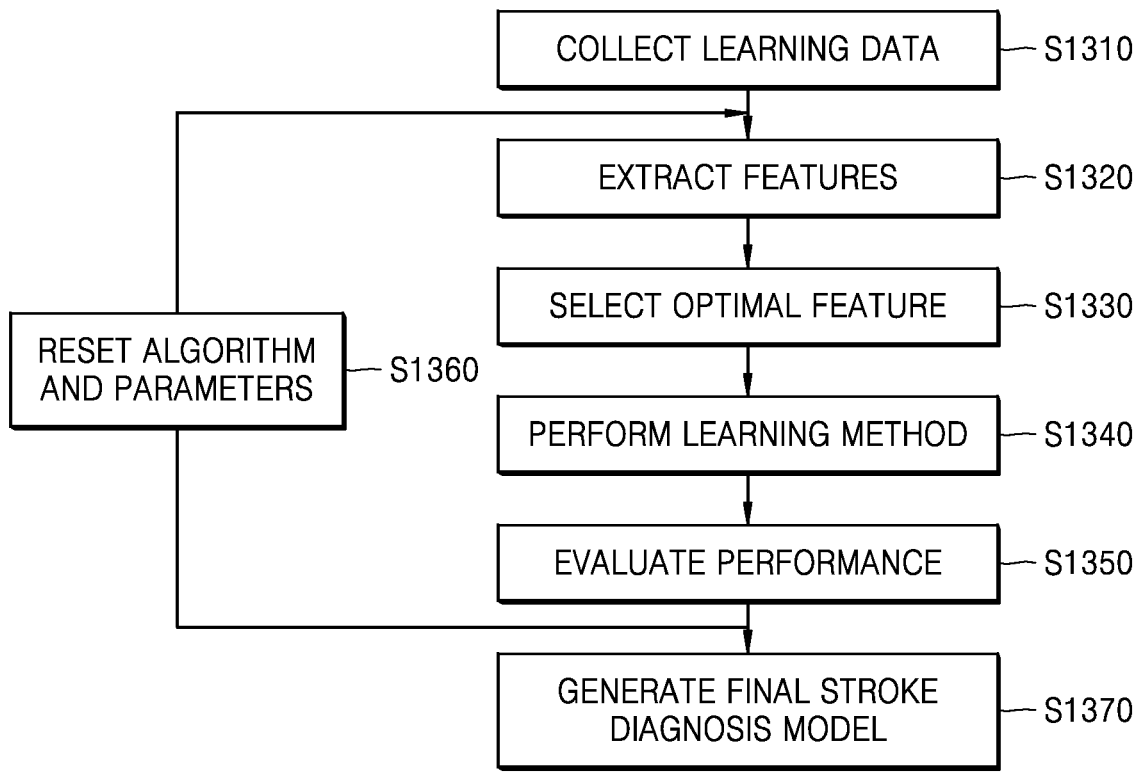
FIG. 62 is a view of a process of brain wave learning to diagnose a stroke.

FIG. 62 is a view of a process of brain wave learning to diagnose a stroke.

Referring to FIG. 62, in operation S1310, first, learning data related to a stroke is collected. For example, the learning data may include, for example, EEG signals, a gender, an age, whether to drink, and whether to smoke, and may include data of normal people and data of stroke patients.

Next, in operation S1320, features related to a stroke are extracted by processing the collected learning data. For example, various functions such as a frequency analysis function (e.g., wavelet-based fast Fourier transform (FFT)) and a complexity analysis function (e.g., multi-scale entropy (MSE) or correlation dimension) may be individually or collectively used.

Next, in operation S1330, an optimal feature having a high contribution to accuracy is selected from the extracted features. In order to select the optimal feature, an algorithm such as Chi squared test, recursive feature elimination, LASSO, elastic net, or ridge regression may be used.

Next, in operation S1340, a learning method is performed by using a learning algorithm and a parameter. Examples of the learning method may include a multilayer perceptron, a decision tree, a support vector machine, and a Bayesian network.

Next, in operation S1350, performance is evaluated by using an evaluation method such as cross validation. In operation S1360, an algorithm and parameters are reset, and operations 1320 through 1340 are repeatedly performed. In operation S1370, a stroke diagnosis model is generated.

The stroke diagnosis model may be generated by an additional learning device and may be input to the mobile device 1200. Alternatively, the stroke diagnosis model may be generated by allowing the mobile device 1200 to perform a learning process. When the mobile device 1200 performs a learning process, a neural network circuit may be provided in the mobile device 1200 in a hardware or software manner.

Figure 63:
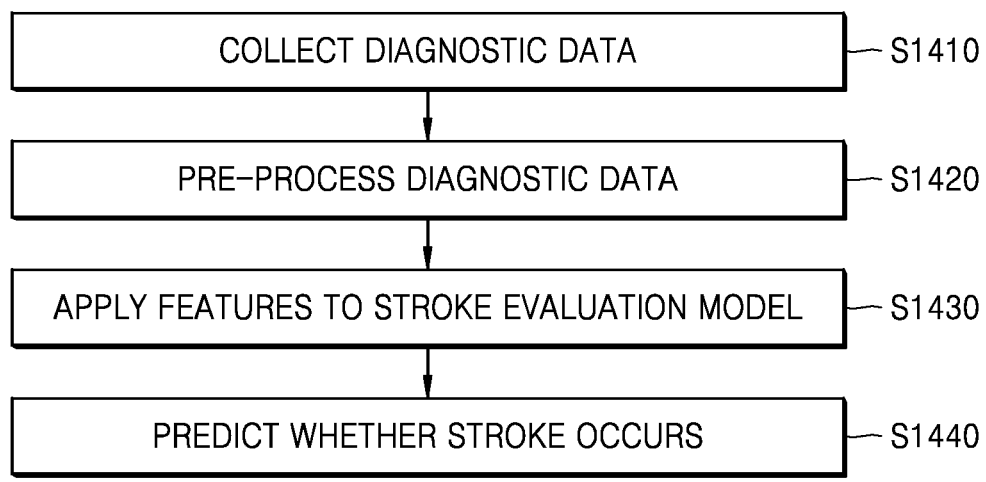
FIG. 63 is a flowchart of a process of evaluating a stroke.

FIG. 63 is a flowchart of a process performed by the mobile device 1200 to evaluate a stroke.

Referring to FIG. 63, in operation S1410, the mobile device 1200 collects diagnostic data. The diagnostic data includes bioelectrical signals such as brain wave signals sensed by the apparatus 1100. Part of the diagnostic data may be input by a user or a third person (e.g., a health care provider or a manufacturer). The diagnostic data may be data under the same condition as that of learning data.

Next, in operation S1420, the controller 1220 of the mobile device 1200 extracts features by pre-processing the diagnostic data. The pre-processing may be performed in the same manner as that used to perform a learning process. The pre-processing may extract features from the diagnostic data.

Next, in operation S1430, the extracted features are applied to a stroke evaluation model. In operation S1440, whether a stroke occurs is predicted by evaluating whether the extracted features are matched to the stroke evaluation model.

The predicting whether a stroke occurs may include determining a risk of a stroke.

Table 1 shows stroke evaluation models.

TABLE 1

| Model | NIHSS score | Risk of Stroke |
|---|---|---|
| Group 0 | 0 \| 1-42 | Entire test set |
| Group 1 | 0 \| 1-4 | Low level |
| Group 2 | 0 \| 5-15 | Medium level |
| Group 3 | 0 \| 16-20 | High level |
| Group 4 | 0 \| 21-42 | Highest level |

National Institutes of Health Stroke Scale (NIHSS) is a tool used by the U.S. health care providers to quantify the impairment caused by a stroke and groups in Table 1 are divided according to NIHSS scores. The group 0 evaluation model is a model for evaluating whether a stroke occurs and the group 1-4 evaluation models are models for evaluating risk levels of a stroke.

Figure 64:
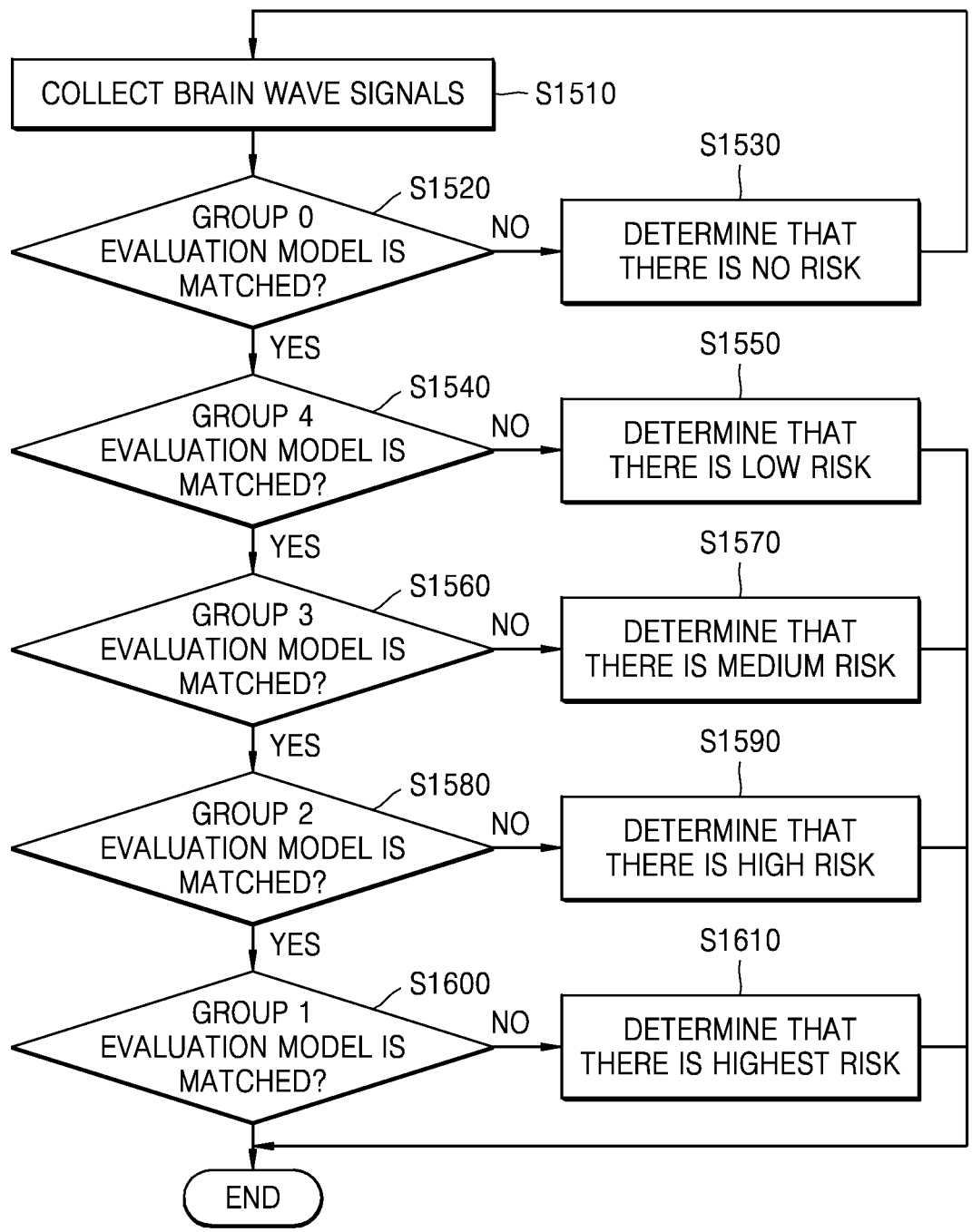
FIG. 64 is a flowchart of a process of determining a risk according to stroke evaluation.

FIG. 64 is a flowchart of a process of determining a risk according to stroke evaluation using the group 0-4 evaluation models.

Referring to FIG. 64, in operation S1510, brain wave signals are continuously collected. In operation S1520, the obtained brain wave signals are matched to the group 0 evaluation model. If the obtained brain wave signals are not matched to the group 0 evaluation model, an operation of obtaining brain wave signals is repeatedly performed and whether a stroke occurs is continuously monitored. When the obtained brain wave signals are not matched to the group 0 evaluation model, it means that a value obtained by applying the obtained brain wave signals to the group 0 evaluation model corresponds to an NIHSS score of 0. Since the NIHSS score of 0 indicates that a stroke does not occur, if the obtained brain wave signals are not matched to the group 0 evaluation model, in operation S1530, it may be determined that a stroke does not occur and there is no risk of a stroke.

If the obtained brain wave signals are matched to the group 0 evaluation model, the process proceeds to an operation of evaluating a risk level of the stroke. In other words, when a value obtained by applying the obtained brain wave signals to the group 0 evaluation model is equal to or greater than an NIHSS score of 1, in operations S1540 through S1610, it may be determined that a stroke occurs and an operation of evaluating a risk level of the stroke is performed.

In operation S1540, the obtained brain wave signals are matched to the group 4 evaluation model. In operation S1550, when a value obtained by applying the obtained brain wave signals to the group 4 evaluation model is within a range from an NIHSS score of 21 to 42, it is determined that a risk of the stroke has a highest level. If a value obtained by applying the obtained brain wave signals to the group 4 evaluation model exceeds the range from NIHSS score of 21 to 42, the process proceeds to operation S1560 in which the obtained brain wave signals are matched to the group 3 evaluation model.

Next, in operation S1560, the obtained brain wave signals are matched to the group 3 evaluation model. When a value obtained by applying the obtained brain wave signals to the group 3 evaluation model is within a range from an NIHSS score of 16 to 20, in operation S1570, it is determined that a risk of the stroke has a high level. When a value obtained by applying the obtained brain wave signals to the group 3 evaluation model exceeds the range from an NIHSS score of 16 to 20, the process proceeds to operation S1580 in which the obtained brain waves are matched to the group 2 evaluation model.

Next, in operation S1580, the obtained brain waves are matched to the group 2 evaluation model. When a value obtained by applying the obtained brain wave signals to the group 2 evaluation model is within a range from an NIHSS score of 5 to 15, in operation S1590, it is determined that a risk of the stroke has a medium level. When a value obtained by applying the obtained brain wave signals to the group 2 evaluation model exceeds the range from an NIHSS score of 5 to 15, the process proceeds to operation S1600 in which the obtained brain waves are matched to the group 1 evaluation model.

Next, in operation S1600, the obtained brain waves are matched to the group 1 evaluation model. When a value obtained by applying the obtained brain wave signals to the group 1 evaluation model is within a range from an NIHSS score of 1 to 4, in operation S1610, it is determined that a risk of the stroke has a low level. When a value obtained by applying the obtained brain wave signals to the group 1 evaluation model exceeds the range from an NIHSS score of 1 to 4, the process ends, and returns to operation S1510 in which brain waves are obtained.

A risk of a stroke may be evaluated by combining evaluation models using different methods. For example, assuming that an FFT method, an MSE method, and a correlation dimension method are used, an evaluation model FFT_MODEL using results of the FFT method, an evaluation model MSE_MODEL using results of the MSE method, and an evaluation model Corel_MODEL using results of the correlation dimension method may be combined and performance may be evaluated by using cross validation. Evaluation results TrainResult of the evaluation models are obtained to have values from 0 to 1. Weight values may be calculated by applying Equations 1 through 3 to the evaluation results of the evaluation models.

$$Weight_{FFTMODEL} = \frac{TrainResult_{FFTMODEL}}{(TrainResult_{FFTMODEL} + TrainResult_{MSEMODEL} + TrainResult_{CorelMODEL})} \quad \text{Equation 1}$$

$$Weight_{MSEMODEL} = \frac{TrainResult_{MSEMODEL}}{(TrainResult_{FFTMODEL} + TrainResult_{MSEMODEL} + TrainResult_{CorelMODEL})} \quad \text{Equation 2}$$

$$Weight_{CorelMODEL} = \frac{TrainResult_{CorelMODEL}}{(TrainResult_{FFTMODEL} + TrainResult_{MSEMODEL} + TrainResult_{CorelMODEL})} \quad \text{Equation 3}$$

A final stroke evaluation result PredictResult may be obtained by using Equation 4.

$$PredictResult = PredictResult_{FFTMODEL} \times Weight_{FFTMODEL} + PredictResult_{MSEMODEL} \times Weight_{MSEMODEL} + PredictResult_{CorelMODEL} \times Weight_{CorelMODEL} \quad \text{Equation 4}$$

In Equation 4, the final stroke evaluation result is obtained to have a value from 0 to 1 which shows a possibility of a stroke.

Table 2 shows a possibility of a stroke according to a value of the final stroke evaluation result.

TABLE 2

| PredictResult (x) | Possibility of Stroke |
|---|---|
| 0 ≤ x < 0.3 | Low |
| 0.3 ≤ x < 0.7 | Medium |
| 0.7 ≤ x ≤ 1 | High |

As described above with respect to FIG. 61, the emergency prediction module 1221 may determine a risk of a stroke based on brain wave signals received from the apparatus 1100, and if the emergency prediction module 1221 determines that a subject is in an emergency, the controller 1220 may perform a process according to an emergency scenario that is stored in the memory 1240.

For example, when the emergency prediction module 1221 determines that the subject is in an initial stage of a stroke, an operation of notifying the subject that the subject is in an initial stage of the stroke may be performed through the display 1250 of the mobile device 1200. When the emergency prediction module 1221 determines that the subject is in a severe stage of a stroke, the controller 1220 may perform an operation of notifying that the subject is in a severe stage of the stroke to a guardian or a hospital or an emergency center that is previously stored through the communication circuit 1210. Furthermore, when the emergency prediction module 1221 determines that the subject is in a most severe stage of a stroke or in an emergency, the controller 1220 may notify at a highest volume that the subject is in an emergency through a speaker (not shown) of the mobile device 1200, or may notify an emergency worker or a doctor who is near to a user through a server of the hospital or the emergency center that is previously stored to handle the emergency. When the emergency prediction module 1221 determines that the subject is in a most severe stage of the stroke or in an emergency, the controller 1220 may request a mobile communication service provider to transmit a message indicating the emergency and requesting for help to a mobile device that may communicate and is adjacent to the user.

Figure 65:
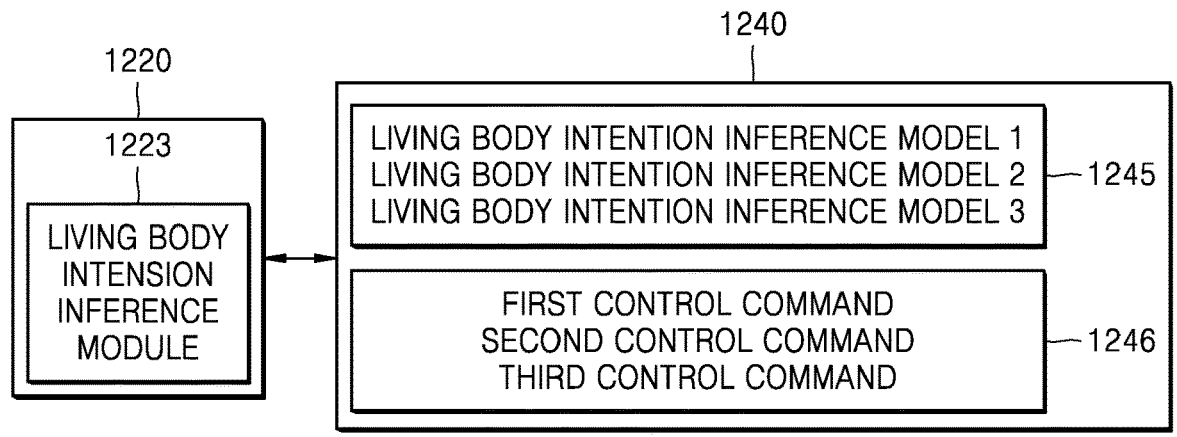
FIG. 65 is a block diagram of the controller and the memory of a mobile device in the system of FIG. 59, according to another exemplary embodiment.

FIG. 65 is a block diagram of the controller 1220 and the memory 1240 of a mobile device 1201 according to another exemplary embodiment. Other elements are substantially the same as those of the mobile device 1200 of FIG. 60 except a living body intention inference module 1223 and the memory 1240. Referring to FIG. 65, the living body intention inference module 1223 infers what a living body who wears the apparatus 1100 thinks, that is, an intention of the living body, from processed bioelectrical signal information. The memory 1240 includes living body intention inference models 1245 and stores a control command set 1246 predicted by the living body intention inference models 1245.

The living body intention inference models 1245 model a correlation between patterns of bioelectrical signals and intentions of the living body. For example, when the apparatus 1100 measures brain waves, frequency components of received brain wave information may be analyzed and brain waves may be classified into α waves, β waves, and γ waves. The brain waves classified into the α waves, the β waves, and the γ waves are mostly generated in a region with frequencies from about 1 Hz to about 20 Hz and a region with frequencies in which the brain waves are mostly generated varies according to an activity state of the brain. The brain waves classified into the α waves, the β waves, and the γ waves are related with the activity state of the brain. For example, the α waves that are mostly measured in the frontal lobe and the temporal lobe are mostly generated when the brain is in a relaxed state. The β waves that are generated when the living body is anxious, nervous, or concentrates are most strongly generated in the frontal lobe. When characteristics of frequencies and positions at which brain waves are generated are combined with each other, which part of the brain is now activated may be predicted. Considering that the brain has a specific function according to each position, information about an activity of the brain may be obtained. The living body intention inference module 1223 matches obtained brain wave signals to living body intention inference models and infers an intention of a user from the living body intention inference models. The controller 1220 (see FIG. 60) may generate a control command for the mobile device 1200 or another electronic device based on the intention of the user inferred by the living body intention inference module 1223.

Although the emergency prediction module 1221 (see FIG. 61) or the living body intention inference module 1223 (see FIG. 65) is provided in the mobile device 1220 in the previous exemplary embodiments, both the emergency prediction module 1221 and the living body intention inference module 1223 may be provided in the mobile device 1200. Also, the mobile device 1200 may include a health care module and an administration management module that are customized to the user based on living body data processed by the controller 1220.

Figure 66:
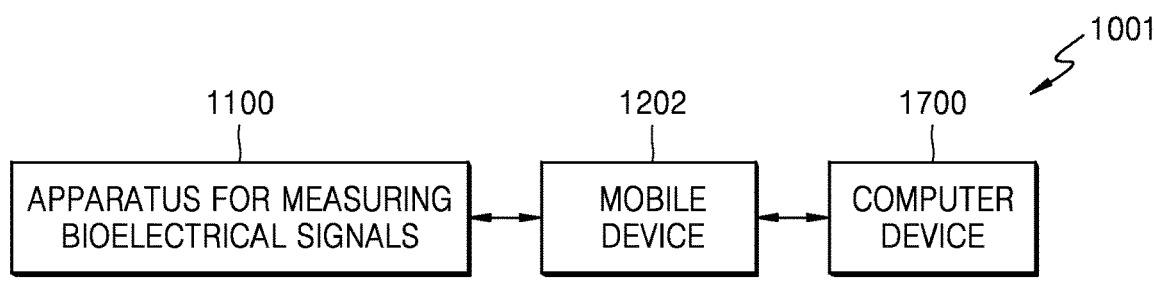
FIG. 66 is a view of a system for processing bioelectrical signals, according to another exemplary embodiment.
Figure 67:
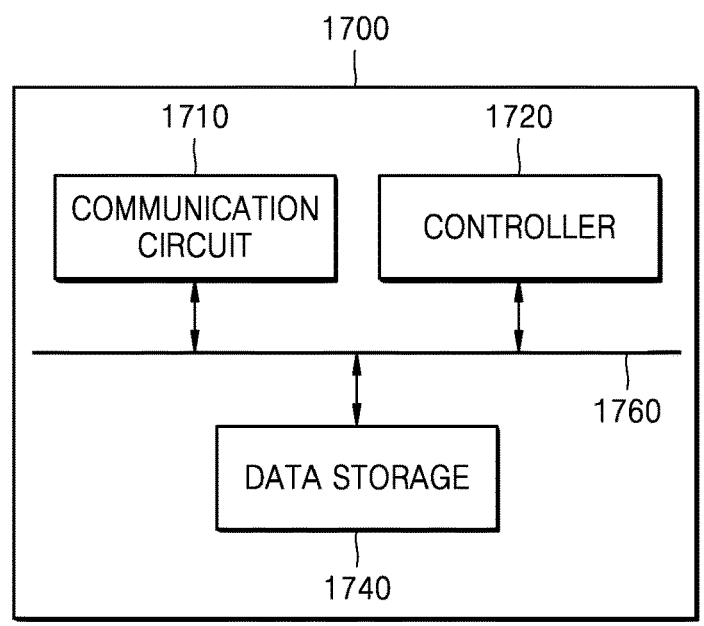
FIG. 67 is a block diagram of a computer device in the system of FIG. 66.

FIG. 66 is a view of a system 1001 for processing bioelectrical signals according to another exemplary embodiment. FIG. 67 is a block diagram of a computer device 1700 in the system 1001 of FIG. 66. Referring to FIGS. 66 and 67, the system 1001 of the present exemplary embodiment may include the apparatus 1100, a mobile device 1202 wiredly or wirelessly connected to the apparatus 1100, and the computer device 1700 directly connected or connected through a network to the mobile device 1202.

The computer device 1700 includes a communication circuit 1710 that communicates with the mobile device 1202, a data storage 1740 that stores information related to a process of processing bioelectrical signals, and a controller 1720 that controls each unit in the computer device 1700. The communication circuit 1710 may include a wired communication module or a wireless communication module using, for example, wireless LAN, Wi-Fi, Bluetooth, ZigBee, WFD, UWB, infrared communication, BLE, or NFC.

The computer device 1700 may process at least some or all of bioelectrical signals. In this case, the mobile device 1202 transmits bioelectrical signals received from the apparatus 1100 to the computer device 1700 and receives bioelectrical signal information analyzed by the computer device 1700. Although the mobile device 1200 or 1201 processes bioelectrical signals to analyze a risk of a stroke or infer an intention of a user in the previous exemplary embodiments, the mobile device 1202 of the present exemplary embodiment performs part of a process of processing bioelectrical signals or does not perform the process of processing bioelectrical signals at all, and transmits bioelectrical signals received from the apparatus 1100 to the computer device 1700 or transmits bioelectrical signals only some of which are processed to the computer device 1700. The data storage unit 1740 may include bioelectrical signal evaluation modules that are used to evaluate bioelectrical signals, and the controller 1720 may determine an emergency of the user or may infer an intention of the user from brain wave signals received from the mobile device 1202 based on the bioelectrical signal evaluation models.

Examples of the computer device 1700 may include a server of a hospital, a server of an emergency center, and a personal computer in a house of the user. The mobile device 1202 may transmit living body information of the user collected through the apparatus 1100 to the computer device 1700, and the computer device 1700 may store the received living body information of the user and may perform a post-process according to a scenario corresponding to a current state of the user.

Alternatively, the computer device 1700 may be an electronic device that may be controlled by the mobile device 1202. In this case, the system 1001 may be obtained by adding the computer device 1700 to the system 1000 of FIGS. 59 through 65. That is, a process of processing bioelectrical signals to analyze a risk of a stroke or infer an intention of the user may be performed by the mobile device 1202, and the computer device 1700 may be an electronic device (e.g., an electric home appliance such as a TV, a lighting device, a doorlock, or an air conditioner) that is controlled by the mobile device 1202. For example, when the apparatus 1100 measures brain waves of the user, the mobile device 1202 may infer an intention of the user and may generate a control command for controlling the computer device 1700.

Figure 68:
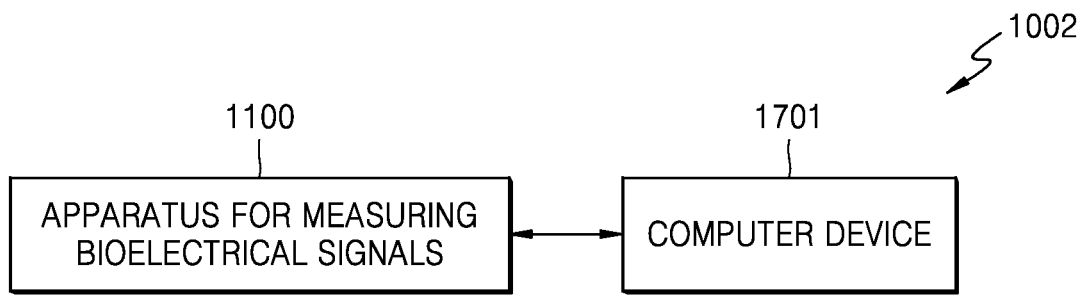
FIG. 68 is a view of a system for processing bioelectrical signals, according to another exemplary embodiment.

FIG. 68 is a view of a system 1002 for processing bioelectrical signals according to another exemplary embodiment. Referring to FIG. 68, the system 1002 includes the apparatus 1100 and a computer device 1701 connected through a network to the apparatus 1100. The apparatus 1100 of the present exemplary embodiment is directly connected to the computer device 1701 without the mobile device 1200 (see FIG. 59). The apparatus 1100 may include the communication circuit 145 (see FIG. 16) that may connect to the network, and may connect through the network to the computer device 1701.

A process of processing bioelectrical signals of FIGS. 60 through 65 may be performed by the apparatus 1100. For example, the controller 141 in the main circuit 140 (see FIG. 16) of the apparatus 1100 may include an emergency prediction module or a living body intention prediction module, and the memory 144 may store information about various bioelectrical signal evaluation models and emergency scenarios. The controller 141 determines a body state of a user based on sensed bioelectrical signals, and controls postprocesses according to information about the determined body state. Alternatively, a process of processing bioelectrical signals may be performed by the computer device 1701 as described with reference to FIGS. 66 and 67.

Examples of the computer device 1701 may include a server of a hospital or an emergency center, a desktop computer in a house of the user, and a notebook. Furthermore, the computer device 1701 may be an electric home appliance that may connect to a network. For example, when there is a network environment including a wireless access point (WAP) in the house of the user and electric home appliances may connect to a network, the apparatus 1100 may control the electric home appliances by connecting to the network through the WAP.

Figure 69:
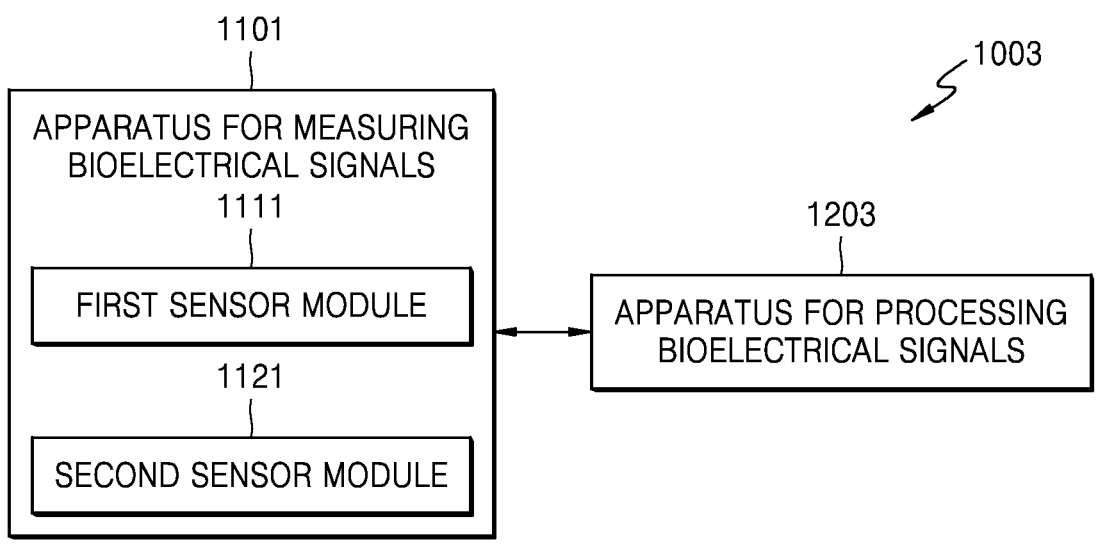
FIG. 69 is a block diagram of a system for processing bioelectrical signals, according to another exemplary embodiment.

FIG. 69 is a block diagram of a system 1003 for processing bioelectrical signals according to another exemplary embodiment. Referring to FIG. 69, the system 1003 of the present exemplary embodiment includes an apparatus 1101 for measuring bioelectrical signals and an apparatus 1203 for processing bioelectrical signals. The apparatus 1101 includes a first sensor module 1111 and a second sensor module 1121. The first sensor module 1111 may include a sensor electrode that measures bioelectrical signals. The system 1003 may be obtained by adding the second sensor module 1121 to the apparatus for measuring bioelectrical signals of any of FIGS. 1 through 58F. The second sensor module 1121 includes an additional sensor that measures a state of a living body in addition to electrical sensor signals. For example, the second sensor module 1121 may include at least one of a gyroscope sensor, an acceleration sensor, a global positioning system (GPS), a terrestrial magnetism sensor, and a light sensor. The apparatus 1101 obtains bioelectrical signal information from bioelectrical signals of the user through the first sensor module 1111, and collects ambient information about whether the user falls down or the user wanders. The apparatus 1101 may transmit the ambient information along with the bioelectrical signal information to the apparatus 1203, and the apparatus 1203 may collect the bioelectrical signal information and the ambient information and may more accurately determine a current state of the user. When the apparatus 1203 is a mobile device that is carried by the user, the second sensor module 1121 may be provided in the apparatus 1203, not in the apparatus 1101.

Next, examples to which the system for processing bioelectrical signals of the previous exemplary embodiments will now be explained.

The system for processing bioelectrical signals of any of the previous exemplary embodiments may be applied to medical areas. An apparatus for measuring bioelectrical signals may be manufactured as any of various devices and may be used in daily life as described above. For example, the apparatus for measuring bioelectrical signals may be manufactured as a cap, glasses, a hair band, a hair pin, an eye bandage, a patch, a pillow, a watch, a necklace, or a head-mounted display (HMD) or may be coupled thereto. Accordingly, when a user usually wears the apparatus for measuring bioelectrical signals, living body information of the user may be transmitted to a hospital and a disease may be prevented or rapidly diagnosed. For example, a disease is monitored by using brain waves, and when an emergency is predicted or determined, the emergency may be notified to the user and the disease (e.g., epilepsy or a stroke) along with ambient information such as a position of the user may be transmitted to a medical institution or a health care provider so that the disease is diagnosed, the emergency is handled, and the user is treated.

Alternatively, when a dementia patient loses his/her way, nervousness or embarrassment may be analyzed and state information along with position information of the dementia patient when the dementia patient wanders for a long time through a path different from a path through which he/she usually passes may be provided to a friend or a policeman to prevent disappearance.

Alternatively, a customized neurofeedback (that is a training process for enhancing concentration) may be provided according to personal details of a user (e.g., an ADHD symptom or an age).

Alternatively, a depression scale may be generated from bioelectrical signals and may be notified to a user or a health care provider, to enable the user or the health care provider to continuously make a diagnosis. For example, if a depression scale is increased when brain wave are measured, a message requesting or ordering the user to take a depression medicine may be output to manage administration. Alternatively, a current treatment stage according to administration of a depression medicine may be obtained by measuring brain waves, constant treatment may be urged, effect according to an administration history may be predicted by measuring brain waves, and a difference between states before and after administration may be notified. The effect of administration may be notified in order for the user to have a will to recover and help the user to endure a long treatment period. Also, history information may be shared with a friend and a health care provider to take an appropriate action.

Alternatively, brain waves of a baby may be measured to recognize an intention of the body. Since brain waves are used, even when the baby does not cry, an intention of the body may be recognized and a state (where he/she is, for example, hungry, bored state, uncomfortable, stressed, asleep, awake, happy, or sad) may be recognized.

Alternatively, multimodal information using various form factors may be extracted. For example, an intention may be accurately predicted or health care may be obtained by measuring signals corresponding to a body temperature, a heart rate, a nodding event, an eye-blinking event, or a tossing event as well as brain waves.

Alternatively, the system for processing bioelectrical signals of any of the previous exemplary embodiment may be applied to safety and transport areas. Since an apparatus for measuring bioelectrical signals may be manufactured as any of various devices as described above, the apparatus for measuring bioelectrical signals may be manufactured as a driver's seat, a cap, glasses, a hair band, a hair pin, an eye bandage, a patch, or a pillow, or may be coupled thereto. Accordingly, the apparatus for measuring bioelectrical signals may usually measure bioelectrical signals of a user. For example, when an apparatus for measuring bioelectrical signals including a brain wave sensor is worn on the head, a state of a worker in any safety or transport area (where the worker is, for example, sleepy or has low concentration) may be detected and an alarm may be output.

Alternatively, the system for processing bioelectrical signals of any of the previous exemplary embodiments may be applied to game areas. For example, an apparatus for measuring bioelectrical signals may be worn on the head and a game may be controlled or an effect may be output. Alternatively, a virtual character may be controlled through a brain computer interface (BCI) by transmitting a command using brain waves. Alternatively, an interactive game effect may be obtained by using a brain wave state (e.g., feeling). For example, when a user is excited, a virtual character may be displayed on a screen or an effect may be reflected on a game.

Alternatively, the system for processing bioelectrical signals of any of the previous exemplary embodiments may be applied to electric home appliances. An apparatus for measuring bioelectrical signals may be manufactured as any of various devices and may be used in daily life as described above. For example, the apparatus for measuring bioelectrical signals may be manufactured as a cap, glasses, a hair band, a hair pin, an eye bandage, a patch, a pillow, a watch, or a necklace, or may be coupled thereto. For example, the apparatus for measuring bioelectrical signals may be worn on the head and may enable a user to output a command to a smart home and an electric home appliance.

Alternatively, a state of a user may be monitored by using the apparatus for measuring bioelectrical signals, and when the user is in an emergency (for example, he or she suddenly falls down or has a brain disorder), the emergency may be notified to an emergency center through a smart home.

Alternatively, a state of a user may be monitored in real time by additionally using a BT (Bluetooth), a GPS, an acceleration sensor, or a motion sensor, and may be transmitted to a smart home (e.g., an electric home appliance).

Alternatively, a sleep state and a sleep depth may be detected by using brain waves, a command to operate a smart electric home appliance may be transmitted, and a lighting brightness, an indoor temperature, an indoor humidity, and so on when a user goes to bed, sleeps, and wakes up may be controlled by detecting sleep brain waves.

Alternatively, background music may be controlled when a user goes to bed and wakes up by detecting sleep brain waves.

Alternatively, when a user watches multimedia content such as a TV program, brain waves of the user may be analyzed, an interval having high interest/concentration of the user may be selected, highlighted content may be formed, and the highlighted content may be shared with friends through the cloud or by connecting devices.

Alternatively, brain waves of a baby may be measured to recognize an intention of the baby. Since brain waves are used, even when the baby does not cry, an intention of the baby may be recognized and a state (where he/she is, for example, hungry, bored, uncomfortable, stressed, asleep, awake, happy, or sad) may be recognized.

Alternatively, multimodal information such as a body temperature, a heart rate, a nodding event, an eye-blinking event, or a tossing event as well as brain waves may be additionally extracted by using various form factors, to accurately predict an intention or obtain health care.

Alternatively, the system for processing bioelectrical signals of any of the previous exemplary embodiments may be combined with a mobile device and may be applied to daily life. An apparatus for measuring bioelectrical signals may be worn on the head and a health care monitoring system that analyzes brain waves of a user in real time may be established. For example, the apparatus for measuring bioelectrical signals may be worn on the head and a smart phone may be manipulated by using brain waves.

Alternatively, brain waves may be analyzed in real time, an alarm may be instantly output when a problem occurs, a specific application may be executed through user brain wave learning, or a letter may be input.

Alternatively, administration may be managed by using brain waves. Brain waves before and after a medicine is taken may be compared with each other and a case where a medicine is not taken even after a time to take the medicine may be detected and an alarm may be output.

Alternatively, when a photograph is taken, emotion may be stored with the photograph, and later emotion information may be displayed along with the photograph and a photo serendipity service for improving memory through retrospection may be provided.

Alternatively, a shutter may be pressed by using brain waves. Furthermore, photographing may be performed by analyzing an image of the face of a user by using brain waves.

Alternatively, emotion such as happiness, melancholy, impression, sadness, anger, or love when a photograph is stored may be analyzed by using brain waves.

Alternatively, in order for a photograph to be naturally used according to the use of a terminal, the photograph may be displayed on a home screen or an electronic lock screen of the terminal. In addition, when a position, a time, and a person-related quiz of the photograph may be provided on the electronic lock screen and when a correct answer is input, the lock may be opened to improve memory.

Alternatively, a time when concentration is high during the day may be notified by using brain waves, a condition may be recorded, and a diary may be automatically made. For example, a time when concentration is high during the day may be automatically notified, to help a user to record a condition. Conditions at important time points during the day may be automatically made as a diary by using written memos.

Alternatively, emotion such as melancholy may be measured by using brain waves, and an emoticon or a photograph suitable for the emotion may be posted on a social network service (SNS)/blog to attract attention.

Alternatively, an easy input function may be provided by analyzing emotion such as melancholy through a facial expression, a tone on the phone, or a personal message of an SNS/blog.

Alternatively, when emotion is shared on an SNS/blog, the attention of friends may be drawn by using various UI/UX methods such as an emoticon, a photograph, and music.

Alternatively, customized melancholy may be determined in consideration of a nature or an environment of a person.

Alternatively, a preference of a user during online or offline shopping may be recognized by using brain waves, and a bookmark service may be provided.

Alternatively, the system for processing bioelectrical signals of any the previous exemplary embodiments may be applied to education areas. An apparatus including a brain wave sensor may be worn on the head and a customized education service according to the educational achievement and interest of a user may be provided. Also, a customized service for an education curriculum, a degree of difficulty, and an education method may be provided by analyzing a degree of concentration, a degree of excitement, and a stress index of a student. Furthermore, additional information (e.g., a hint) for enhancing education or a stimulus for improving concentration may be provided by recognizing a degree of understanding and a degree of concentration of a student by using brain waves, and a degree of difficulty in each class may be adjusted by changing a type of content according to the degree of understanding.

Alternatively, the system for processing bioelectrical signals of any of the previous exemplary embodiments may be applied to entertainment areas. An apparatus including a brain wave sensor may be worn on the head and a service for recommending content according to the emotion of a user may be provided. Also, a degree of concentration, a stress index, and nervousness may be generally measured, a background screen may be changed according to the emotion of the user, a song may be automatically recommended according to the emotion of the user, an application may be recommended according to the emotion of the user, a gourmet restaurant may be recommended according to the emotion of the user, a place may be recommended according to the emotion of the user, a destination in travel may be recommended according to the emotion of the user, shopping content may be recommended according to the emotion of the user, a screen brightness may be recommended according to the emotion of the user, a screen font may be changed according to the emotion of the user, and a picture frame (or a photograph) may be provided according to the emotion of the user.

Figure 70:
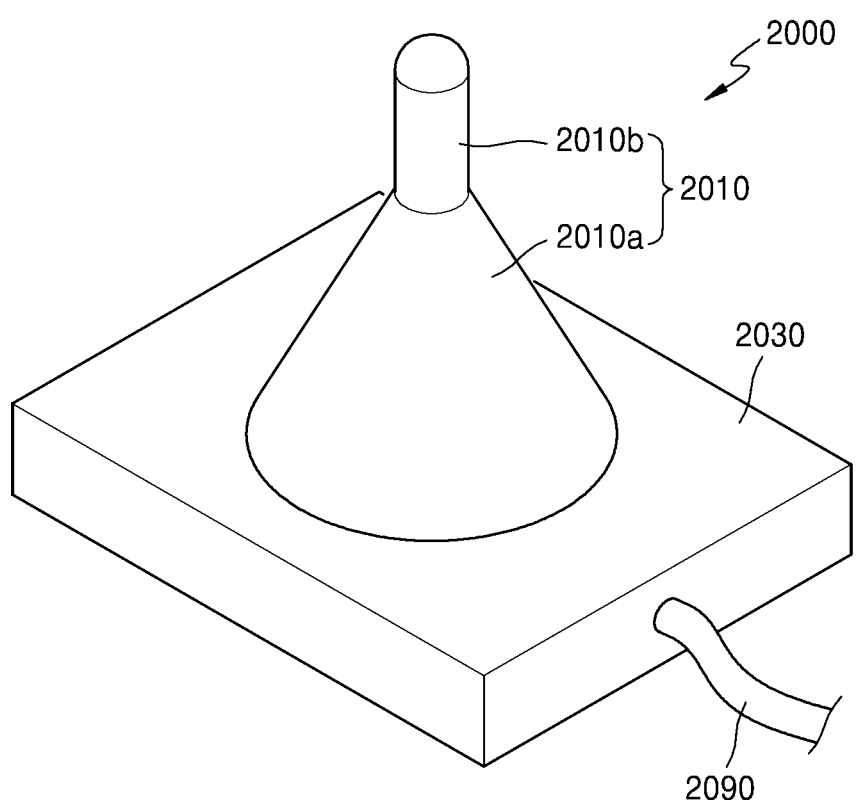
FIG. 70 is a view of a sensor electrode for measuring bioelectrical signals, according to another exemplary embodiment.
Figure 71:
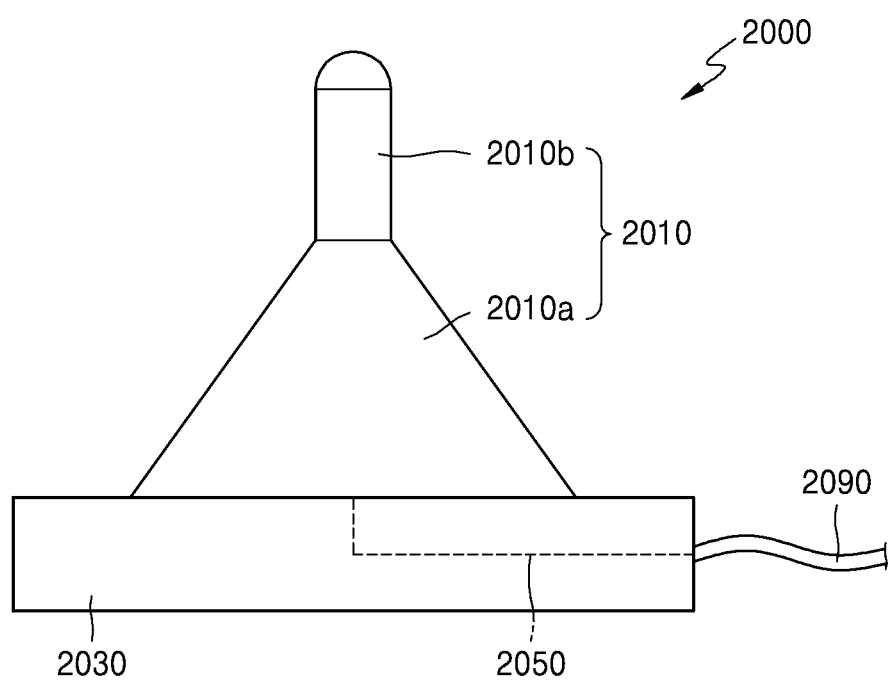
FIG. 71 is a side view of the sensor electrode of FIG. 70.

FIG. 70 is a view of a sensor module 2000 for measuring bioelectrical signals according to another exemplary embodiment. FIG. 71 is a side view of the sensor module 2000 of FIG. 70.

Referring to FIGS. 70 and 71, the sensor module 2000 of the present exemplary embodiment includes a sensor electrode 2010.

The sensor electrode 2010 contacts a body part and detects bioelectrical signals. The body part may be the head, eyes, forearm, wrist, or breast of a living body. Bioelectrical signals measured by the sensor electrode 2010 may be brain waves, EOG signals, EMG signals, ENG signals, or ECG signals according to the body part that contacts the sensor electrode 2010. The sensor electrode 2010 may be a dry electrode having a funnel shape and including a tapering portion 2010a that has a tapering shape and a protruding portion 2010b that extends from one end of the tapering portion 2010a.

The protruding portion 2010b has a flexibility that is greater than that of the tapering portion 2010a. When the sensor electrode 2010 contacts the scalp, the tapering portion 2010a supports the protruding portion 2010b and the protruding portion 2010b is bent and contacts the scalp. In order to satisfy such a flexibility relationship, the sensor electrode 2010 may have a hardness ranging, for example, from about 40° to about 60°.

Regarding a longitudinal section of the sensor electrode 2010 along a bottom surface of the other end of the tapering portion 2010a, that is, a mount surface of an electrode supporter 2030 on which the sensor electrode 2010 is mounted, a gradient of an outer circumferential surface of the protruding portion 2010b may be greater than a gradient of an outer circumferential surface of the tapering portion 2010a. In other words, the protruding portion 2010b may have a prism shape or a tapering shape having a gradient that is greater than a gradient of the tapering portion 2010a. For example, the tapering portion 2010a may have a circular cone shape, an elliptic cone shape, or a polypyramid shape (strictly, a truncated cone shape), and the protruding portion 2010b may have a cylindrical shape, an elliptic cylindrical shape, or a prism shape.

One end of the protruding portion 2010b may have a blunt shape such as a hemispheric shape so that when the protruding portion 2010b contacts the living body, pain in the living body is minimized. The tapering portion 2010a and the protruding portion 2010b may be integrally formed with each other. A shape of the end of the protruding portion 2010b is not limited thereto, and may be sharp or flat. A height of the protruding portion 2010b may be greater than a diameter of the protruding portion 2010b.

The tapering portion 2010a and the protruding portion 2010b may be integrally formed by using the same material. In this case, the tapering portion 2010a and the protruding portion 2010b of the sensor electrode 2010 may be formed of a flexible conductive synthetic resin material. For example, the sensor electrode 2010 may be formed of a conductive polymer such as conductive silicone or conductive rubber. Since a diameter of the protruding portion 2010b is less than a diameter of the tapering portion 2010a, the protruding portion 2010b may be more easily bent than the tapering portion 2010a.

Alternatively, the tapering portion 2010a and the protruding portion 2010b may be separately manufactured and then may be adhered to each other. In this case, the tapering portion 2010a and the protruding portion 2010b may be formed of the same material or different materials. For example, the protruding portion 2010b may be formed of conductive silicone or conductive rubber having a high flexibility, and the tapering portion 2010a may be formed of a hard synthetic resin or a synthetic resin having a flexibility that is less than that of the protruding portion 2010b. The tapering portion 2010a may be formed of a conductive material or a non-conductive material. When the tapering portion 2010a is formed of a non-conductive material, an additional conductor that is electrically connected to the protruding portion 2010b may be inserted into the tapering portion 2010a.

The sensor module 2000 may further include the electrode supporter 2030 to which the other end of the tapering portion 2010a is attached and that supports the sensor electrode 2010. The electrode supporter 2030 that supports the sensor electrode 2010 may be a housing of the sensor module 2000, an additional substrate, or a part of a main body.

For example, the electrode supporter 2030 may be formed of a non-conductive material. For example, the electrode supporter 2030 may be formed of a plastic resin. The plastic resin may be hard or soft. A wiring circuit 2050 (see FIG. 71) of the sensor electrode 2010 may be buried in the electrode supporter 2030, or may be formed as a printed circuit on a surface that is opposite to a surface of the electrode supporter 2030 on which the sensor electrode 2010 is provided. Bioelectrical signals detected by the sensor electrode 2010 are transmitted to a measuring apparatus through a cable 2090.

Alternatively, the electrode supporter 2030 may be formed of a conductive material. In this case, the sensor electrode 2010 and the electrode supporter 2030 may be formed of the same material and the electrode supporter 2030 may be understood as a part of the sensor electrode 2010. Alternatively, the sensor electrode 2010 and the electrode supporter 2030 may be formed of different materials, and the sensor electrode 2010 may be attached to the electrode supporter 2030. Since the electrode supporter 2030 is conductive, the electrode supporter 2030 may be connected to the cable 2090 without an additional wiring circuit.

Alternatively, when the tapering portion 2010a and the protruding portion 2010b of the sensor electrode 2010 are separately manufactured and then are adhered to each other, the tapering portion 2010a and the electrode supporter 2030 may be integrally formed with each other. Furthermore, the protruding portion 2010b of the sensor electrode 2010 may be directly attached to the electrode supporter 2030 without the tapering portion 2010a. Even in this case, the protruding portion 2010b of the sensor electrode 2010 may be bent when contacting the body part so that a side portion, that is, an outer circumferential surface, of the protruding portion 2010a contacts the living body to sense bioelectrical signals.

Figure 72:
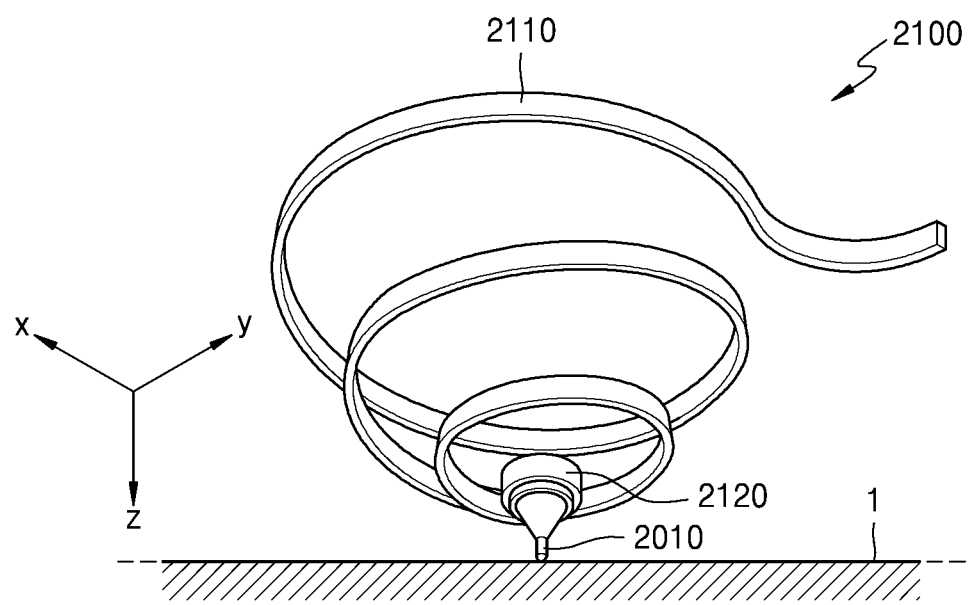
FIG. 72 is a view illustrating a case where the sensor electrode of FIG. 70 is supported by a sensor support.

FIG. 72 is a view illustrating a case where the sensor electrode 2010 is supported by a sensor support 2100.

Referring to FIG. 72, the sensor support 2100 of the present exemplary embodiment that supports the sensor electrode 2010 includes a spiral spring 2110 that is rolled into a circular shape. As shown in FIG. 72, the sensor electrode 2010 may be attached to an inner end 2120 of the spiral spring 2110.

The spiral spring 2110 may be formed of an elastic material such as plastic or metal. Also, the spiral spring 2110 may be formed by rolling a plate-shaped elastic member into a spiral shape. The spiral spring 2110 may elastically support the sensor electrode 2010 in 3-axis directions. That is, the sensor support 2100 of the present exemplary embodiment allows the sensor electrode 2010 to move in any-axis direction in a 3D space. The sensor support 2100 is connected to, for example, the main body 110 (see FIG. 1) of an apparatus for measuring bioelectrical signals that is fixed to the head 1. Since the sensor support 2100 elastically supports the sensor electrode 2010 in 3-axis directions, even when relative positions of the sensor electrode 2010 that is attached to the head 1 and the main body 110 that is fixed to the head 1 therebetween change as the head 1 moves, the sensor electrode 2010 may be stably attached to its original position.

Also, an elasticity of the spiral spring 2110 in a direction (e.g., a z-axis direction) perpendicular to a surface (e.g., an xy plane) on which the spiral spring 2110 is placed may be greater than an elasticity of the spiral spring 2110 in directions (e.g., x- and y-axis directions) parallel to the xy plane, so that a force of pressing the sensor electrode 2010 to the head 1 (that is, an elastic force in the z-axis direction) may be greater than a restoring force in the directions parallel to the xy plane (that is, an elastic force in the x and y-axis directions)

A sensor mount portion 2120 to which the sensor electrode 2010 may be attached may be provided on one inner end of the spiral spring 2110. A method of mounting the sensor electrode 2010 on the sensor mount portion 2120 is not limited thereto. For example, the sensor electrode 2010 may be mounted on the sensor mount portion 2120 by adhering the sensor electrode 2010 to the sensor mount portion 2120. Alternatively, a protruding portion may be formed on a bottom surface of the sensor electrode 2010 and a groove may be formed in the sensor mount portion 2120, and the sensor electrode 2010 may be mounted on the sensor mount portion 2120 by inserting the protruding portion into the groove. Alternatively, a protruding portion may be formed on the sensor mount portion 2120 and a groove may be formed in a bottom surface of the sensor electrode 2010.

The sensor electrode 2010 that is attached to the electrode supporter 2030 (see FIG. 70) may be mounted on the sensor mount portion 2120. The sensor mount portion 2120 may be integrally formed with the electrode supporter 2030 and the electrode supporter 2030 may not be separated from the sensor mount portion 2120.

The sensor electrode 2010 and the sensor support 2100 may be integrally formed by using the same material. Alternatively, the sensor electrode 2010, the electrode supporter 2030, and the sensor support 2100 may be integrally formed by using the same material. When the sensor electrode 2010 and the sensor support 2100 are integrally formed with each other, an additional support member (e.g., an elastic wire formed of a metal material) may reinforce the sensor support 2100 in order to increase an elasticity of the sensor support 2100.

While the inventive concept has been particularly shown and described with reference to exemplary embodiments thereof, they are provided for the purposes of illustration and it will be understood by those of ordinary skill in the art that various modifications and equivalent other embodiments can be made from the inventive concept. Accordingly, the true technical scope of the inventive concept is defined by the technical spirit of the appended claims.

What is claimed is:

1. An apparatus comprising:
a sensor electrode comprising a tapering portion that narrows toward one end and a flexible protruding portion that extends from the one end of the tapering portion and is configured to contact a body part, and senses bioelectrical signals;
an electrode supporter to which an other end opposite from the one end of the tapering portion is attached and which is configured to support the sensor electrode;
a sensor support configured to support the sensor electrode to maintain the contact between the sensor electrode and the body part; and
a main body connected to the sensor support and being wearable on a living body,
wherein, a gradient of a longitudinal section of an outer surface of the flexible protruding portion is greater than a gradient of a longitudinal section of an outer surface of the tapering portion with respect to a bottom surface of the other end of the tapering portion, and
wherein the protruding portion of the sensor electrode is configured to bend and the tapering portion remains stationary with respect to the electrode supporter when a force is applied to the sensor electrode in the direction of the body part, wherein an outer circumferential surface of the protruding portion contacts the body part.

2. The apparatus of claim 1, wherein the flexible protruding portion comprises a flexible material, has a flexibility greater than a flexibility of the tapering portion, and is bent when contacting the body part so that a side portion of the flexible protruding portion contacts the body part, and the tapering portion supports the flexible protruding portion.

3. The apparatus of claim 2, wherein the flexible material is conductive silicone or conductive rubber.

4. The apparatus of claim 1,
wherein an electrode pattern for electrically connecting to the sensor electrode is provided on one of a mount surface of the electrode supporter on which the sensor electrode is mounted or a rear surface of the electrode supporter.

5. The apparatus of claim 4, further comprising a sensor circuit disposed on the rear surface of the electrode supporter or disposed inside the electrode supporter and configured to process the bioelectrical signals detected by the sensor electrode into analog signals or digital signals.

6. The apparatus of claim 1, wherein the sensor support elastically supports a sensor module that includes the sensor electrode and the electrode supporter so that the sensor module moves in 3-axis directions.

7. The apparatus of claim 6, wherein the sensor support comprises a spiral spring, and the sensor module is coupled to one of two ends of the spiral spring,
wherein a surface on which one end of the spiral spring is placed protrudes beyond a surface on which the other end of the spiral spring is placed.

8. The apparatus of claim 7, wherein an elasticity of the spiral spring along a central axis of the spiral spring is greater than an elasticity of the spiral spring in a direction perpendicular to the central axis of the spiral spring.

9. The apparatus of claim 1, further comprising a connection frame configured to connect the sensor support and the main body and to allow the sensor electrode to contact a head of the living body.

10. The apparatus of claim 9, wherein the main body comprises a slot, and one end of the connection frame is detachably inserted into the slot.

11. The apparatus of claim 1, further comprising an auxiliary frame having a hair band shape, a cap shape, or a headband shape, and configured to fix the main body to a head of the living body.

12. The apparatus of claim 1, wherein the main body has a circular band shape or a semicircular band shape to be located along an inner circumferential surface of a cap.

13. The apparatus of claim 1, further comprising:
two main frames corresponding to respective ears of a head of the living body when being worn on the head of the living body;
a plurality of connection frames configured to support the sensor electrode, extend from the two main frames, and configured to allow the sensor electrode to contact the head of the living body when being worn on the head of the living body; and an auxiliary frame configured to elastically connect the two main frames and to fix the two main frames to the head of the living body when being worn on the head of the living body, wherein the main body is provided on at least one of the two main frames.

14. The apparatus of claim 1, further comprising an attachment/detachment coupler configured to detachably couple the main body to a headphone.

15. An apparatus comprising:

a sensor module comprising a sensor electrode that senses bioelectrical signals and an electrode supporter that supports the sensor electrode, wherein the sensor electrode comprises a tapering portion that narrows toward one end and a flexible protruding portion that extends from the one end of the tapering portion, is configured to contact a body part, and senses the bioelectrical signals;

a communication circuit that communicates with an external device;

an output circuit; and a controller that determines an emergency level of a user based on the bioelectrical signals sensed by the sensor module, and controls the output circuit to output an alarm corresponding to the determined emergency level or controls the communication circuit to transmit information about the determined emergency level to the external device through the communication circuit, wherein, a gradient of a longitudinal section of an outer surface of the flexible protruding portion is greater than a gradient of a longitudinal section of an outer surface of the tapering portion with respect to a bottom surface of the other end of the tapering portion, and wherein the protruding portion of the sensor electrode is configured to bend and the tapering portion remains stationary with respect to the electrode supporter when a force is applied to the sensor electrode in the direction of the body part, wherein an outer circumferential surface of the protruding portion contacts the body part.

16. The apparatus of claim 15, further comprising a memory that stores a risk evaluation model for evaluating a first risk level and a second risk level from the bioelectrical signals, the second risk level being higher than the first risk level, wherein the controller controls the output circuit to output the alarm when the emergency level of the user corresponds to the first risk level and controls the communication circuit to transmit information about the emergency level of the user to the external device through the communication circuit when the emergency level of the user corresponds to the second risk level.

17. A system comprising:

an apparatus comprising: a sensor electrode comprising a tapering portion that narrows toward one end and a flexible protruding portion that extends from the one end of the tapering portion, is configured to contact a body part, and senses the bioelectrical signals; an electrode supporter to which an other end opposite from the one end of the tapering portion is attached and which is configured to support the sensor electrode; a sensor support configured to support the sensor electrode to maintain the contact between the sensor electrode and the body part; and a main body connected to the sensor support and being wearable on a living body, and a mobile device for receiving bioelectrical signals from the apparatus, the mobile device comprising:

a communication circuit configured to communicate with the apparatus and an external device;

an output circuit; and a controller configured to determine an emergency level of a user based on the bioelectrical signals received from the apparatus and to control the output circuit to output an alarm corresponding to the determined emergency level or to control the communication circuit to transmit information about the determined emergency level to the external device through the communication circuit, wherein, a gradient of a longitudinal section of an outer surface of the flexible protruding portion is greater than a gradient of a longitudinal section of an outer surface of the tapering portion with respect to a bottom surface of the other end of the tapering portion, and wherein the protruding portion of the sensor electrode is configured to bend and the tapering portion remains stationary with respect to the electrode supporter when a force is applied to the sensor electrode in the direction of the body part, wherein an outer circumferential surface of the protruding portion contacts the body part.

18. The system of claim 17, where the mobile device further comprises a memory configured to store a risk evaluation model for evaluating a first risk level and a second risk level from the bioelectrical signals, the second risk level being higher than the first risk level, wherein the controller controls the output circuit to output the alarm when the emergency level of the user corresponds to the first risk level and controls the communication circuit to transmit information about the emergency level of the user to the external device through the communication circuit when the emergency level of the user corresponds to the second risk level.

19. The system of claim 17, wherein the emergency level of the user comprises a first risk level, and a second risk level that is higher than the first risk level, wherein the controller:

controls the communication circuit to transmit the bioelectrical signals received from the apparatus to a computer device and to receive information about the emergency level of the user that is generated by processing the bioelectrical signals from the computer device through the communication circuit, controls the output circuit to output an alarm through the output circuit when the emergency level of the user received from the computer device is equal to or greater than the first risk level and less than the second risk level, and controls the communication circuit to transmit information about the emergency level of the user to the external device through the communication circuit when the emergency level of the user received from the computer device is greater than or equal to the second risk level.

* * * * *